(12) United States Patent
Chen et al.

(10) Patent No.: US 7,067,620 B2
(45) Date of Patent: Jun. 27, 2006

(54) ANTIBACTERIAL AGENTS

(75) Inventors: Qi-Qi Chen, Irvine, CA (US); John H. Griffin, Atherton, CA (US); Martin S. Linsell, San Mateo, CA (US)

(73) Assignee: Theravance, Inc., South San Francisco, CA (US)

( * ) Notice: Subject to any disclaimer, the term of this patent is extended or adjusted under 35 U.S.C. 154(b) by 646 days.

(21) Appl. No.: 10/274,557

(22) Filed: Oct. 21, 2002

(65) Prior Publication Data

US 2005/0171010 A1   Aug. 4, 2005

Related U.S. Application Data

(63) Continuation of application No. 09/253,670, filed on Feb. 19, 1999, now Pat. No. 6,518,242.

(60) Provisional application No. 60/075,514, filed on Feb. 20, 1998, provisional application No. 60/078,903, filed on Mar. 20, 1998, provisional application No. 60/082,209, filed on Apr. 17, 1998, provisional application No. 60/119,162, filed on Feb. 8, 1999.

(51) Int. Cl.
*C07K 9/00*   (2006.01)

(52) U.S. Cl. .................. 530/317; 530/322; 514/2; 514/8; 514/9

(58) Field of Classification Search ................ 530/317, 530/322; 514/2, 8, 9
See application file for complete search history.

(56) References Cited

U.S. PATENT DOCUMENTS

| | | | |
|---|---|---|---|
| 4,639,433 | A | 1/1987 | Hunt et al. |
| 4,643,987 | A | 2/1987 | Nagarajan et al. |
| 4,698,327 | A | 10/1987 | Nagarajan et al. |
| 5,840,684 | A | 11/1998 | Cooper et al. |
| 5,843,889 | A | 12/1998 | Cooper et al. |
| 5,977,062 | A | 11/1999 | Cooper et al. |
| 6,037,447 | A | 3/2000 | Stack et al. |

FOREIGN PATENT DOCUMENTS

| | | |
|---|---|---|
| EP | 0 667 353 A1 | 8/1995 |
| EP | 0 801 075 A1 | 10/1997 |
| EP | 0 802 199 A2 | 10/1997 |
| WO | WO 97/38702 | 10/1997 |
| WO | WO 97/38706 | 10/1997 |
| WO | WO 98/21952 | 5/1998 |
| WO | WO 98/52589 | 11/1998 |

OTHER PUBLICATIONS

Nagarajan et al. 'Synthesis and Antibacterial Activity of N-Acyl Vancomycins' The Journal of Antibiotics. vol. 41, No. 10, pp. 1430-1438. Oct. 1988.*

* cited by examiner

*Primary Examiner*—Anish Gupta
(74) *Attorney, Agent, or Firm*—Jeffrey A. Hagenah; Joyce G. Cohen

(57) ABSTRACT

Novel antibacterial agents that act as multibinding agents are disclosed. The compounds of the invention comprise from 2–10 ligands covalently connected, each of said ligands being capable of binding to a transglycosylase enzyme substrate thereby modulating the biological processes/functions thereof.

3 Claims, 2 Drawing Sheets

ANTIBACTERIAL AGENTS

This application is a continuation of U.S. Ser. No. 09/253,670, filed Feb. 19, 1999, now U.S. Pat. No. 6,518,242, which claims the benefit under 35 U.S.C. 119 of the following U.S. Provisional Patent Applications: Ser. No. 60/075,514, filed Feb. 20, 1998; Ser. No. 60/078,903, filed Mar. 20, 1998; Ser. No. 60/082,209, filed Apr. 17, 1998; and Ser. No. 60/119,162, filed Feb. 8, 1999; the entire contents of which are hereby incorporated by reference.

FIELD OF THE INVENTION

This invention relates to novel antibacterial agents. More particularly, the invention relates to novel antibacterial agents that act as multibinding agents. The multibinding agents of the invention comprise from 2–10 ligands covalently connected by a linker or linkers, wherein each of said ligands in their monovalent (i.e. unlinked) state have the ability to bind to a cell surface or a precursor used in the synthesis of the bacterial cell wall and thereby interfere with the synthesis of the precursor and the cell wall. The manner in which the ligands are linked is such that the multibinding agents so constructed demonstrate an increased biological and/or therapeutic effect as compared to the same number of unlinked ligands available for binding to the ligand binding site.

The invention also relates to pharmaceutical compositions comprising a pharmaceutically acceptable excipient and an effective amount of a compound of the invention, and to methods of using such compounds and pharmaceutical compositions containing them as antibacterial agents.

Still further, the invention also relates to methods of preparing such compounds.

BACKGROUND

A bacterial cell wall consists of linear polysaccharide chains that are cross-linked by short peptides. This arrangement confers mechanical support to the cell wall, and prevents the bacteria from bursting due to the high internal osmotic pressure. Cross linking takes place after lipid-linked disaccharide-pentapeptide constructs (lipid intermediate II) are incorporated into linear polysaccharide chains by a transglycolase enzyme. The cross-linking reaction is the last step of the synthesis of the cell wall, and is catalyzed by an enzyme known as peptidoglycan transpeptidase.

One method by which antibacterial agents exert their antibacterial activity, is by inhibiting the transglycosylase enzyme, thus interfering with the penultimate step of the synthesis of the bacteria cell wall. Although not wishing to be bound by theory, it is believed that a glycopeptide, for example vancomycin, binds with high affinity and specificity to N-terminal sequences (L-lysyl-D-alanyl-D-alanine in vancomycin-sensitive organisms) of peptidoglycan precursors known as lipid intermediate II. By binding to and sequestering these precursors, vancomycin prevents their utilization by the cell wall biosynthesis machinery. In a formal sense, therefore, vancomycin inhibits the bacterial transglycosylase that is responsible for adding lipid intermediate II subunits to growing peptidoglycan chains. This step preceeds the cross-linking transpeptidation step which is inhibited by beta-lactams antibiotics. It is likely that vancomycin also inhibits transpeptidation which involves the D-alanyl-D-alanine termini; however, as this step occurs subsequent to transglycosylation, inhibition of transpeptidation is not be directly observed.

Antibacterial agents have proved to be important weapons in the fight against pathogenic bacteria. However, an increasing problem with respect to the effectiveness of antibacterial agents relates to the emergence of strains of entrococci that are highly resistant to such agents; for example, vancomycin-resistant entrococci (VRE), which are also multi-drug resistant. It would therefore be highly desirable to find antibacterial agents that are active against a broad spectrum of bacteria, in particular resistant strains such as VRE. It would be also be advantageous to discover antibacterial agents that demonstrate high activity and selectivity toward their targets, and are of low toxicity.

We have discovered that covalent connection of two or more ligands (antibacterial agents) by a linker or linkers provides a multibinding agent that affords an improved biological effect when compared to the same concentration of unlinked ligand (i.e. in its monomeric state), or when compared to a ligand monomer coupled to the linker only. That is to say, an improved biological and/or therapeutic effect of the multibinding agent is obtained as measured against that achieved by the same number of unlinked ligands available for binding to the ligand binding site of the peptidoglycan transglycosylase enzyme substrate.

A preferred ligand is vancomycin. Particularly preferred are vancomycin bivalent compounds, which demonstrate greatly enhanced biological effect when compared to vancomycin monomer, or vancomycin monomer to which is attached the linking structure. They are also highly effective when tested against VRE strains.

Although not wishing to be bound by any particular theory or proposed mechanism of action, it is believed that the surprising activity of the compounds of the invention arises from their ability to bind in a multivalent manner with their target and thus lower the energetic costs of binding (i.e. the phenomena of energetically coupled binding), which is produced by the optimum positioning of two or more molecules of a ligand in relationship to its binding site, i.e., a multivalent interaction. That is to say, the compounds act as multibinding agents, in which ligands that are covalently attached by a linker or linkers simultaneously (or contemporaneously) bind to multiple binding sites on another component, such as an enzyme substrate.

Related Disclosures

Vancomycin derivatives are disclosed in Patent Applications EP 0 802 199, EP 0 801 075, EP 0 667 353, WO 97/28812, WO 97/38702, and in JACS 118, pp 13107–13108 (1996), JACS 119, pp 12041–12047 (1997), and JACS 116, pp 4573–4590 (1994). The disclosures of these and other documents referred to throughout this application (e.g., in the Pharmacology section of the Detailed Description of the Invention) are incorporated herein by reference.

SUMMARY OF THE INVENTION

This invention addresses the above needs by providing novel multibinding agents. Accordingly, in one aspect, the present invention relates to novel multibinding agents;
   wherein a multibinding agent comprises 2–10 ligands, which may be the same or different, covalently connected by a linker or linkers, which may be the same or different, each of said ligands comprising a ligand domain capable of binding to a transglycosylase enzyme substrate.

The preferred multibinding agents are represented by Formula I:

in which L is a ligand that may be the same or different at each occurrence;
X is a linker that may be the same or different at each occurrence;
p is an integer of 2–10; and
q is an integer of 1–20;

or a salt thereof;
wherein each of said ligands comprises a ligand domain capable of binding to a transglycosylase enzyme substrate, thereby modulating the activity of the enzyme substrate. Preferably q is less than p. More preferably p is 2 and q is 1. Particularly preferred is the compound of Formula I wherein L at each occurrence represents optionally substituted vancomycin; and X represents a linker between any hydroxyl group, carboxyl group or amino group of the first vancomycin to any hydroxyl group, carboxyl group or amino group of the second vancomycin.

In a preferred embodiment, the linker, X, is:

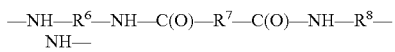

wherein $R^6$, $R^7$, and $R^8$ are optionally substituted alkylene, when X connects the [C] terminus of a first glycopeptide to the [C] terminus of a second glycopeptide.

In another preferred embodiment, the linker, X, is:

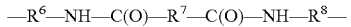

wherein $R^6$, $R^7$, and $R^8$ are optionally substituted alkylene, when X connects the [V] terminus of a first glycopeptide to the [V] terminus of a second glycopeptide.

In still another preferred embodiment, the linker, X is:

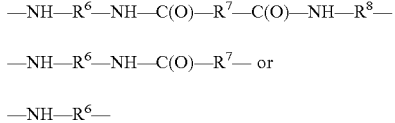

wherein $R^6$, $R^7$, and $R^8$ are optionally substituted alkylene, when X connects the [C] terminus of a first glycopeptide to the [V] terminus of a second glycopeptide.

In a second aspect, the invention relates to a method of treatment of mammals having a disease state that is treatable by an antibacterial agent, comprising administering a therapeutically effective amount of a novel multibinding agent thereto;
wherein a multibinding agent comprises 2–10 ligands, which may be the same or different, covalently connected by a linker or linkers, which may be the same or different, each of said ligands comprising a ligand domain capable of binding to a transglycosylase enzyme substrate. The preferred multibinding agent is a compound of Formula I, or a mixture of compounds of Formula I.

In a third aspect, the invention relates to a method of treatment of mammals having a bacterial disease characterized by resistance to vancomycin, comprising administering a therapeutically effective amount of a multibinding agent as defined above, preferably a compound of Formula I, thereto, or a mixture of multibinding agents.

In a fourth aspect, the invention relates to a pharmaceutical composition comprising a therapeutically effective amount of one or more multibinding agents, or a pharmaceutically acceptable salt thereof, said multibinding agent comprising 2–10 ligands, which may be the same or different, covalently connected by a linker or linkers, which may be the same or different, each of said ligands comprising a ligand domain capable of binding to a transglycosylase enzyme substrate, admixed with at least one pharmaceutically acceptable excipient, wherein the multibinding agent is preferably a compound of Formula I.

In a fifth aspect, the invention relates to processes for preparing the multibinding agents of the invention.

DEFINITIONS

Figure 1:
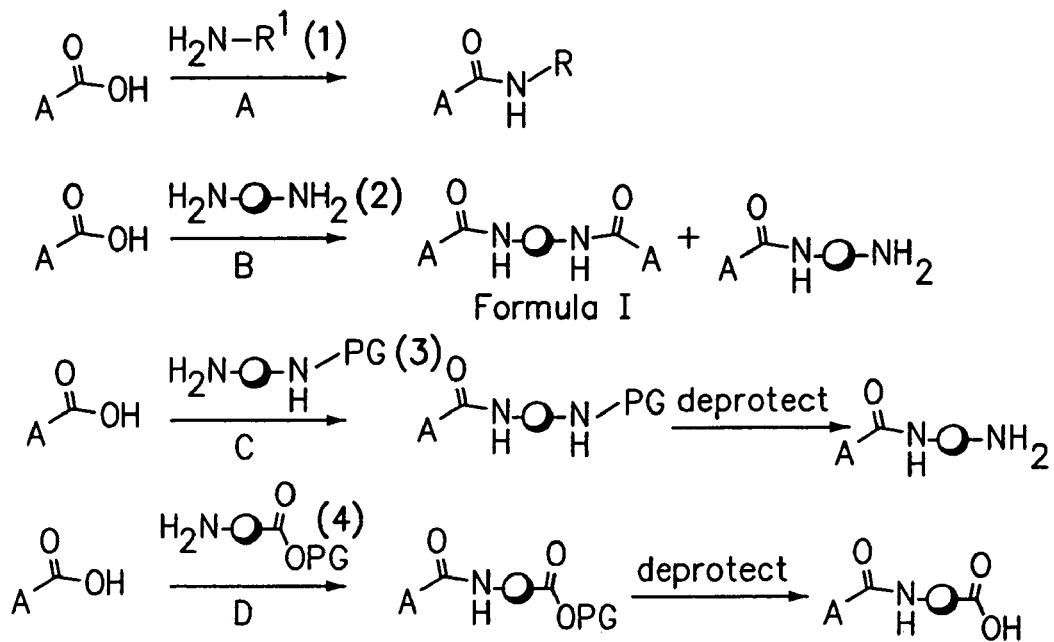
FIG. 1 illustrates the synthesis of a compound of formula I and intermediates thereof using a carboxylic acid compound and an amine or diamine compound.

As used herein:

The term "alkyl" refers to a monoradical branched or unbranched saturated hydrocarbon chain, preferably having from 1 to 40 carbon atoms, preferably 1–10 carbon atoms, more preferably 1–6 carbon atoms, such as methyl, ethyl, n-propyl, isopropyl, n-butyl, secondary butyl, tert-butyl, n-hexyl, n-octyl, n-decyl, n-dodecyl, 2-ethyldodecyl, tetradecyl, and the like, unless otherwise indicated.

The term "substituted alkyl" refers to an alkyl group as defined above having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

The term "alkylene" refers to a diradical of a branched or unbranched saturated hydrocarbon chain, preferably having from 1 to 40 carbon atoms, preferably 1–10 carbon atoms, more preferably 1–6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "substituted alkylene" refers to:

(a) an alkylene group as defined above having from 1 to 5 substituents selected from the group consisting of alkoxy, substituted alkoxy, cycloalkyl, substituted cycloalkyl, cycloalkenyl, substituted cycloalkenyl, acyl, acylamino (including, for example, N-glucosaminecarbonyl, benzoylamino, biphenylcarbonylamino, and the like), acyloxy, amino, aminoacyl, aminoacyloxy, oxyacylamino, azido, cyano, halogen, hydroxyl, keto, thioketo, carboxyl, carboxylalkyl, thiol, thioalkoxy, substituted thioalkoxy, aryl, aryloxy, thioaryloxy, heteroaryl, heteroaryloxy, thioheteroaryloxy, heterocyclic, heterocylcooxy, thioheterocylcooxy, nitro, and —$NR^aR^b$, wherein $R^a$ and $R^b$ may be the same or different and are chosen from hydrogen, optionally substituted alkyl, cycloalkyl, alkenyl, cycloalkenyl, alkynyl, aryl, heteroaryl and heterocyclic. Additionally, such substituted alkylene groups include those where 2 substituents on the alkylene group are fused to form one or more cycloalkyl, substituted cycloalkyl, cycloalkenyl, substituted cycloalkenyl, aryl, heterocyclic or heteroaryl groups fused to the alkylene group.

(b) an alkylene group as defined above that is interrupted by 1–20 atoms or substituents independently chosen from oxygen, sulfur and $NR^a$—, wherein $R^a$ is chosen from hydrogen, optionally substituted alkyl, cycloalkyl, alkenyl, cycloalkenyl, alkynyl, aryl, heteroaryl and heterocyclic; or (c) an alkylene group as defined above that has both from 1 to 5 substituents as defined above and is also interrupted by 1–20 atoms as defined above.

Examples of substituted alkylenes are chloromethylene (—CH(Cl)—), aminoethylene (—CH($NH_2$)$CH_2$—), 1-(dodecanoylamino)propylene (—CH[NHC(O)—($CH_2$)$_{11}$—$CH_3$]$CH_2$—), 1-(4-phenylbenzoylamino)pentylene (—CH[NHC(O)—Z]($CH_2$)$_4$),2-carboxypropylene isomers (—$CH_2$CH($CO_2$H)$CH_2$—), ethoxyethyl (—$CH_2CH_2$O—$CH_2CH_2$—),—), ethylmethylaminoethyl (—$CH_2CH_2$N($CH_3$)$CH_2CH_2$—), 1-ethoxy-2-(2-ethoxy-ethoxy)ethane(—$CH_2CH_2$O—$CH_2CH_2$—O—$CH_2CH_2$O—$CH_2CH_2$—), and the like.

The term "alkaryl" or "aralkyl" refers to the groups -alkylene-aryl and -substituted alkylene-aryl in which alkylene and aryl are as defined herein. Such alkaryl groups are exemplified by benzyl, phenethyl and the like.

The term "alkoxy" refers to the groups alkyl-O—, alkenyl-O—, cycloalkyl-O—, cycloalkenyl-O—, and alkynyl-O—, where alkyl, alkenyl, cycloalkyl, cycloalkenyl, and alkynyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like The term "substituted alkoxy" refers to the groups substituted alkyl-O—, substituted alkenyl-O—, substituted cycloalkyl-O—, substituted cycloalkenyl-O—, and substituted alkynyl-O—where substituted alkyl, substituted alkenyl, substituted cycloalkyl, substituted cycloalkenyl and substituted alkynyl are as defined herein.

The term "alkylalkoxy" refers to the groups -alkylene-O-alkyl, alkylene-O-substituted alkyl, substituted alkylene-O-alkyl and substituted alkylene-O-substituted alkyl wherein alkyl, substituted alkyl, alkylene and substituted alkylene are as defined herein. Examples of such groups are methylenemethoxy (—$CH_2OCH_3$), ethylenemethoxy (—$CH_2CH_2OCH_3$), n-propylene-iso-propoxy (—$CH_2CH_2CH_2OCH(CH_3)_2$), methylene-t-butoxy (—$CH_2$—O—$C(CH_3)_3$) and the like.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein. Preferred alkylthioalkoxy groups are alkylene-S-alkyl and include, by way of example, methylenethiomethoxy (—$CH_2SCH_3$), ethylenethiomethoxy (—$CH_2CH_2SCH_3$), n-propylene-iso-thiopropoxy (—$CH_2CH_2CH_2SCH(CH_3)_2$), methylene-t-thiobutoxy (—$CH_2SC(CH_3)_3$) and the like. "Alkenyl" refers to a monoradical of a branched or unbranched unsaturated hydrocarbon preferably having from 2 to 40 carbon atoms, preferably 2–10 carbon atoms, more preferably 2–6 carbon atoms, and preferably having 1–6 double bonds. This term is further exemplified by such radicals as vinyl, prop-2-enyl, pent-3-enyl, hex-5-enyl, 5-ethyldodec-3,6-dienyl, and the like.

The term "substituted alkenyl" refers to an alkenyl group as defined above having from 1 to 5 substituents selected from the group consisting of alkoxy, substituted alkoxy, acyl, acylamino, acyloxy, amino, aminoacyl, aminoacyloxy, oxyaminoacyl, azido, cyano, halogen, hydroxyl, keto, thioketo, carboxyl, carboxylalkyl, thiol, thioalkoxy, substituted thioalkoxy, aryl, heteroaryl, heterocyclic, aryloxy, thioaryloxy, heteroaryloxy, thioheteroaryloxy, heterocylcooxy, thioheterocylcooxy, nitro, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl, and. —$NR^aR^b$, wherein $R^a$ and $R^b$ may be the same or different and are chosen from hydrogen, optionally substituted alkyl, cycloalkyl, alkenyl, cycloalkenyl, alkynyl, aryl, heteroaryl and heterocyclic.

"Alkenylene" refers to a diradical of an unsaturated hydrocarbon, preferably having from 2 to 40 carbon atoms, preferably 2–10 carbon atoms, more preferably 2–6 carbon atoms, and preferably having 1–6 double bonds. This term is further exemplified by such radicals as 1,2-ethenyl, 1,3-prop-2-enyl, 1,5-pent-3-enyl, 1,4-hex-5-enyl, 5-ethyl-1,12-dodec-3,6-dienyl, and the like.

The term "substituted alkenylene" refers to an alkenylene group as defined above having from 1 to 5 substituents, selected from the group consisting of alkoxy, substituted alkoxy, acyl, acylamino, acyloxy, amino, aminoacyl, aminoacyloxy, oxyacylamino, azido, cyano, halogen, hydroxyl, keto, thioketo, carboxyl, carboxylalkyl, thiol, thioalkoxy, substituted thioalkoxy, aryl, aryloxy, thioaryloxy, heteroaryl, heteroaryloxy, thioheteroaryloxy, heterocyclic, heterocylcooxy, thioheterocylcooxy, nitro, and $NR^aR^b$, wherein $R^a$ and $R^b$ may be the same or different and are chosen from hydrogen, optionally substituted alkyl, cycloalkyl, alkenyl, cycloalkenyl, alkynyl, aryl, heteroaryl and heterocyclic. Additionally, such substituted alkenylene groups include those where 2 substituents on the alkenylene group are fused to form one or more cycloalkyl, substituted cycloalkyl, cycloalkenyl, substituted cycloalkenyl, aryl, heterocyclic or heteroaryl groups fused to the alkenylene group.

"Alkynyl" refers to a monoradical of an unsaturated hydrocarbon, preferably having from 2 to 40 carbon atoms, preferably 2–10 carbon atoms, more preferably 2–6 carbon atoms, and preferably having 1–6 triple bonds. This term is further exemplified by such radicals as acetylenyl, prop-2-ynyl, pent-3-ynyl, hex-5-ynyl, 5-ethyldodec-3,6-diynyl, and the like.

The term "substituted alkynyl" refers to an alkynyl group as defined above having from 1 to 5 substituents, selected from the group consisting of alkoxy, substituted alkoxy, acyl, acylamino, acyloxy, amino, aminoacyl, aminoacyloxy, oxyacylamino, azido, cyano, halogen, hydroxyl, keto, thioketo, carboxyl, carboxylalkyl, thiol, thioalkoxy, substituted thioalkoxy, aryl, aryloxy, thioaryloxy, heteroaryl, heteroaryloxy, thioheteroaryloxy, heterocyclic, heterocyclooxy, thioheterocycloxy, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, SO$_2$-heterocyclic, NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

"Alkynylene" refers to a diradical of an unsaturated hydrocarbon radical, preferably having from 2 to 40 carbon atoms, preferably 2–10 carbon atoms, more preferably 2–6 carbon atoms, and preferably having 1–6 triple bonds. This term is further exemplified by such radicals as 1,3-prop-2-ynyl, 1,5-pent-3-ynyl, 1,4-hex-5-ynyl, 5-ethyl-1,12-dodec-3,6-diynyl, and the like.

The term "acyl" refers to the groups —CHO, alkyl-C(O)—, substituted alkyl-C(O)—, cycloalkyl-C(O)—, substituted cycloalkyl-C(O)—, cycloalkenyl-C(O)—, substituted cycloalkenyl-C(O)—, aryl-C(O)—, heteroaryl-C(O)— and heterocyclic-C(O)— where alkyl, substituted alkyl, cycloalkyl, substituted cycloalkyl, cycloalkenyl, substituted cycloalkenyl, aryl, heteroaryl and heterocyclic are as defined herein.

The term "acylamino" refers to the group —C(O)NRR where each R is independently hydrogen, alkyl, substituted alkyl, aryl, heteroaryl, heterocyclic or where both R groups are joined to form a heterocyclic group (e.g., morpholino) wherein alkyl, substituted alkyl, aryl, heteroaryl and heterocyclic are as defined herein.

The term "aminoacyl" refers to the group —NRC(O)R where each R is independently hydrogen, alkyl, substituted alkyl, aryl, heteroaryl, or heterocyclic wherein alkyl, substituted alkyl, aryl, heteroaryl and heterocyclic are as defined herein.

The term "aminoacyloxy" refers to the group —NRC(O)OR where each R is independently hydrogen, alkyl, substituted alkyl, aryl, heteroaryl, or heterocyclic wherein alkyl, substituted alkyl, aryl, heteroaryl and heterocyclic are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

The term "alkylamino" refers to the group —NHR$^a$, where R$^a$ is alkyl as defined above. The term "alkylaminoalkyl" rfers to the group —R$^b$—NHR$^a$, where R$^a$ is alkyl as defined above, and R$^b$ is alkylene as defined above. Examples of alkylaminoalkyl are n-decylaminoethyl, 3-(dimethylamino)propyl, and the like.

The term "aryl" refers to an unsaturated aromatic carbocyclic group of from 6 to 20 carbon atoms having a single ring (e.g., phenyl) or multiple condensed (fused) rings (e.g., naphthyl or anthryl).

Unless otherwise constrained by the definition for the aryl substituent, such aryl groups can optionally be substituted with from 1 to 5 substituents selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, trihalomethyl, NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic. Preferred aryl substituents include alkyl, alkoxy, halo, cyano, nitro, trihalomethyl, and thioalkoxy.

The term "aryloxy" refers to the group aryl-O— wherein the aryl group is as defined above including optionally substituted aryl groups as also defined above.

The term "arylene" refers to a diradical derived from aryl or substituted aryl as defined above, and is exemplified by 1,2-phenylene, 1,3-phenylene, 1,4-phenylene, 1,2-naphthylene and the like.

The term "carboxyalkyl" refers to the group "—C(O)Oalkyl" where alkyl is as defined above.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents selected from the group consisting of alkoxy, substituted alkoxy, cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

The term "cycloalkenyl" refers to cyclic alkenyl groups of from 4 to 20 carbon atoms having a single cyclic ring or fused rings and at least one point of internal unsaturation. Examples of suitable cycloalkenyl groups include, for instance, cyclobut-2-enyl, cyclopent-3-enyl, cyclooct-3-enyl and the like.

The term "substituted cycloalkenyl" refers to cycloalkenyl groups having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

The term "halo" or "halogen" refers to fluoro, chloro, bromo and iodo.

"Haloalkyl" refers to alkyl as defined above substituted by 1–4 halo groups as defined above, which may be the same or different, such as 3-fluorododecyl, 12,12,12-trifluorododecyl, 2-bromooctyl, -3-bromo-6-chloroheptyl, and the like.

The term "heteroaryl" refers to an aromatic group of from 1 to 15 carbon atoms and 1 to 4 heteroatoms selected from oxygen, nitrogen and sulfur within at least one ring (if there is more than one ring).

Unless otherwise constrained by the definition for the heteroaryl substituent, such heteroaryl groups can be optionally substituted with 1 to 5 substituents selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, trihalomethyl, mono-and di-alkylamino, and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic. Preferred heteroaryls nclude pyridyl, pyrrolyl and furyl.

The term "heteroaryloxy" refers to the group heteroaryl-O—.

The term "heteroarylene" refers to the diradical group derived from heteroaryl or substituted heteroaryl as defined above, and is exemplified by the groups 2,6-pyridylene, 2,4-pyridiylene, 1,2-quinolinylene, 1,8-quinolinylene, 1,4-benzofuranylene, 2,5-pyridinylene, 1,3-morpholinylene, 2,5-indolenyl, and the like.

The term "heterocycle" or "heterocyclic" refers to a monoradical saturated or unsaturated group having a single ring or multiple condensed rings, from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic. Such heterocyclic groups can have a single ring or multiple condensed rings.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

The term "heterocyclics" includes "crown compounds" which refers to a specific class of heterocyclic compounds having one or more repeating units of the formula [—(CH$_2$—)$_m$Y—] where m is equal to or greater than 2, and Y at each separate occurrence can be O, N, S or P. Examples of crown compounds include [—(CH$_2$)$_3$—NH—]$_3$, [—((CH$_2$)$_2$—O)$_4$—((CH$_2$)$_2$—NH)$_2$] and the like. Typically such crown compounds can have from 4 to 10 heteroatoms and 8 to 40 carbon atoms.

The term "heterocyclooxy" refers to the group heterocyclic-O—.

The term "thioheterocyclooxy" refers to the group heterocyclic-S—.

The term "heterocyclene" refers to the diradical group derived from a heterocycle as defined herein, and is exemplified by the groups 2,6-morpholino, 2,5-morpholino and the like.

The term "oxyacylamino" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

The term "thiol" refers to the group —SH.

The term "thioalkoxy" refers to the group —S-alkyl.

The term "substituted thioalkoxy" refers to the group —S-substituted alkyl.

The term "thioaryloxy" refers to the group aryl-S— wherein the aryl group is as defined above including optionally substituted aryl groups also defined above.

The term "thioheteroaryloxy" refers to the group heteroaryl-S— wherein the heteroaryl group is as defined above including optionally substituted aryl groups as also defined above.

As to any of the above groups which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

"Alkyl optionally interrupted by 1–5 atoms chosen from O, S, or N" refers to alkyl as defined above in which the carbon chain is interrupted by O, S, or NR$^a$, where R$^a$ is hydrogen, alkyl, aryl, or heteroaryl, all of which may be optionally substituted. Within the scope are ethers, sulfides, and amines, for example 1-methoxydecyl, 1-pentyloxynonane, 1-(2-isopropoxyethoxy)-4-methylnonane, 1-(2-ethoxyethoxy)dodecyl, 2-(t-butoxy)heptyl, 1-pentylsulfanylnonane, nonylpentylamine, and the like.

"Heteroarylalkyl" refers to heteroaryl as defined above linked to alkyl as defined above, for example pyrid-2-ylmethyl, 8-quinolinylpropyl, and the like.

"Ligand" as used herein denotes an antibiotic compound that is a binding partner for a transglycosylase enzyme substrate and is bound thereto by complementarity. The specific region or regions of the ligand that is (are) recognized by the enzyme substrate is designated as the "ligand domain". By virtue of the ligand domain, a ligand may be either capable of binding to a transglycosylase enzyme substrate by itself, or may require the presence of one or more non-ligand components for binding (e.g. Ca$^{2+}$, Mg$^{2+}$, or a water molecule is required for the binding of a ligand domain).

Those skilled in the art will appreciate that portions of the ligand structure that are not essential for molecular recognition and binding activity (i.e. that are not part of the ligand domain) may be varied substantially, replaced or substituted with unrelated structures (for example, with ancillary groups as defined below), and, in some cases, omitted entirely without affecting the binding interaction. Accordingly, it should be understood that the term ligands is not intended to be limited to compounds known to be useful as antibiotics (for example, known drugs). Those skilled in the art will understand that the term ligand can equally apply to a molecule that is not normally recognized as having useful antibacterial properties, in that ligands that exhibit minimally useful properties as monomers can be highly active as multibinding agents, due to the biological benefit (increased biological effect) conferred by multivalency. The primary requirement for a ligand as defined herein is that it has a ligand domain as defined above.

ropolysporin, Decaplanin, N-demethylvancomycin, Eremomycin, Galacardin, Helvecardin, Izupeptin, Kibdelin, LL-AM374, Mannopeptin, MM45289, MM47756, MM47761, MM49721, MM47766, MM55260, MM55266, MM55270, MM56597, MM56598, OA-7653, Orenticin, Parvodicin, Ristocetin, Ristomycin, Synmonicin, Teicoplanin, UK-68597, UK-69542, UK-72051, vancomycin, and the like. Another preferred class of ligands is the general class of glycopeptides disclosed above on which the sugar moiety is absent, i.e., the aglycone series of heptapeptides. For example, removal of the disaccharide moiety appended to the phenol on vancomycin (as shown below as Formula II) by mild hydrolysis gives vancomycin aglycone. A further preferred class of ligands are glycopeptides that have been further appended with additional saccharide residues, especially aminoglycosides, in a manner similar to vancosamine.

"Vancomycin" refers to the antibacterial compound whose structure is reproduced below as Formula II.

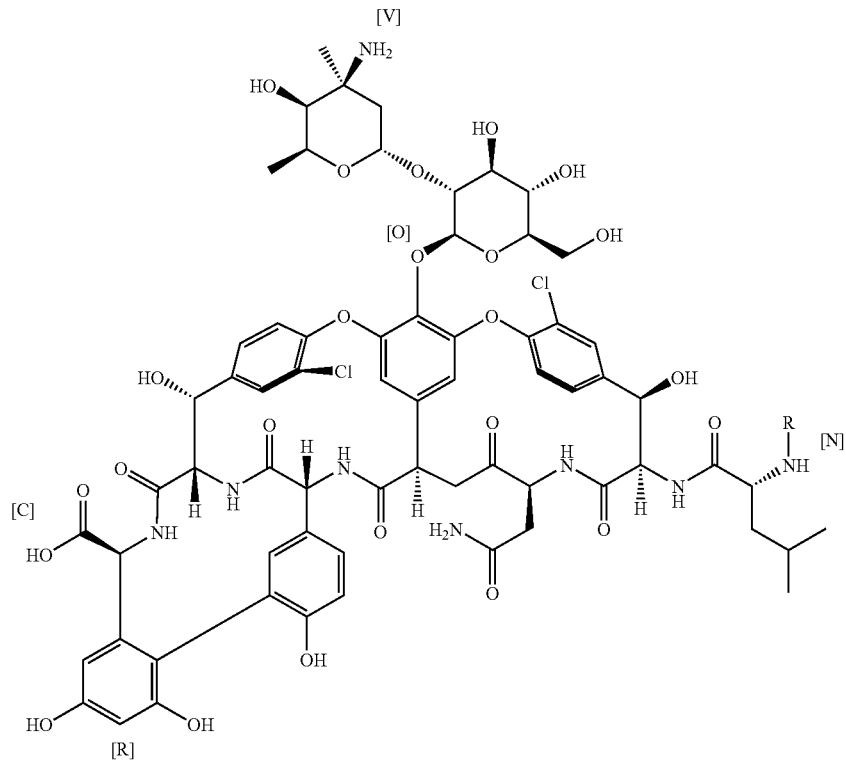

Formula II

A preferred class of ligands are heptapeptides, known as the glycopeptide antibiotics, characterized by a multi-ring peptide core, and at least one sugar attached at various sites, of which vancomycin is an important example. Examples of the glycopeptide class of ligands included in this definition may be found in "Glycopeptides Classification, Occurrence, and Discovery," by Raymond C. Rao and Louise W. Crandall, ("Drugs and the Pharmaceutical Sciences", Volume 63, edited by Ramakrishnan Nagarajan, published by Marcal Dekker, Inc.). Disclosed are glycopeptides identified as A477, A35512, A40926, A41030, A42867, A47934, A80407, A82846, A83850, A84575, A84428, AB-65, Actaplanin, Actinoidin, Ardacin, Avoparcin, Azureomycin, Balhimycin, Chloroeremomycin, Chloroorientein, Chlo- "Optional" or "optionally" means that the subsequently described event or circumstance may or may not occur, and that the description includes instances where said event or circumstance occurs and instances in which it does not. For example, "optionally substituted glycopeptide" with respect to a compound of Formula I refers to a ligand as defined above in which those positions that are not linked to X may or may not be substituted by various groups as defined below. The term also includes those instances in which one amino acid of the basic core structure is replaced by another amino acid, for example as described in "Preparation and conformational analysis of vancomycin hexapeptide and aglucovancomycin hexapeptide", by Booth, Paul M.; Williams, Dudley H., Univ. Chem. Lab., Cambridge, UK., J.

Chem. Soc., Perkin Trans. 1 (1989), (12), 2335–9, and "The Edman degradation of vancomycin: preparation of vancomycin hexapeptide", Booth, Paul M.; Stone, David J. M.; Williams, Dudley H., Univ. Chem. Lab., Cambridge, UK., J. Chem. Soc., Chem. Commun. (1987), (22), 1694–5. "Optionally substituted vancomycin" with respect to the multibinding agents of the invention refers to vancomycin in which the hydroxy group at any position, the [R] position, the carboxyl groups at the [C] position, or the amine groups at the [V] or [N] position that are not attached to the linker X may or may not be substituted by various groups. Such groups include:

$R^a$, where $R^a$ at each occurrence is chosen from alkyl, alkyl optionally interrupted by 1–5 atoms chosen from O, S, or $NR^b$, where $R^b$ is alkyl, aryl, or heteroaryl, all of which are optionally substituted, haloalkyl, alkenyl, alkynyl, alkylamino, alkylaminoalkyl, cycloalkyl, alkanoyl, aryl, heteroaryl, heterocyclic, additional saccharide residues, especially aminoglycosides, all of which are optionally substituted as defined above; and:

$NR^cR^d$, in which $R^c$ and $R^d$ are independently hydrogen, alkyl, alkenyl, alkynyl, cycloalkyl, alkanoyl, aryl, heteroaryl, arylalkyl, or heteroarylalkyl, or $R^c$ and $R^d$ when taken together with the nitrogen to which they are attached represent a heterocyclo group, quarternary alkyl and aryl ammonium compounds, pyridinium ions, sulfonium ions, and the like, all of which are optionally substituted as defined above. An example of a preferred [C] substitution is dimethylaminopropylamino and glucosamino; an example of a preferred [V] substitution is alkyl, for example n-decyl, or alkylaminoalkyl, for example n-decylaminoethyl. "Optionally substituted vancomycin aglycone" with respect to the multibinding agents of the invention refers to vancomycin aglycone in which the hydroxy group at any position, particularly the hydroxy group at the [O] position, the [R] position, the carboxyl groups at the [C] position, or the amine group at the [N] position, that are not attached to the linker X may or may not be substituted by various groups —$R^a$ as defined above.

"Transglycosylase enzyme substrate" as used herein denotes the molecular target of the transpeptidase enzyme. The substrate binds to the enzyme and eventually results in synthesis of the bacterial cell wall. The action of this enzyme is inhibited by a ligand domain that binds to the enzyme substrate. A ligand such as vancomycin binds to this substrate and in effect "sequesters" the substrate to prevent its recognition by the enzyme and subsequent use in the construction of the bacterial cell wall.

"Multibinding agent" or "multibinding compound" as used herein refers to a compound that is capable of multivalency as defined below, and which has 2–10 ligands, which may be the same or different, connected by one or more covalent linker or linkers, which may be the same or different, preferably from 1–20. A multibinding agent provides a biological and/or therapeutic effect greater than the aggregate of the unlinked ligands equivalent thereto. That is to say, an improved biological and/or therapeutic effect of the multibinding agent is obtained as measured against that achieved by the same number of unlinked ligands available for binding to the ligand binding site of the transglycosylase enzyme substrate. Examples of increased biological and/or therapeutic effect with respect to the target include, for example, increased specificity, increased affinity, increased selectivity, increased potency, increased efficacy, increased therapeutic index, a change in the duration of action, decreased toxicity, decreased side effects, improved bioavailability, improved pharmacokinetics, improved activity spectrum, improved ability to kill bacteria, and the like. The multibinding compounds of the invention will exhibit one or more of the foregoing effects.

"Potency" as used herein refers to the minimum concentration at which a ligand is able to achieve a desirable biological or therapeutic effect. The potency of a ligand is typically proportional to its affinity for its ligand binding site. In some cases, the potency may be nonlinearly correlated with its affinity. In comparing the potency of two drugs, e.g., a multibinding agent and the aggregate of its unlinked ligand, the dose-response curve of each is determined under identical test conditions (e.g., in an in vitro or in vivo assay or in an appropriate animal model, such as a human patient. The finding that the multibinding agent produces an equivalent biological or therapeutic effect at a lower concentration than the aggregate unlinked ligand (e.g., on a per weight, per mole, or per ligand basis) is indicative of enhanced potency.

"Univalency" as used herein refers to a single binding interaction between the ligand domain of one ligand as defined herein with the ligand recognition site of a transglycosylase enzyme substrate as defined herein. It should be noted that a compound having multiple copies of a ligand (or ligands) exhibits univalency when only one ligand of that compound is interacting with a ligand binding site. Examples of univalent interactions are depicted below.

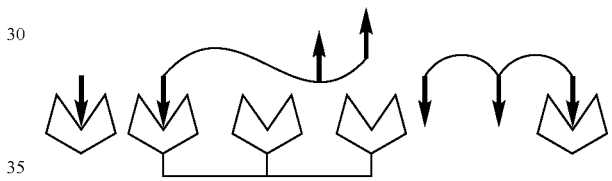

where the arrow represents a ligand domain and the indent represents the ligand binding site of a transglycosylase enzyme substrate, "Multivalency" as used herein refers to the concurrent binding of 2 to 10 linked ligands (which may be the same or different) and two or more corresponding ligand binding sites.

Accordingly, two ligands connected by a linker that bind concurrently to two ligand binding sites would be considered as a bivalent compound; similarly, three ligands thus connected provide a trivalent compound.

It should be understood that all compounds that contain multiple copies of a ligand attached to a linker (or linkers) do not necessarily exhibit the phenomena of multivalency, i.e. that improved biological and/or therapeutic effect of the multibinding agent is obtained as measured against that produced by the same number of unlinked ligands available for binding to a ligand binding site. For multivalency to occur, the ligand domains of the ligands that are connected by a linker have to be presented to their "receptors" (i.e. the ligand binding sites) by the linker in a specific manner in order to bring about the desired ligand-orienting result, and thus produce a multibinding event.

"Selectivity" or "specificity" in general is a measure of the binding preferences of a ligand for different receptors and/or different ligands for the same receptor. The selectivity of a ligand with respect to its target receptor relative to another receptor is given by the ratio of the respective values of $K_d$ (i.e., the dissociation constants for each ligand-receptor complex), or in cases where a biological effect is observed below the $K_d$, selectivity is given by the ratio of the respective $EC_{50}$s (i.e. the concentrations that produce 50% of the maximum response for the ligand interacting with the two distinct receptors).

The term "ligand recognition site" or "ligand binding site" as used herein denotes the site on a transglycosylase enzyme substrate that recognizes a ligand domain and provides a binding partner. The ligand binding site may be defined by monomeric or multimeric structures.

As used herein, the terms "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform ("CHCl$_3$"), methylene chloride (or dichloromethane or "CH$_2$Cl$_2$), diethyl ether, ethyl acetate, acetone, methylethyl ketone, methanol, ethanol, propanol, isopropanol, tert-butanol, dioxane, pyridine, and the like]. Unless specified to the contrary, the solvents used in the reactions of the present invention are inert solvents.

"Pharmaceutically acceptable salt" means those salts which retain the biological effectiveness and properties of the compounds of Formula I, and which are not biologically or otherwise undesirable. The compounds of Formula I are capable of forming both acid and base salts by virtue of the presence of amino and carboxyl groups respectively.

1. Pharmaceutically acceptable base addition salts may be prepared from inorganic and organic bases. Salts derived from inorganic bases include, but are not limited to, the sodium, potassium, lithium, ammonium, calcium, and magnesium salts. Salts derived from organic bases include, but are not limited to, salts of primary, secondary and tertiary amines, substituted amines including naturally-occurring substituted amines, and cyclic amines, including isopropylamine, trimethyl amine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, and N-ethylpiperidine. It should also be understood that other carboxylic acid derivatives would be useful in the practice of this invention, for example carboxylic acid amides, including carboxamides, lower alkyl carboxamides, di(lower alkyl) carboxamides, and the like.

2. Pharmaceutically acceptable acid addition salts may be prepared from inorganic and organic acids. Salts derived from inorganic acids include hydrochloric acid, hydrobromic acid, sulfuric acid, nitric acid, phosphoric acid and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

It should be understood that the compounds of the invention include racemic ligands as well as the individual stereoisomers of the ligands, including enantiomers and non-racemic mixtures thereof. The scope of the invention as described and claimed encompasses the racemic forms of the ligands as well as the individual enantiomers and non-racemic mixtures thereof.

The term "treatment" as used herein covers any treatment of a condition or disease in an animal, particularly a mammal, more particularly a human, and includes:

(i) preventing the disease or condition from occurring in a subject which may be predisposed to the disease but has not yet been diagnosed as having it;
(ii) inhibiting the disease or condition, i.e. arresting its development;
(iii) relieving the disease or condition, i.e. causing regression of the condition; or.
(iv) relieving the conditions caused by the disease, i.e. symptoms of the disease.

The term "disease state that is alleviated by treatment with an antibacterial agent" as used herein is intended to cover all disease states which are acknowledged in the art to be usefully treated with an antibacterial agent in general, and those disease states which have been found to be usefully treated by the specific antibacterials of our invention, including the compounds of Formula I. Such disease states include, but are not limited to, treatment of a mammal afflicted with pathogenic bacteria, in particular staphylococci (methicillin sensitive and resistant), streptococci (penicillin sensitive and resistant), enterococci (vancomycin sensitive and resistant), and *Clostridium difficile*.

The term "therapeutically effective amount" refers to that amount which is sufficient to effect treatment, as defined above, when administered to a mammal in need of such treatment. The therapeutically effective amount will vary depending on the subject and disease state being treated, the severity of the affliction and the manner of administration, and may be determined routinely by one of ordinary skill in the art.

The term "protecting group" or "blocking group" refers to any group which when bound to one or more hydroxyl, thiol, amino or carboxyl groups of the compounds prevents reactions from occurring at these groups and which protecting group can be removed by conventional chemical or enzymatic steps to reestablish the hydroxyl, thio, amino or carboxyl group. The particular removable blocking group employed is not critical and preferred removable hydroxyl blocking groups include conventional substituents such as allyl, benzyl, acetyl, chloroacetyl, thiobenzyl, benzylidine, phenacyl, t-butyl-diphenylsilyl and any other group that can be introduced chemically onto a hydroxyl functionality and later selectively removed either by chemical or enzymatic methods in mild conditions compatible with the nature of the product. Protecting groups are disclosed in more detail in T. W. Greene and P. G. M. Wuts, "Protective Groups in Organic Synthesis" $2^{nd}$ Ed., 1991, John Wiley and Sons, N.Y.

Preferred removable amino blocking groups include conventional substituents such as t-butyoxycarbonyl (t-BOC), benzyloxycarbonyl (CBZ), fluorenylmethoxycarbonyl (FMOC), allyloxycarbonyl (ALOC) and the like, which can be removed by conventional conditions compatible with the nature of the product.

Preferred carboxyl protecting groups include esters such as methyl, ethyl, propyl, t-butyl etc. which can be removed by mild conditions compatible with the nature of the product.

"Linker" or "linkers" as used herein, identified where appropriate by the symbol X, refers to a group or groups that covalently link(s) from 2–10 ligands (as defined herein) in a manner that provides a multibinding agent capable of multivalency. The linker is a ligand domain orienting entity that permits attachment of multiple copies of ligands (which may be the same or different) thereto. The extent to which multivalent binding is realized depends upon the efficiency with which the linker that joins the ligands permits the ligand domains to be presented to the ligand recognition sites (on enzymes and enzyme substrates). Beyond presenting ligand domains for multivalent interactions with multivalent receptors (enzymes or enzyme substrates), the linker spatially constrains these interactions to occur within dimensions defined by the linker. Thus, the structural features of the linker (valency, geometry, orienting capabilities, size, flexibility, chemical composition) are features of multibinding agents that play an important role in determining their activities. The term linker, however, does not include solid inert supports such as beads, resins, glass particles, rods, fibres, and the like, but it should be understood that the multibinding compounds of the invention can be attached to a solid support if desired to provide, for example, a material useful for separation and purification processes (e.g. affinity chromatography).

The ligands are covalently attached to the linker or linkers using conventional chemical techniques, for example reaction between a carboxylic acid and an amine to form an amide, an amine and a sulfonyl halide to form a sulfonamide, an alcohol or phenol with an alkyl or aryl halide to form an ether, and the like.

The linker (or linkers) is attached to the ligand at a position such that the ligand domain is permitted to orient itself appropriately in order to bind to the ligand binding site. The term linker embraces everything that is not considered to be part of the ligand.

The relative orientation in which the ligand domains are displayed derives from the particular point or points of attachment of the ligands to the linker, and on the framework geometry. The determination of where acceptable substitutions can be made on a ligand is typically based on prior knowledge of structure-activity relationships of the ligand and/or congeners and/or structural information about ligand-receptor complexes (e.g., from X-ray crystallography, NMR). Such positions and the synthetic methods for covalent attachment are well known in the art.

Suitable linkers are discussed below.

At present, it is preferred that the multibinding agent is a bivalent compound, in which two ligands are covalently linked. For example, a glycopeptide bivalent compound may be constructed by linking any hydroxyl group, carboxyl group, "resorcinol" group [R], or amino group of a first glycopeptide ligand to any hydroxyl group, carboxyl group, "resorcinol" group [R], or amino group of a second glycopeptide. It should be noted that the term "hydroxyl group" includes a hydroxyl group obtained by reducing the carboxyl group at the [C] position to a hydroxymethyl group, as well as the hydroxyl groups on the sugars and on the peptide core structure.

"Increased biological effect" as used herein includes, but is not limited to, increased affinity, increased selectivity, increased potency, increased efficacy, increased duration of action, decreased toxicity, and the like.

The invention relates to multivalent compounds as defined above, comprising ligands that are binding partners for a transglycosylase enzyme substrate. The preferred ligands are optionally substituted glycopeptides, or their corresponding aglycones.

In the reaction schemes that follow, glycopeptides are depicted in a simplified form as a shaded box that shows only the carboxy terminus, labeled [C], the sugar amine terminus (for example, vancosamine), labeled [V], and the "non-sugar" amino terminus, labeled [N] (wherein such labels are shown, for example, in Formula II), as follows:

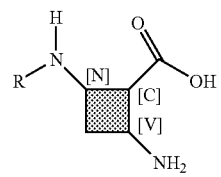

where R is hydrogen (as in N-desmethylvancomycin) or methyl (as in vancomycin).

It can therefore be seen by way of exemplification that one general class of multivalent compounds that fall within the scope of the definition of Formula I include compounds in which ligands, including optionally substituted ligands, are connected by one or more linkers X at the [C—C], [V—V], [N—N], [C—V], [C—N], and [V—N] termini.

Additionally, within the scope of the invention are the aglycone derivatives of glycopeptides. In the reaction schemes they are depicted as a shaded triangle that shows only the carboxyl terminus, labeled [C], the aglycone hydroxyl terminus, labeled [O], and the "non-sugar" amino terminus, labeled [N], (wherein such labels are shown, for example, in Formula II), as follows:

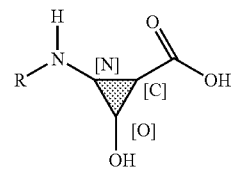

where R is hydrogen (as in N-desmethylvancomycin aglycone) or methyl (as in vancomycin aglycone).

It can therefore be seen by way of exemplification that another general class of multivalent compounds that fall within the scope of the definition of Formula I include those compounds in which 2–10 ligands are connected by one or more linkers X at the [C—C], [O—O], [N—N], [C—O], [C—N], and [O—N] termini.

Also within the scope of the invention are glycopeptides linked via their [C], [V], or [N] termini to aglycone derivatives of glycopeptides linked via their [C], [O], or [N] termini.

A third class of compounds falling within the scope of the invention are those in which the glycopeptides, or aglycone derivatives thereof, are linked via the [R] position. Reaction schemes that exemplify this linking strategy depict the ligands in a simplified form as above, i.e. as a shaded box in which the carboxyl terminus is labeled [C], the vancosamine amino terminus is labeled [V], and the "non-sugar" amino terminus is labeled [N], with the addition of the [R] position as a: resorcinol derivative (wherein such labels are shown, for example, in Formula II), as below:

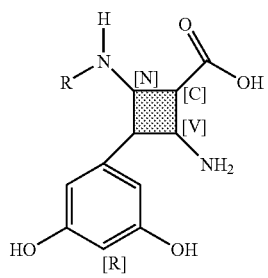

where R is hydrogen or methyl.

As previously described, glycopeptides are generally depicted in a simplified form as a shaded box that shows only the glycopeptide carboxyl terminus, labeled [C], the sugar amine (vancosamine in vancomycin) terminus, labeled [V], and the "non-sugar" amino terminus, labeled [N].

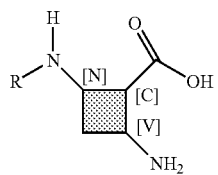

The preferred compounds of the invention are those represented by compounds of Formula I, $(L)_p X_q$, in which p is 2 and q is 1. The following nomenclature system will be used for naming the compounds of the invention and substituted ligands used in their preparation, using vancomycin as an example (Formula II), but it should be understood that all compounds of the invention may be named following these principles.

Substituted glycopeptides are within the scope of the definition of "ligand", and the point of substitution will be indicated as follows. For example, vancomycin substituted at the [C] terminus that has the formula:

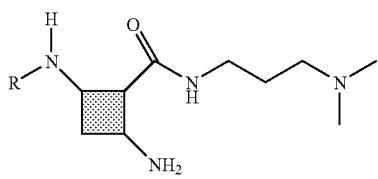

where R is methyl;

is named [C]-3-(dimethylamino)propylamino-(vancomycin).

It should be noted that although the linkage at the [C] terminus of the glycopeptide is an amide, the name is intended to indicate the linker only, i.e. it is named as an amine, not an amide. In this manner, confusion is avoided as to whether the glycopeptide terminal group (in this case [C]) is part of the linker as named.

For bivalent compounds, the positions at which the linking group connects to two vancomycin termini will be indicated as [C—C] when the links are joined to the carboxyl termini of both vancomycin molecules. Thus, a compound of the structure:

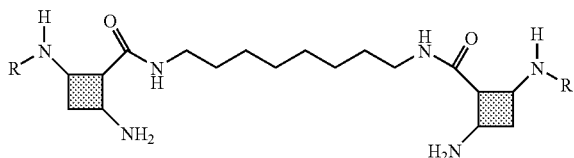

where R is methyl, represents two glycopeptides (vancomycin in this example) linked by a 1,8-diaminooctane group at the [C] positions of the glycopeptide. It will be named as:

[C—C]-octane-1,8-diamino-bis(vancomycin)

which indicates that two unsubstituted vancomycin molecules are linked by —NH—(CH$_2$)$_8$-NH—, each NH groups being attached to the carboxy termini of each vancomycin. As above, although the linkage at the [C] terminus of the glycopeptides is an amide, the name indicates the linker only, i.e. it is named as a diamine, not a diamide.

Similarly, [V—V]-heptan-1,7-dioyl-bis-(vancomycin) indicates that two unsubstituted vancomycin molecules are linked by —C(O)—(CH$_2$)$_5$—C(O)—, both C(O) groups being attached to the vancosamine (V) termini of each vancomycin, i.e. a compound of the structure:

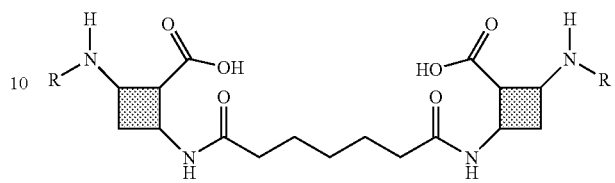

where R is methyl.

In the case where two unsubstituted vancomycin molecules are linked at two different termini, for example a [C] termini of a first vancomycin to a [V] termini of a second vancomycin with a linker of formula —NH—(CH$_2$)$_6$—CO—, i.e., a compound of the structure:

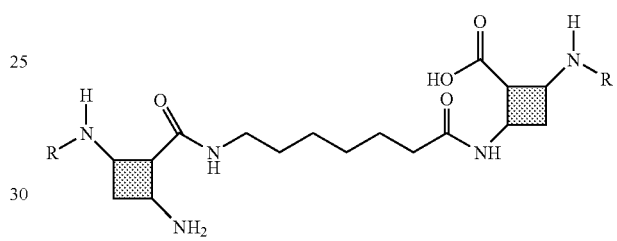

where R is methyl;

the compound is named [C—V]-1-aminoheptan-7-oyl-bis-(vancomycin).

Where an unsubstituted vancomycin molecule is linked to a vancomycin molecule that is substituted at the [C]-position, with a linker of formula —NH—(CH$_2$)$_6$—CO—, i.e., a compound of the structure:

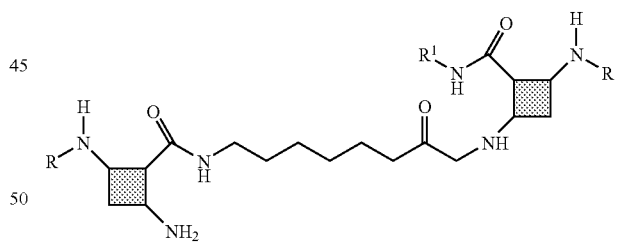

where R is methyl and R$^1$ is 3-(dimethylamino)propylamino;

is named (vancomycin) [C—V]-heptan-1-amino-7-oyl-([C]-3-(dimethylamino)propylamino-vancomycin).

Similarly, [N—N] indicates linking of two vancomycin molecules by the methylamino termini, [R—R] indicates linking of two vancomycin molecules by the "resorcinol" termini. [O—O] indicates that two aglycone molecules are linked by the phenolic hydroxy group that remains after hydrolysis of the sugar. [C—V] indicates that the [C] terminus of a first vancomycin is linked to the [V] terminus of a second vancomycin. Similar nomenclature applies to vancomycin linked [N—V], [C—O], [O—V], [C—R], and the like.

When both vancomycins are unsubstituted or identically substituted, the nomenclature will be as above, i.e. a compound designated as [V—V]-decan-1,10-dioyl bis -([C]-butylamino vancomycin) indicates that two vancomycin molecules, both of which are substituted at the [C] position by CH$_3$(CH$_2$)$_3$NH— are linked by —C(O)—(CH$_2$)$_8$—C(O)—, both C(O) termini being attached to the vancosamine (V) termini of each vancomycin. However, when both vancomycins are not identically substituted, for example a compound in which the first ligand is [C]-dimethylamino-vancomycin, and a second ligand is [C]-butylamino vancomycin), linked by —C(O)—(CH$_2$)$_8$—C(O)—, both C(O) termini being attached to the vancosamine (V) termini of each vancomycin, the compound is named:

([C]-dimethylamino-vancomycin) [V—V]-decan-1,10-dioyl-([C]-butylamino vancomycin).

Similarly, a compound in which the first ligand is [V]-octylvancomycin, and a second ligand is[C]-N-glucosamino-vancomycin, linked by

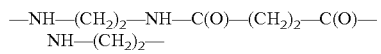

at the [C]-position of the first ligand to the [V]-position of the second ligand is named:

([V]-octylvancomycin)-[C—V]-butane-1,4-dioc acid (2-aminoethyl)-amide-(2-ethyl)-amide-([C]N-glucosamino-vancomycin).

Accordingly, a compound of Formula I wherein p is 2 and q is 1, and the ligands L are both vancomycin linked via their carbon [C] termini by:

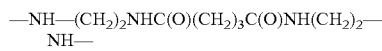

is named as:

[C—C]-[pentane-1,5-dioic acid bis-[(2-aminoethyl)-amide]-bis-(vancomycin)

A compound of Formula I wherein p is 2 and q is 1, and a first ligand is [V]-n-decylaminoethylvancomycin, and a second ligand is vancomycin, the ligands being linked via their carbon [C] termini by:

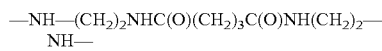

is named as:

([V]-n-decylaminoethylvancomycin)-[C—C]-[pentane-1,5-dioic acid bis-[(2-aminoethyl)-amide]-(vancomycin)

A compound of Formula I wherein p is 2 and the ligands L are both [V]-3-dimethylaminopropyl vancomycin linked via their carbon [C] termini by:

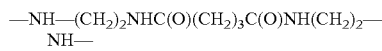

is named as:

[C—C]-[pentane-1,5-dioic acid bis-[(2-aminoethyl)-amide]-bis-([V]-3-(dimethyl-amino)propyl vancomycin)

A compound of Formula I wherein p is 2 and the ligands L are both vancomycin linked via their vancosoamine [V] termini by:

is named:

[V—V]-pentane-1,5-dioic acid-bis-[(2-ethyl)-amide]-bis-(vancomycin)

A compound of Formula I wherein p is 2 and one ligand L is vancomycin linked via its carbon [C] terminus and the second ligand L is vancomycin linked via its vancosoamine [V] terminus by:

is named:

[C—V]-pentane-1,5-dioic acid-[(2-aminoethyl)-amide]-[(2-ethyl)-amide]-bis(vancomycin).

A compound of Formula I wherein p is 2 and the ligands L are both vancomycin linked via their methylamino [N] termini by:

is named:

[N—N]-[pentane-1,5-dioic acid bis-[(2-ethyl)-amide] bis-(vancomycin)

A compound of Formula I wherein p is 2 and the first ligand L is vancomycin linked via its carbon [C] terminus and the second ligand L is vancomycin linked via its methylamino [N] terminus by:

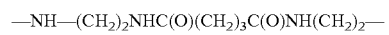

is named:

[C—N]-pentane-1,5-dioic acid-[(2-aminoethyl)-amide]-[(2-ethyl)-amide]-bis(vancomycin).

Utility

The multibinding agents of the invention, including the compounds of Formula I, and their pharmaceutically acceptable salts, are useful in medical treatments and exhibit biological activity, in particular antibacterial activity, which can be demonstrated in the tests described in the Examples. Such tests are well known to those skilled in the art, and are referenced and described in the fourth edition of "Antibiotics in Laboratory Medicine", by Victor Lorian, M.D., published by Williams and Wilkins, which is hereby incorporated by reference.

Pharmaceutical Compositions

Those compounds of the invention, including the compounds of Formula I, and their pharmaceutically acceptable salts that are active when given orally can be formulated as liquids for example syrups, suspensions or emulsions, tablets, capsules and lozenges.

A liquid composition will generally consist of a suspension or solution of the compound or pharmaceutically acceptable salt in a suitable liquid carrier(s), for example ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder.

For example a powder containing active compound, suspending agent, sucrose and a sweetener can be reconstituted with water to form a suspension; and a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example liquid paraffin or fractionated coconut oil can be prepared and filled into a soft gelatin capsule.

The compounds of the invention, including the compounds of Formula I, and their pharmaceutically acceptable salts that are active when given parenterally can be formulated for intramuscular, intrathecal, or intravenous administration.

A typical composition for intra-muscular or intrathecal administration will consist of a suspension or solution of active ingredient in an oil, for example arachis oil or sesame oil. A typical composition for intravenous or intrathecal administration will consist of a sterile isotonic aqueous solution containing, for example active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example polyethylene glycol, a chelating agent, for example ethylenediamine tetracetic acid, and an anti-oxidant, for example, sodium metabisulphite may be included in the formulation. Alternatively, the solution can be freeze dried and then reconstituted with a suitable solvent just prior to administration.

The compounds of the invention, including the compounds of Formula I, and their pharmaceutically acceptable salts which are active on rectal administration can be formulated as suppositories. A typical suppository formulation will generally consist of active ingredient with a binding and/or lubricating agent such as a gelatin or cocoa butter or other low melting vegetable or synthetic wax or fat.

Compounds of Formula I and their pharmaceutically acceptable salts which are active on topical administration can be formulated as transdermal compositions. Such compositions include, for example, a backing, active compound reservoir, a control membrane, liner and contact adhesive. The typical daily dose of a compound of Formula I varies according to individual needs, the condition to be treated and with the route of administration. Suitable doses are in the general range of from 0.01–100 mg/kg/day, preferably 0.1–50 mg/kg/day. For an average 70 kg human, this would amount to 0.7 mg to 7 g per day, or preferably 7 mg to 3.5 g per day.

One of ordinary skill in the art of treating such diseases will be able, without undue experimentation and in reliance upon personal knowledge and the disclosure of this application, to ascertain a therapeutically effective amount of the compounds of the invention, including the compounds of Formula I, for a given disease.

Methods of Preparation

Linker

The linker (or linkers), when covalently attached to multiple copies of the ligands, provides a biocompatible, substantially non-immunogenic multibinding agent. The biological effects of the multibinding agent are highly sensitive to the valency, geometry, composition, size, flexibility or rigidity, the presence or absence of anionic or cationic charge, and similar considerations (including hydrophilicity and hydrophobicity as discussed below) with respect to the linker. Accordingly, the linker is preferably chosen to maximize the desired biological effect. The linker may be biologically "neutral", i.e. not itself contribute any biological activity to the compound of Formula I, or it may be chosen to enhance the biological effect of the molecule. In general, the linker may be chosen from any organic molecule that orients two or more ligands to the receptors (enzymes or enzyme substrates), and permits multivalency. In this regard, the linker can be considered as a "framework" on which the ligands are arranged in order to bring about the desired ligand-orienting result, and thus produce a multibinding agent.

For example, different orientations can be achieved by including in the framework groups containing monocyclic or polycyclic groups, including aryl and heteroaryl groups, or structures incorporating one or more carbon—carbon multiple bonds (i.e., alkenes and alkynes). Other groups can also include oligomers and polymers which are branched- or straight-chain species. In preferred embodiments, rigidity is imparted by the presence of cyclic groups (e.g., aryl, heteroaryl, cycloalkyl, heterocycles, etc.). In other preferred embodiments, the ring is a six-or ten membered ring. In still further preferred embodiments, the ring is an aromatic group such as, for example, phenyl or naphthyl.

Different frameworks can be designed to provide preferred orientations of the ligands. Such frameworks may be represented by using an array of dots (as shown below) wherein each dot may potentially be an atom, such as C, O, N, S, P, H, F, Cl, Br, and F, or the dot may alternatively indicate the absence of an atom at that position. To facilitate the understanding of the framework structure, the framework is illustrated as a two dimensional array in the following diagram, although clearly the framework is a three dimensional array in practice:

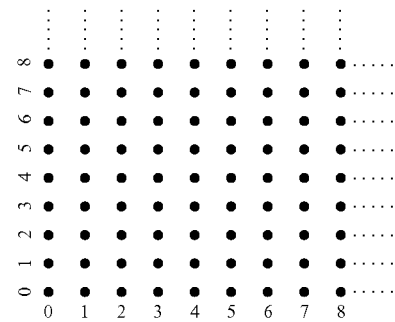

Each dot is either an atom, chosen from carbon, hydrogen, oxygen, nitrogen, sulfur, phosphorus, or halogen, or the dot represents a point in space (i.e. an absence of an atom). Only certain atoms on the grid have the ability to act as an attachment point for the ligands, namely C, O, N, S, and P.

Atoms can be connected to each other via bonds (single, double, or triple with acceptable resonance and tautomeric forms), with regard to the usual constraints of chemical bonding. Ligands may be attached to the framework via single, double, or triple bonds (with chemically acceptable tautomeric and resonance forms). Multiple ligand groups (2 to 10) can be attached to the framework such that the minimal, shortest path distance between adjacent ligand groups does not exceed 100 atoms or 40 angstroms.

The intersection of the framework (linker) and the ligand group, and indeed, the framework (linker) itself can have many different bonding patterns. Examples of acceptable patterns of three contiguous atom arrangements within the linker and at the linker-ligand interface are shown in the following diagram.

| | | | | |
|---|---|---|---|---|
| C C C | N C C | O C C | S C C | P C C |
| C C N | N C N | O C N | S C N | P C N |
| C C O | N C O | O C O | S C O | P C O |
| C C S | N C S | O C S | S C S | P C S |
| C C P | N C P | O C P | S C P | P C P |
| C N C | N N C | O N C | S N C | P N C |
| C N N | N N N | O N N | S N N | P N N |
| C N O | N N O | O N O | S N O | P N O |
| C N S | N N S | O N S | S N S | P N S |
| C N P | N N P | O N P | S N P | P N P |
| C O C | N O C | O O C | S O C | P O C |
| C O N | N O N | O O N | S O N | P O N |
| C O O | N O O | O O O | S O O | P O O |
| C O S | N O S | O O S | S O S | P O S |
| C O P | N O P | O O P | S O P | P O P |
| C S C | N S C | O S C | O S C | P S C |
| C S N | N S N | O S N | S S N | P S N |
| C S O | N S O | O S O | S S O | P S O |
| C S S | N S S | O S S | S S S | P S S |
| C S P | N S P | O S P | S S P | P S P |
| C P C | N P C | O P C | S P C | P P C |
| C P N | N P N | O P N | S P N | P P N |
| C P O | N P O | O P O | S P O | P P O |
| C P S | N P S | O P S | S P S | P P S |
| C P P | N P P | O P P | S P P | P P P |

One skilled in the art would be able to identify bonding patterns that would produce multivalent compounds. Methods for producing these bonding arrangements are described in "Advanced Organic Chemistry, 4$^{th}$ Edition" by March (Wiley-Interscience (New York), 1992). These arrangements are described in the grid of dots shown in the Scheme above. All of the possible arrangements for the five most preferred atoms are shown. Each atom has a variety of acceptable oxidation states. The bonding arrangements underlined are less acceptable and are not preferred.

Examples of molecular structures in which the above bonding patterns could be employed as components of the linker are shown below.

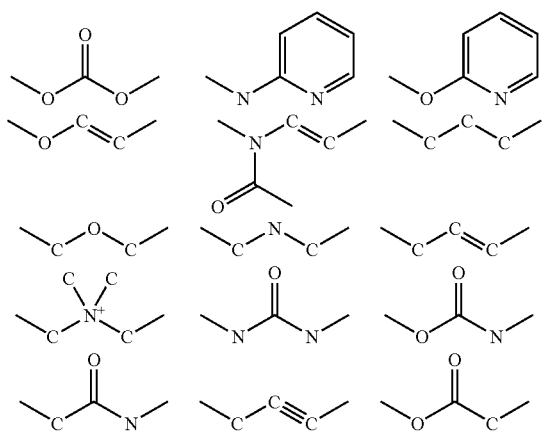

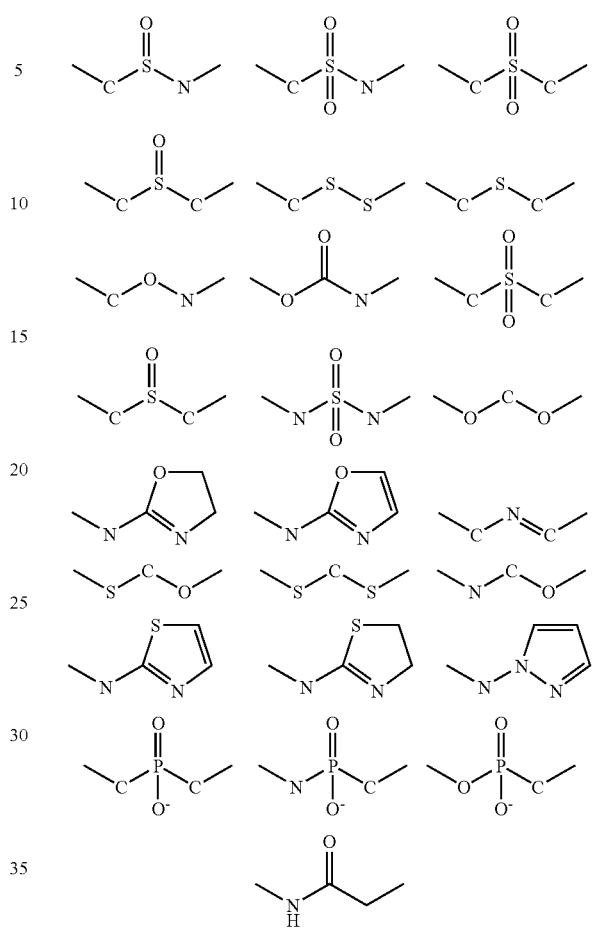

The identification of an appropriate framework geometry for ligand domain presentation is an important first step in the construction of a multivalent binding agent with enhanced activity. Systematic spatial searching strategies can be used to aid in the identification of preferred frameworks through an iterative process. Various strategies are known to those skilled in the art of molecular design and can be used for preparing the compounds of this invention.

For example, a bivalent compound can comprise ligands (represented as L) attached to central core structures such as those shown below.

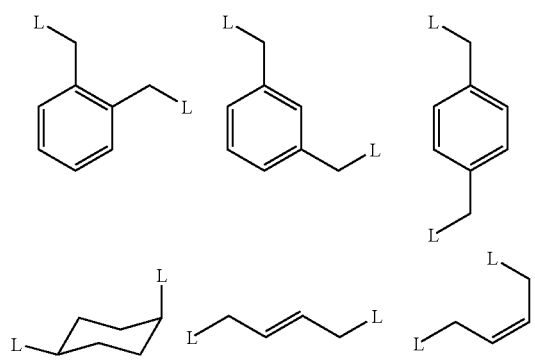

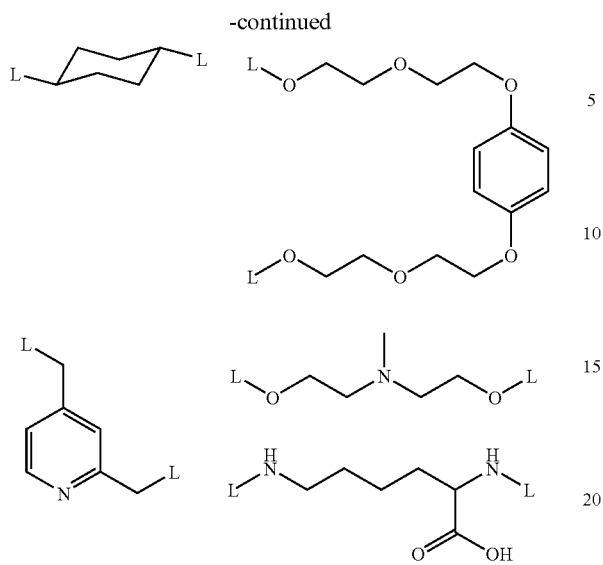

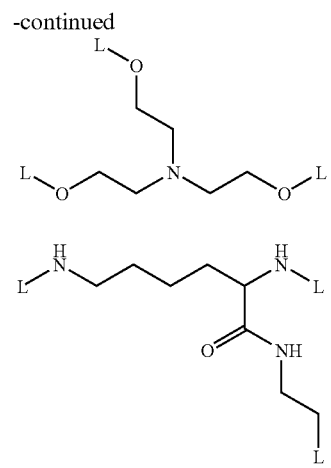

It is to be noted that core structures other than those shown here can be used for determining the optimal framework display orientation of the ligands. The process may require the use of multiple copies of the same central core structure or combinations of different types of display cores.

The above-described technique can be extended to trivalent compounds, as exemplified by structures shown below.

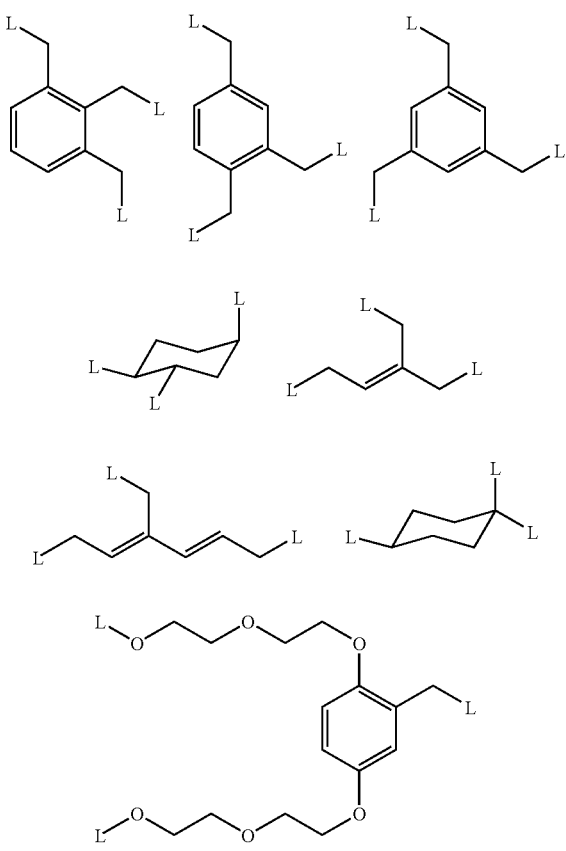

In the same manner, tetravalent and higher order structures can be prepared.

It can therefore be seen that there is a plethora of possibilities for the composition of a linker. Examples of linkers include aliphatic moieties, aromatic moieties, steroidal moieties, peptides, and the like. Specific examples are peptides or polyamides, hydrocarbons, aromatic groups, ethers, lipids, cationic or anionic groups, or a combination thereof, and many specific examples of linkers are shown below. However, it should be understood that various changes may be made and equivalents may be substituted without departing from the true spirit and scope of the invention. For example, properties of the linker can be modified by the addition or insertion of ancillary groups into the linker, for example, to change solubility of the multibinding agent (in water, fats, lipids, biological fluids, etc.), hydrophobicity, hydrophilicity, linker flexibility, antigenicity, molecular size, molecular weight, in vivo half-life, in vivo distribution, biocompatability, immunogenicity, stability, and the like. For example, the introduction of one or more poly or preferably oligo(ethylene glycol) (PEG) groups onto the linker enhances hydrophilicity and water solubility of the multibinding agent, increases both molecular weight and molecular size and, depending on the nature of the unPEGylated linker, may increase the in vivo retention time. Further, PEG may decrease antigenicity and potentially enhances the overall rigidity of the linker.

Ancillary groups that enhance the water solubility/hydrophilicity of the linker are useful in practicing the present invention. Thus, it is within the scope of the present invention to use ancillary groups such as, for example, poly (ethylene glycol), alcohols, polyols (e.g., glycerin, glycerol propoxylate, saccharides, including mono-, oligo- and polysaccharides, etc.), carboxylates, polycarboxylates (e.g., polyglutamic acid, polyacrylic acid, etc.), amines, polyamines (e.g., polylysine, poly(ethyleneimine), etc) to enhance the water solubility and/or hydrophilicity of the compounds of Formula I. In preferred embodiments, the ancillary group used to improve water solubility/hydrophilicity will be a polyether. In particularly preferred embodiments, the ancillary group will be a poly(ethylene glycol).

The incorporation of lipophilic ancillary groups within the structure of the linker to enhance the lipophilicity and/or hydrophobicity of the compounds of Formula I is within the scope of the present invention. Lipophilic groups of use in practicing the instant invention include, but are not limited to, aryl and heteroaryl groups. The aromatic groups may be either unsubstituted or substituted with other groups, but are at least substituted with a group which allows their covalent attachment to the linker. Other lipophilic groups of use in practicing the instant invention include fatty acid derivatives which do not form bilayers in aqueous medium until higher concentrations are reached.

Also within the scope of the present invention is the use of ancillary groups which result in the compound of Formula I being incorporated into a vesicle such as a liposome or a micelle. The term "lipid" refers to any fatty acid derivative that is capable of forming a bilayer or micelle such that a hydrophobic portion of the lipid material orients toward the bilayer while a hydrophilic portion orients toward the aqueous phase. Hydrophilic characteristics derive from the presence of phosphato, carboxylic, sulfato, amino, sulfhydryl, nitro, and other like groups. Hydrophobicity could be conferred by the inclusion of groups that include, but are not limited to, long chain saturated and unsaturated aliphatic hydrocarbon groups of up to 20 carbon atoms and such groups substituted by one or more aryl, heteroaryl, cycloalkyl and/or heterocyclic group(s). Preferred lipids are phosphoglycerides and sphingolipids, representative examples of which include phosphatidylcholine, phosphatidylethanolamine, phosphatidylserine, phosphatidylinositol, phosphatidic acid, palmitoyloleoyl phosphatidylcholine, lysophosphatidylcholine, lysophosphatidyl-ethanolamine, dipalmitoylphosphatidylcholine, dioleoylphosphatidylcholine, distearoyl-phosphatidylcholine or dilinoleoylphosphatidylcholine could be used. Other compounds lacking phosphorus, such as sphingolipid and glycosphingolipid families are also within the group designated as lipid. Additionally, the amphipathic lipids described above may be mixed with other lipids including triglycerides and sterols.

The flexibility of the linker can be reduced by the inclusion of ancillary groups which are bulky and/or rigid. The presence of bulky or rigid groups can hinder free rotation about bonds in the linker or bonds between the linker and the ancillary group(s) or bonds between the linker and the functional groups. Rigid groups can include, for example, those groups whose conformational lability is restrained by the presence of rings and/or multiple bonds, for example, aryl, heteroaryl, cycloalkyl, and/or heterocyclic. Other groups which can impart rigidity include polymeric groups such as oligo- or polyproline chains.

Rigidity can also be imparted electrostatically. Thus, if the ancillary groups are either negatively or positively charged, the similarly charged ancillary groups will force the presenter linker into a configuration affording the maximum distance between each of the like charges. The energetic cost of bringing the like-charged groups closer to each other will tend to hold the linker in a configuration that maintains the separation between the like-charged ancillary groups. Further, ancillary groups bearing opposite charges will tend to be attracted to their oppositely charged counterparts and potentially may enter into both inter- and intramolecular ionic bonds. This noncovalent bonding mechanism will tend to hold the linker into a conformation which allows bonding between the oppositely charged groups. The addition of ancillary groups which are charged, or alternatively, bear a latent charge which is unmasked, following addition to the linker, by deprotection, a change in pH, oxidation, reduction or other mechanisms known to those of skill in the art, is within the scope of the present invention.

Rigidity may also be imparted by internal hydrogen bonding, or by hydrophobic collapse.

Bulky groups can include, for example, large atoms and/or ions (e.g., iodine, sulfur, metal ions, etc.) groups containing large atoms, polycyclic groups, including aromatic groups, nonaromatic groups and structures incorporating one or more carbon—carbon multiple bonds (i.e., alkenes and alkynes). Bulky groups can also include oligomers and polymers which are branched- or straight-chain species. Species that are branched are expected to increase the rigidity of the structure more per unit molecular weight gain than are straight-chain species.

Eliminating or reducing antigenicity of the compounds of Formula I by judicious choice of ancillary group(s) is within the scope of the present invention. In certain applications, the antigenicity of a compound of Formula I may be reduced or eliminated by the use of groups such as, for example, poly(ethylene glycol).

As explained above, the multibinding agents of the invention comprise 2–10 ligands attached to a linker that connects the ligands in such a manner that they are presented to the enzyme multivalent receptors for multivalent interactions with the appropriate receptors (ligand binding site). The linker spatially constrains these interactions to occur within dimensions defined by the linker, thus increasing the biological effect of the multibinding agent as compared to the same number of individual units of the ligand.

The multivalent compounds of the invention, the compounds of Formula I, are represented by the empirical formula $(L)_p(X)_q$. This is intended to include the several ways in which the ligands can be linked together in order to achieve the objective of multivalency, and a more detailed explanation is given below. However, as previously noted, the linker can be considered as a framework, and it should be understood that the ligands can be attached to this framework at any intermediate point on the framework, and/or on the termini of the framework. For example, if the linker is a linear chain, a bivalent compound can be constructed by attaching two ligands at the two ends of the linear chain, or alternatively attaching two ligands at some intermediate atom along the chain. The same considerations apply to the compounds of the present invention containing more than 2 ligands.

The simplest (and preferred) multibinding agent is a bivalent compound, which can be represented as L—X—L, where L is a ligand and is the same or different, and X is the linker. It should be noted that the linker X can be linear or cyclic, or a combination of both linear and cyclic constructs, and that the two ligands may be located at the termini of the linker or may be attached at some intermediate attachment point. The same is true for a trivalent compound, which can also be represented in a linear fashion, i.e. as a sequence of repeated units L—X—L—X—L, in which L is a ligand and is the same or different at each occurrence, as can X, or a compound comprising three ligands attached to a central core, and thus represented as $(L)_3X$, where the linker X could include, for example, an aryl or cycloalkyl group.

The same considerations of geometry apply to the compounds of the present invention containing 4–10 ligands. For example, a tetravalent compound could be represented as

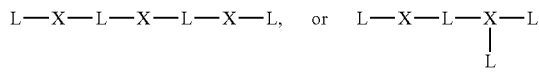

i.e. a branched construct analogous to the isomers of butane (n-butyl, sec-butyl, tert-butyl). Alternatively, it could be represented as an aryl or cycloalkyl derivative as above with four ligands attached to the core linker. The same principles apply to the higher multibinding agents, e.g. pentavalent to decavalent compounds. However, for multibinding agents attached to a central linker such as benzene, there is the self-evident constraint that there must be sufficient attachment sites on the linking moiety to accommodate the number of ligands present; for example, a benzene ring could not accommodate more than six ligands, whereas a saturated and/or multi-ring linker (cyclohexyl, cyclooctyl, biphenyl, etc.) could accommodate a larger number of ligands.

The formula $(L)_p(X)_q$ is also intended to represent a cyclic compound of formula

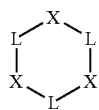

$(-L-X-)_n$, where n is 2–10. For example, where n is 3:

All of the above variations are intended to be within the scope of the invention as defined by the Formula I $(L)_p(X)_q$.

The preferred linker length will vary depending upon the distance between adjacent ligand recognition sites, and the geometry, flexibility and composition of the linker. The length of the linker will preferably be in the range of about 2–100 Angstroms, more preferably about 2–50 Angstroms, and even more preferably about 5–20 Angstroms.

With the foregoing in mind, preferred linkers may be represented by the following formula:

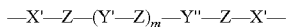

in which:

m is an integer of 0–20;

X' at each separate occurrence is —O—, —S—, —S(O)—, —S(O)$_2$—, —NR— (where R is as defined below), —C(O)—, or a covalent bond;

Z at each separate occurrence is alkylene, cycloalkylene, alkenylene, alkynylene, arylene, heteroarylene, or a covalent bond;

Y' and Y" at each separate occurrence are

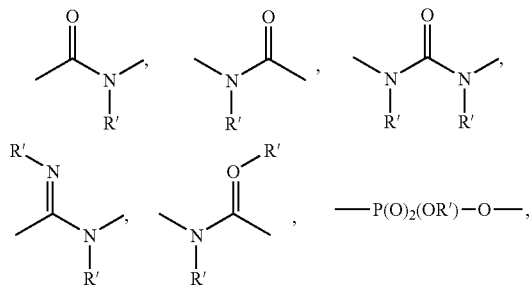

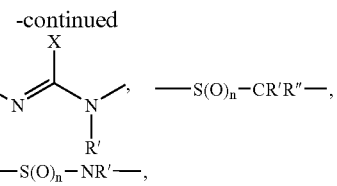

—S—S—, or a covalent bond;

in which:

n is 0, 1 or 2; and

R, R' and R" at each separate occurrence are chosen from hydrogen, alkyl, cycloalkyl, alkenyl, cycloalkenyl, alkynyl, aryl, heteroaryl, and heterocyclo.

Additionally, the linker moiety can be optionally substituted at any atom in the chain by alkyl, cycloalkyl, alkenyl, alkynyl, alkoxy, halo, nitro, aryl, heteroaryl, or heterocyclo.

Preparation of Compounds of Formula I

The preferred compounds of the invention are those in which p is 2 and q is 1, and for the sake of simplicity the following description is directed toward the preparation of such compounds. However, it should be understood that the same synthetic principles can be applied to all compounds within the scope of the invention.

There are many ways in which to prepare the compounds of the invention. However, there are three basic themes common to their preparation;

1) Preparation of a substituted ligand (as defined above) at the [C] terminus, the [V] terminus, the [N] terminus, the [0] terminus, and/or the [R] terminus for use in coupling reactions;
2) Preparation of a bivalent compound of the invention by coupling two ligands (the same or different, unsubstituted or substituted) with an appropriate linker at the above mentioned termini;
3) Preparation of an intermediate of a ligand having a functional group that can then be further reacted with an appropriate linker or ligand intermediate to form a compound of the invention.

Examples of these reactions are given below. Given that there is a carboxylic acid terminus [C], a primary amine terminus [V], and a secondary amine terminus [N] available on the glycopeptide ligands for linking reactions, one of the most general reactions used for this purpose is that between a carboxylic acid and an amine to form an amide. For example, as shown in FIG. 1, Reactions A and B, a carboxylic acid, for example that is available at the [C] terminus, can be reacted directly with an amine to form an monoamide, or with a diamine to form a compound of the invention. However, it is also possible to react the carboxylic acid in a manner that produces an intermediate capable of undergoing further reaction, for example an amino or carboxy functional group (Reactions C and D), a hydroxy group, and the like, which can be used to react further with an appropriate linker, for example a dicarboxylic acid or diamine, to form a compound of the invention.

Other possible reactions include modification of the amine terminus by reductive alkylation, formation of an amidine link, and the like.

It should be understood that the shaded circle in the Figures and Reaction Schemes represents, for the sake of simplicity, the "core" of a linker. That is to say, a shaded circle showing two attached amino groups (formula (2)) represents any diamino compound that can be used in a coupling reaction, for example 1,6-diaminohexane, 1,2-bis-(aminomethyl)phenyl, 1,4-bis-(aminomethyl)cyclohexane, and the like. A complete list of commercially available diamines is available on the ACD catalogue. In FIG. 1, A represents a ligand or substituted ligand to which a carboxylic acid is attached, PG is a protecting group, and the shaded circle represents a linker "core". It will be apparent to one of skill in the art that secondary amines can also be used in place of the primary —NH$_2$ or —NHPG groups shown above.

Figure 2:
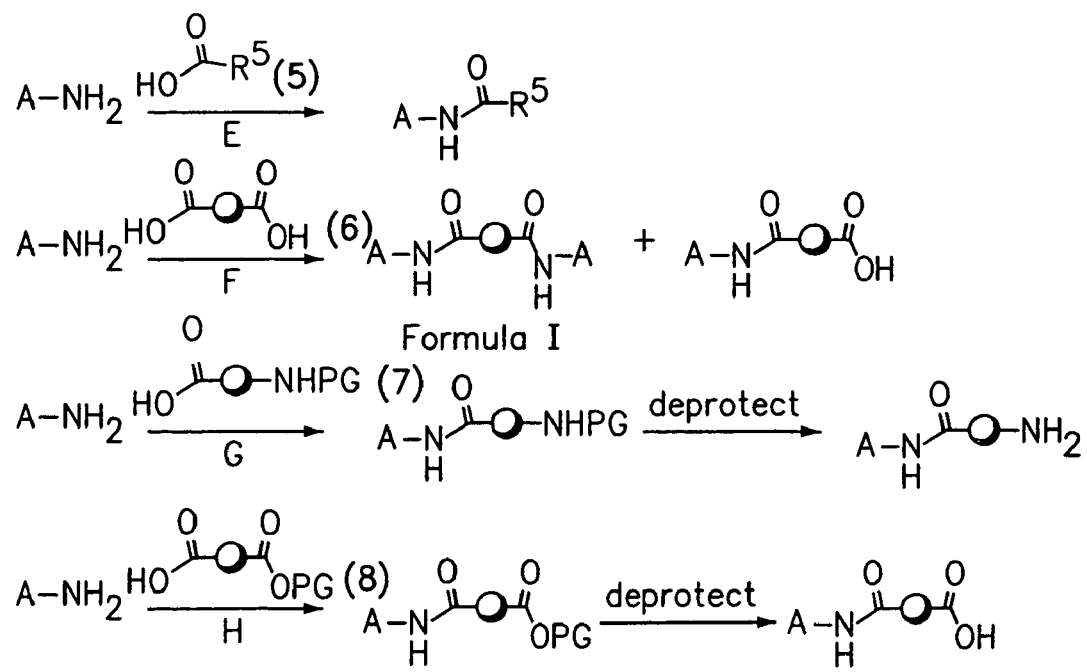
FIG. 2 illustrates the synthesis of a compound of formula I and intermediates thereof using an amine compound and a carboxylic acid or a dicarboxylic acid compound.

Similarly, FIG. 2 shows reaction of an amine, for example the [V] or [N] terminus, with a carboxylic acid or dicarboxylic acid to form an amide or diamide. The amine can also be reacted to produce a protected intermediate with a second amino group or carboxy functional group, which can be reacted further with a dicarboxylic acid or diamine in order to produce a compound of the invention.

It should be noted that in reactions where a carboxylic acid is shown as the reactant, the equivalent acid chloride can be used in its place. In FIG. 2, A represents a ligand or substituted ligand to which an amino group is attached, PG is a protecting group, and the shaded circle represents a linker "core".

Figure 3:
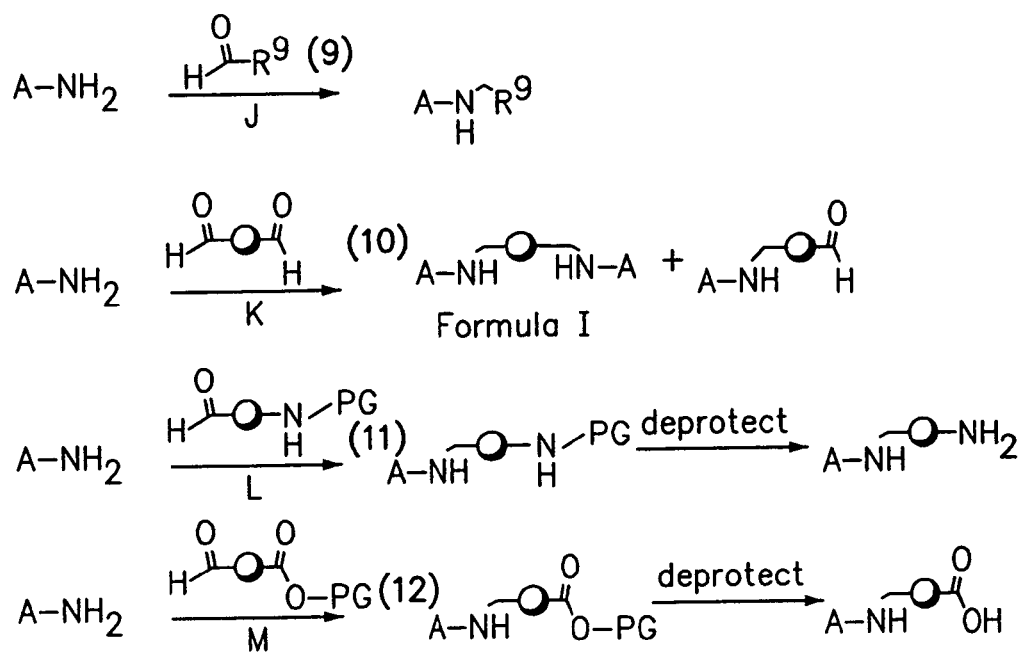
FIG. 3 illustrates the synthesis of a compound of formula I and intermediates thereof using an amine compound and an aldehyde or dialdehyde compound.

In FIG. 3, an amine, for example the [V] or [N] termini, can be derivatized by a reductive alkylation reaction with an aldehyde to form an alkyl substituent, or reacted with a dialdehyde under reductive alkylation conditions to give a compound of the invention. Reaction with appropriately protected aldehydes or carboxylic acids gives an intermediate with an amino or carboxy functional group (Reactions L and M), the products of which can be used to react further with a carboxylic acid or amine respectively to form an amide. In FIG. 3, A represents a ligand or substituted ligand to which an amino group acid is attached, PG is a protecting group, and the shaded circle represents a linker "core".

Figure 4:
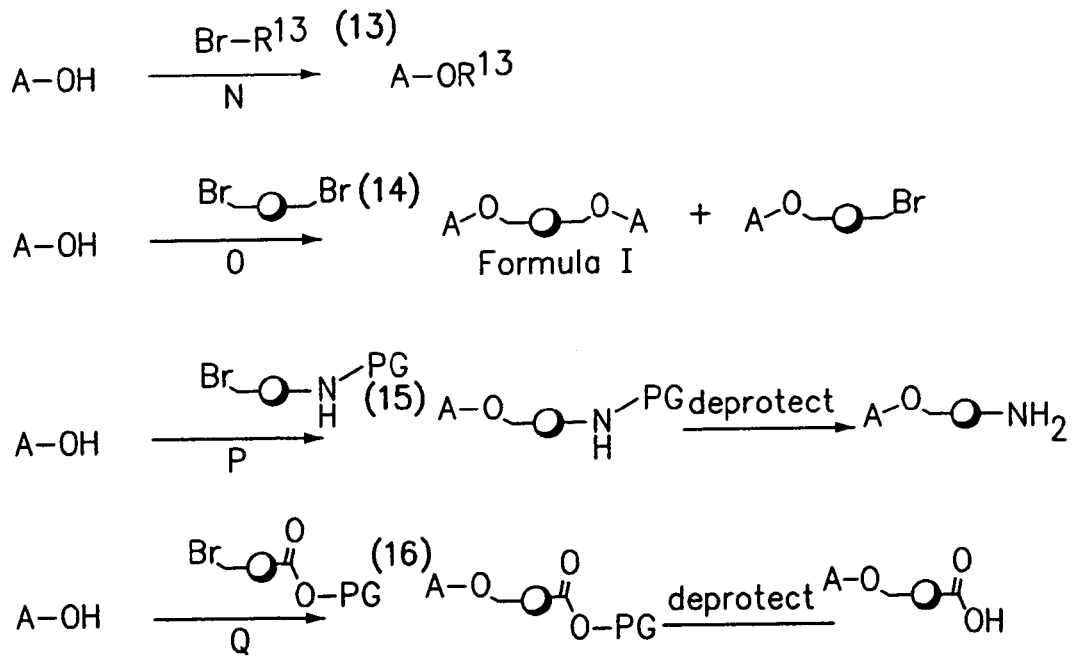
FIG. 4 illustrates the synthesis of a compound of formula I and intermediates thereof using a hydroxy compound and a mono- or dibromo compound.

FIG. 4 similarly shows the derivatization of a hydroxy group, for example the aglycone hydroxy group designated as [O]. In FIG. 4, A represents a ligand or substituted ligand to which a hydroxy group is attached, PG is a protecting group, and the shaded circle represents a linker "core".

Figure 5:
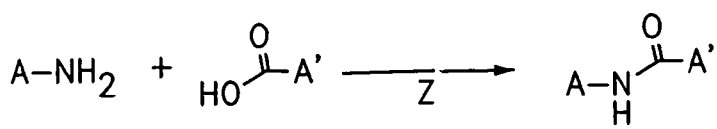
FIG. 5 illustrates the synthesis of an unsymmetrical compound of the invention.

FIG. 5 shows the preparation of unsymmetrical compounds of the invention, by reaction of those products described above having amino and carboxyl functional groups.

Preparation of Starting Materials

The diamines of formula (2) used as coupling reagents in FIG. 1 are either commercially available or are prepared by methods well known in the art. One example of such a preparation is shown below in Reaction Scheme 1. It should be noted that the following reaction schemes are presented for illustrative purposes, and accordingly are shown in simplified form.

Accordingly, diamines of Formula (19) may be prepared as shown below in Reaction Scheme 1.

REACTION SCHEME 1

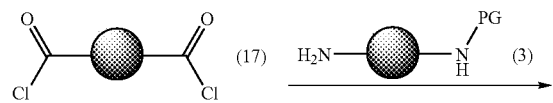

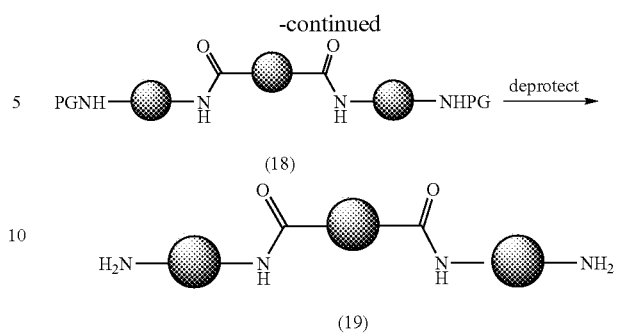

where PG is a protecting group, preferably t-butyl carbamate, and the shaded circle represents a linker core Preparation of Compounds of Formula (18)

As illustrated in Reaction Scheme 1, step 1, about two molar equivalents of an omega-amino carbamic acid ester [formula (3)] reacted with about one molar equivalent of a dicarboxylic acid halide, preferably chloride, of formula (17). The reaction is conducted in the presence of a hindered base, preferably diisopropylethylamine, in an inert solvent, preferably methylene chloride, at a temperature of about 0–5° C. The mixture is then allowed to warm to room temperature. When the reaction is substantially complete, the compound of formula (18) is isolated and purified by conventional means.

Preparation of Compounds of Formula (19)

As illustrated in Reaction Scheme 1, step 2, the carbamate protecting group is hydrolyzed under acid conditions. In general a preferred acid is trifluoroacetic acid. The reaction is conducted in an inert solvent, preferably methylene chloride, at about room temperature. When the reaction is substantially complete, the compound of formula (19), which is a compound of formula (2) is isolated and purified by conventional means.

The linking groups used as coupling reagents in the figures above are either commercially available or are prepared by methods well known in the art. Several examples of such a preparation are shown below in Reaction Scheme 2–3. Reaction Scheme 2 shows the preparation of an aminoaldehyde from the corresponding aminoalcohol.

REACTION SCHEME 2

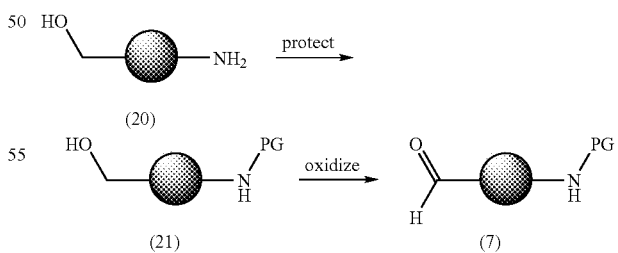

where PG is a protecting group, preferably 9-fluorenylmethoxycarbonyl.

Preparation of a Compound of Formula (7)

Illustrated in Reaction Scheme 2 is a method for preparing a protected-aminoaldehyde (7) from the corresponding aminoalcohol (20). The aminoalcohol is protected by conventional technique, for example, by treatment with 9-fluorenylmethyl chloroformate in the presence of base, to yield Fmoc protected aminoalcohol (21). Oxidation by techniques well known in the art (for example, TEMPO, or sulfur trioxide/pyridine) yields an aldehyde of formula (7).

Similarly, Reaction Scheme 3 shows other methods by which derivatives of aldehydes are prepared.

REACTION SCHEME 3

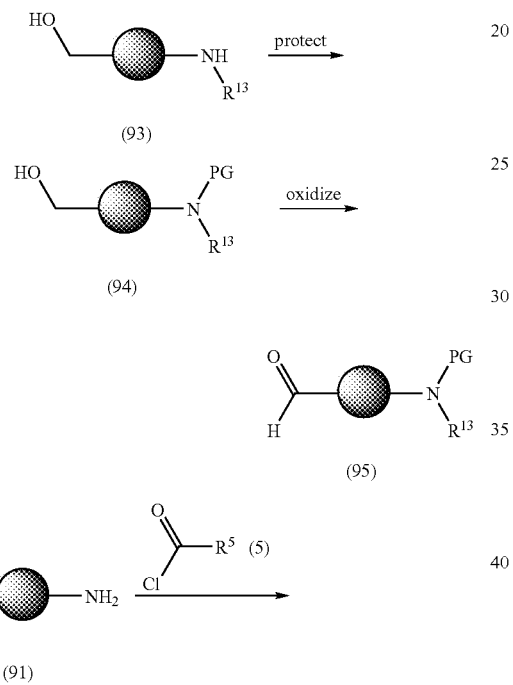

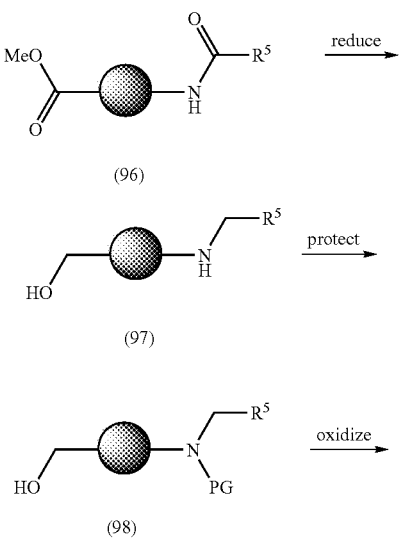

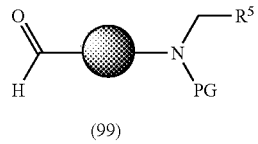

where PG is a protecting group, $R^5$ is hydrogen, alkyl, aryl, heteroaryl, arylalkyl, or heteroarylalkyl, and $R^{13}$ is alkyl, arylalkyl, or heteroarylalkyl, Reaction Scheme 4 shows one method by which a [C—C] bivalent compound can be made. Also produced is a monomer of formula (22).

REACTION SCHEME 4

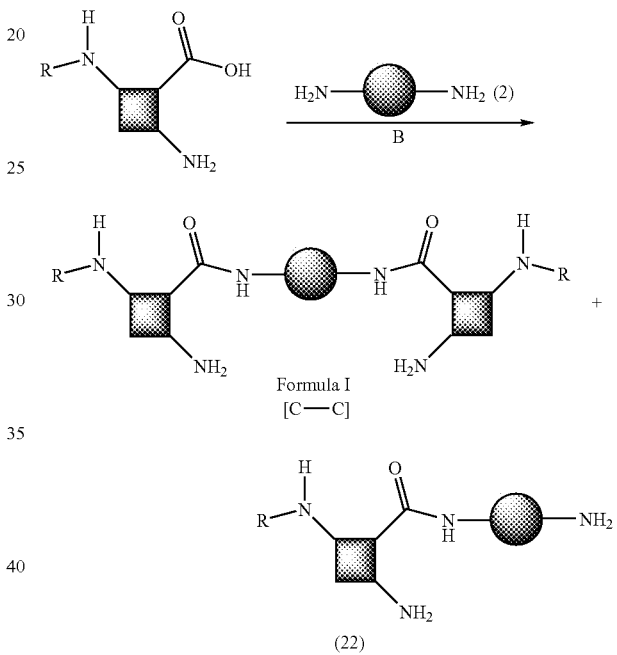

where R is hydrogen or methyl, and the shaded circle is a linker "core".

Preparation of a [C—C] Linked Compound of Formula I

In general, about two molar equivalents of a glycopeptide, for example vancomycin, are reacted with about one molar equivalent of the diamine of general formula (2) (for example, a diamine of formula (19)), under conventional amide coupling conditions. Preferably, a hindered base is employed, preferably diisopropylethylamine, in the presence of benzotriazol-1 yloxytripyrrolidinophosphonium hexafluorophosphate (PyBOP) and 1-hydroxybenzotriazole. The reaction is conducted in an inert polar solvent, for example N,N-dimethylformamide (DMF) or dimethyl sulfoxide (DMSO), or preferably a mixture of both, at about room temperature. When the reaction is substantially complete, the compound of Formula I is isolated and purified by conventional means, preferably purified by reverse-phase HPLC. Also isolated is the monoadduct, a compound of formula (22).

Alternatively, an intermediate of formula (22) may be prepared as shown below in Reaction Scheme 5, and used to prepare a [C—C] compound of Formula I.

REACTION SCHEME 5
Preparation of a [C—C] Linked Compound of Formula I

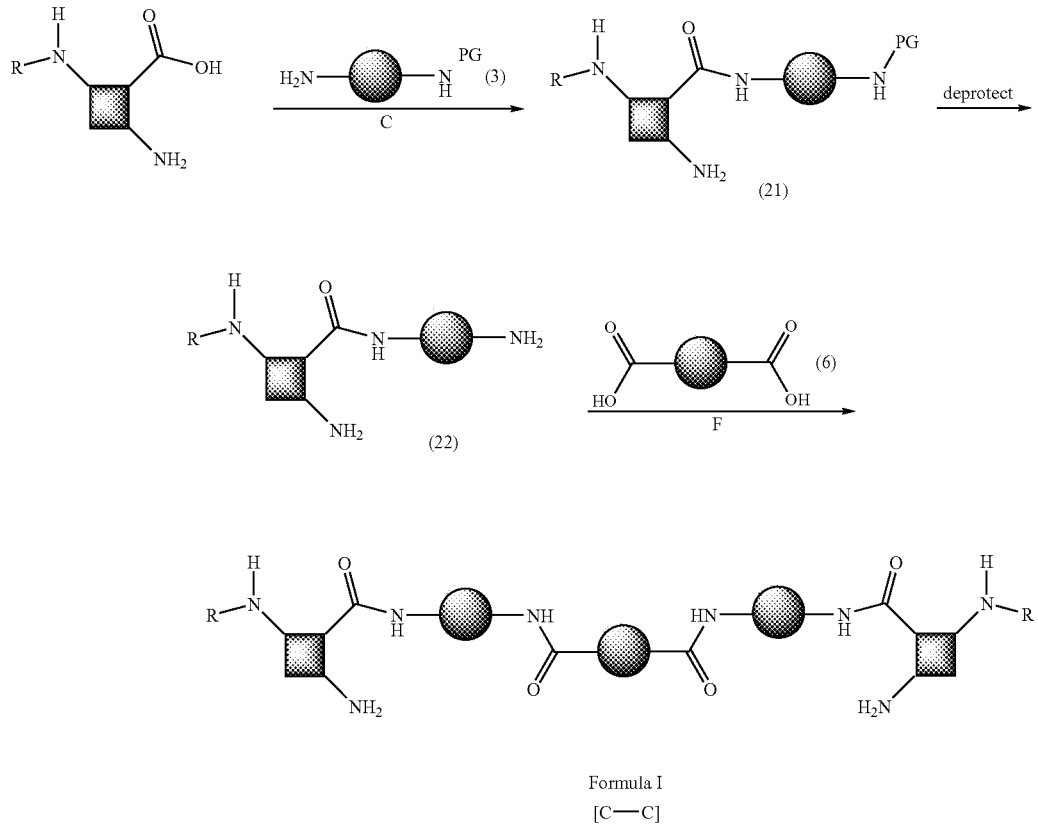

Formula I
[C—C]

where R is hydrogen or methyl, and PG represents a protecting group, preferably 9-fluorenylmethoxycarbonyl.

Preparation of a Compound of Formula (21)

As illustrated in Reaction Scheme 5, step 1, a glycopeptide, for example vancomycin, is reacted with about 1.1 molar equivalents of a carbamic ester terminated by an alkylamino group [formula (3)]. The ester moiety is chosen for ease of removal under mild conditions in subsequent reactions, and is preferably 9-fluorenylmethyl. Conventional amide coupling conditions are employed, preferably using PyBOP and 1-hydroxybenzotriazole. In general, the reaction is conducted in the presence of a hindered base, preferably diisopropylethylamine, in an inert polar solvent, preferably DMF or DMSO, preferably a mixture of both, at about room temperature. When the reaction is substantially complete, the compound of formula (21) is isolated and purified by conventional means.

Preparation of Compounds of Formula (22)

As illustrated in Reaction Scheme 5, step 2, the compound of formula (21) is reacted with a mild base to remove the protecting ester group, which also affords decarboxylation. In general, the base is preferably piperidine, and the reaction is conducted in an inert polar solvent, preferably dimethylformamide, at about room temperature for about 10 minutes to one hour. When the reaction is substantially complete, the compound of formula (22) is isolated and purified by conventional means, preferably using reverse-phase HPLC.

The intermediate of formula (22) may then be converted into a [C—C] glycopeptide bivalent compound.

Preparation of a Compound of Formula I

As illustrated in Reaction Scheme 5, step 3, the compound of formula (22) is reacted with a dicarboxylic acid. In general, about 3 molar equivalents of the compound of formula (22) is reacted with about 1 molar equivalent of the dicarboxylic acid of formula (6), under conventional amide coupling conditions. Preferably, a hindered base is employed, preferably diisopropylethylamine, in the presence of PyBOP and 1-hydroxybenzotriazole. The reaction is conducted in an inert polar solvent, preferably DMF, at about room temperature for about 1–3 hours. When the reaction is substantially complete, the compound of Formula I is isolated and purified by conventional means, preferably by reverse-phase HPLC.

In addition to coupling two ligands of formula (22) with a dicarboxylic acid, the [C—C] compounds of the invention can also be prepared by bis reductive alkylation of (22) with a dialdehyde.

It should also be understood that although. Reaction Scheme 5 shows unsubstituted glycopeptides as the ligand for reaction, the same reaction is possible starting with a glycopeptide substituted (or protected) at the [V] position. The [V] amino group can then be further modified in later steps if desired.

Compounds of Formula I wherein the linkage is [C—C] in which the [V] position is substituted may be prepared from intermediates of formula (25), the preparation of which is shown below in Reaction Scheme 6.

REACTION SCHEME 6
Preparation of a [C—C] Linked Compound of Formula I

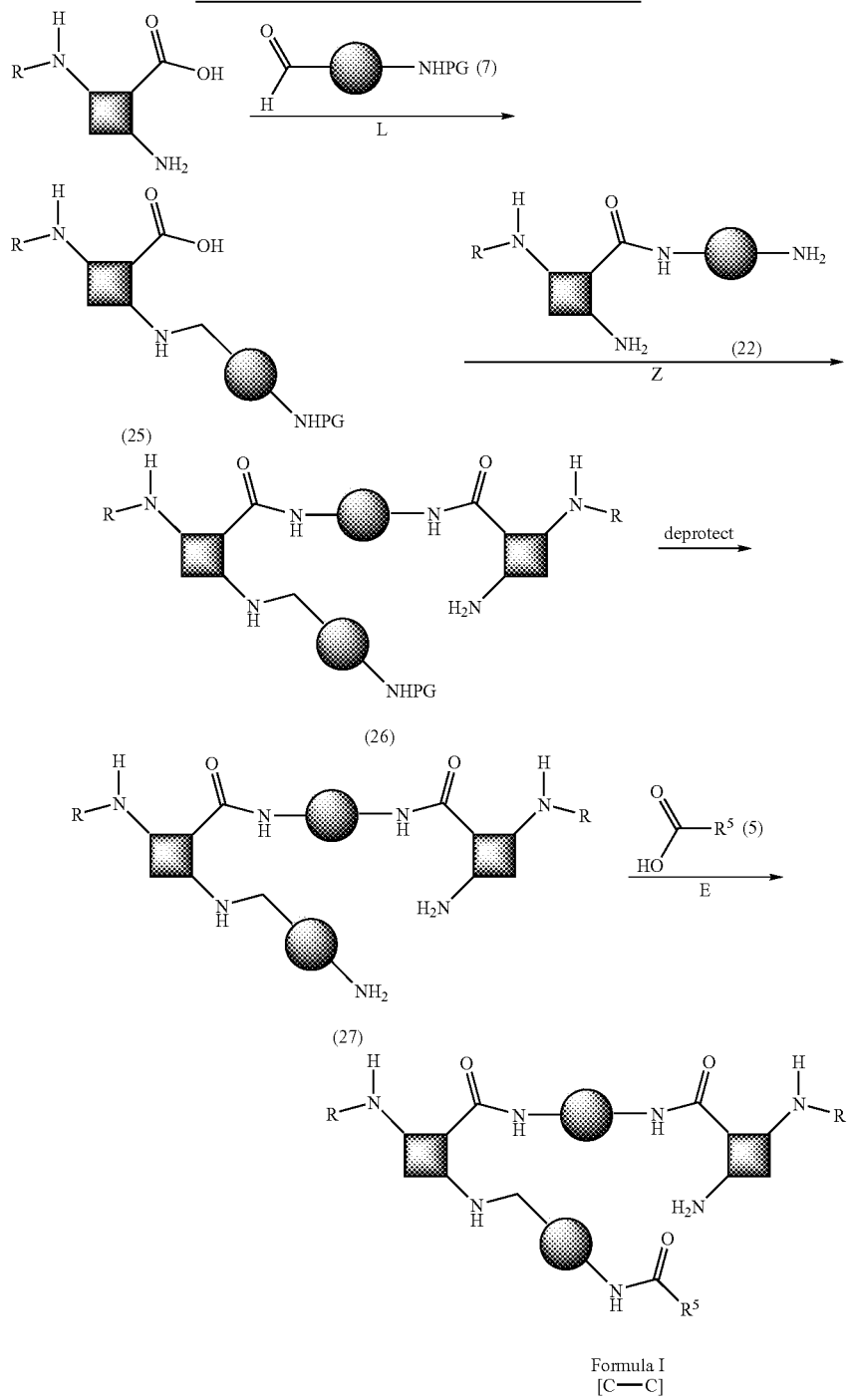

where R is hydrogen or methyl, PG represents a protecting group, preferably 9-fluorenylmethoxycarbonyl, and $R^5$ is alkyl, aryl, heteroaryl, arylalkyl, or heteroarylalkyl, all of which may be optionally substituted.

Preparation of a Compound Formula (25)

As illustrated in Reaction Scheme 6, step 1, the amino sugar moiety of the glycopeptide, for example the vancosamine portion of vancomycin, is reacted with a protected amino-aldehyde of formula (7) to form a Schiff's base. The ester moiety is chosen for ease of removal under mild conditions in subsequent reactions, and is preferably 9-fluorenylmethoxycarbonyl (Fmoc). In general, the reaction is conducted in an inert polar solvent, preferably N,N-dimethylformamide, at about 0–50° C., in the presence of a hindered base, preferably N,N-diisopropylethylamine, preferably about 25° C., for about 1–5 hours, preferably about 2 hours. The Schiff's base is further reacted with a mild reducing agent. In general, a protic solvent is added, preferably methanol, followed by the reducing agent, preferably sodium cyanoborohydride, and then trifluoroacetic acid. The reaction is conducted at about 0–50° C., preferably about 25° C., for about 1 hour. When the reaction is substantially complete, the compound of formula (25) is isolated and purified by conventional means, preferably purified by reverse-phase HPLC. It should be noted that other intermediates can be used in place of the compound of formula (7), for example a protected acid (to give an amide), or an alkyl or aryl group can be appended directly on the [V] amine.

The intermediate of formula (25) may then be converted into a [C—C] vancomycin bivalent compound in which the [V] position is also substituted.

$R^5$—$CO_2H$ or $R^5$—COCl, in which $R^5$ is alkyl, aryl, heteroaryl, arylalkyl, heteroarylalkyl, all of which may be optionally substituted. In general, conventional amide coupling conditions are employed. Preferably, a hindered base is used, preferably diisopropylethylamine, in the presence of PyBOP and 1-hydroxybenzotriazole. The reaction is conducted in an inert polar solvent, preferably DMF, at about room temperature for about 1–3 hours. When the reaction is substantially complete, the compound of Formula I is isolated and purified by conventional means, preferably purified by reverse-phase HPLC.

It should be noted that both the compounds of formula (26) and (27) can also be considered as compounds of Formula I. Additionally, step 4 can be any reaction that gives a substituted derivative of the amine group; for example, reductive alkylation, alkylation, and the like.

REACTION SCHEME 7
Preparation of a [C—C] Linked Compound of Formula I

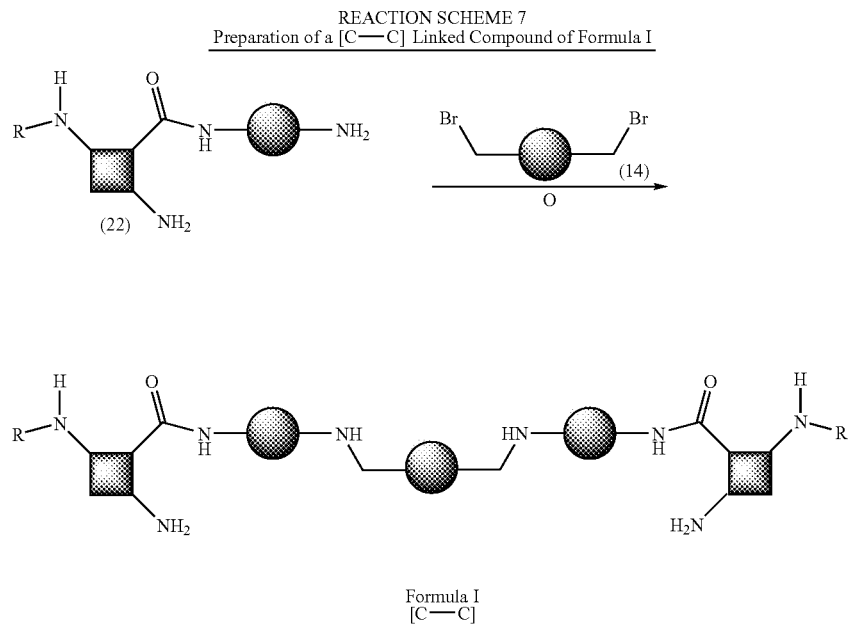

Formula I
[C—C]

Preparation of a Compound of Formula (26)

As illustrated in Reaction Scheme 6, step 2, the compound of formula (25) is reacted with a compound of formula (22), which may be prepared as shown in Reaction Scheme 4. In general, conventional amide coupling conditions are employed. Preferably, a hindered base is used, preferably diisopropylethylamine, in the presence of PyBOP and 1-hydroxybenzotriazole. The reaction is conducted in an inert polar solvent, preferably DMF, at about room temperature for about 1–3 hours. When the reaction is substantially complete, the compound of formula (26) is isolated and purified by conventional means, preferably purified by reverse-phase HPLC.

Preparation of a Compound of Formula (27)

As illustrated in Reaction Scheme 6, step 3, the compound of formula (26) is deprotected conventionally as shown above, for example in Reaction Scheme 5, step 2, to form a compound of formula (27).

Preparation of Compounds of Formula I

As illustrated in Reaction Scheme 6, step 4, the compound of formula (27) is reacted with a compound of formula where R is hydrogen or methyl.

Preparation of a Compound of Formula I

In general, about two molar equivalents of a compound of Formula (22) are reacted with about one molar equivalent of the dialkylhalide of general formula (14) under conventional alkylation conditions, in the presence of a hindered base, preferably diisopropylethylamine. The reaction is conducted in an inert polar solvent, for example N,N-dimethylformamide (DMF), at about 40–100° C., for about 1–24 hours, preferably about 8 hours. When the reaction is substantially complete, the compound of Formula I is isolated and purified by conventional means, preferably purified by reverse-phase HPLC.

This reaction is, of course, broadly aplicable to any ligand that contains a free amine group.

REACTION SCHEME 8
Preparation of a [V—V] Linked Compound of Formula I

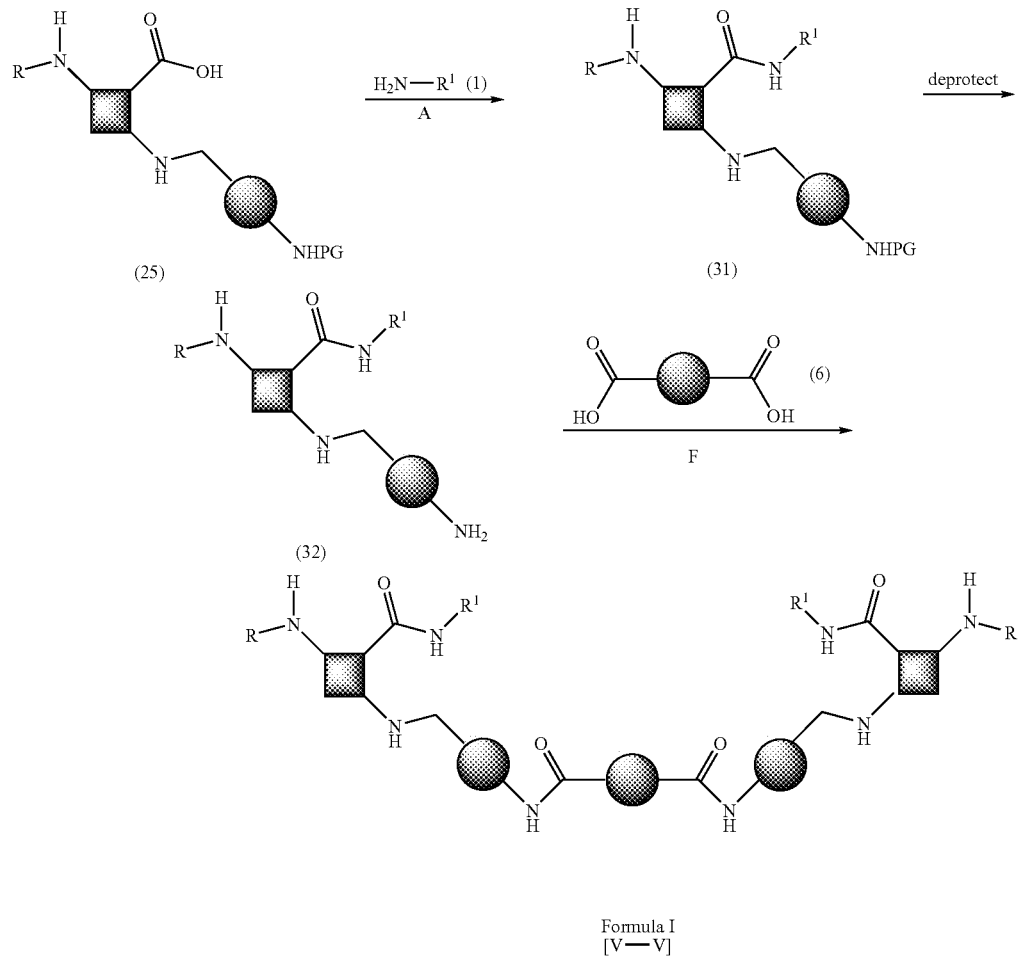

Formula I
[V—V]

where R is hydrogen or methyl, PG represents a protecting group, preferably 9-fluorenylmethoxycarbonyl, and $R^1$ is, alkyl, aminoalkyl, alkylaminoalkyl, aryl, heteroaryl, arylalkyl, heteroarylalkyl, or a quarternary salt derivative.

Preparation of a Compound of Formula (31)

As illustrated in Reaction Scheme 8, step 1, the carboxyl function of the compound of formula (25) is reacted with an amine of formula (1). In general, about 1 molar equivalent of the compound of formula (25) is reacted with about 1.5 molar equivalents of (1) under conventional amide coupling conditions. Preferably, a hindered base is employed, preferably diisopropylethylamine, in the presence of PyBOP and 1-hydroxybenzotriazole. The reaction is conducted in an inert polar solvent, preferably DMF, at about room temperature for about 10 minutes to 2 hours. When the reaction is substantially complete, the compound of formula (31) is isolated and purified by conventional means, preferably by reverse-phase HPLC.

Preparation of a Compound of Formula (32)

As illustrated in Reaction Scheme 8, step 2, the compound of formula (31) is deprotected conventionally as shown above, for example in Reaction Scheme 5, step 2, to form a compound of formula (32).

The intermediate of formula (32) is then converted into a [V—V] glycopeptide bivalent compound in which the [C] position is also substituted, as shown below.

Preparation of Compounds of Formula I

As illustrated in Reaction Scheme 8, step 3, the compound of formula (32) is reacted with a dicarboxylic acid (6). In general, about 3 molar equivalents of the compound of formula (32) is reacted with about 1 molar equivalent of the dicarboxylic acid of formula (6), under conventional amide coupling conditions. Preferably, a hindered base is employed, preferably diisopropylethylamine, in the presence of PyBOP and 1-hydroxybenzotriazole. The reaction is conducted in an inert polar solvent, preferably DMF, at about room temperature for about 1–3 hours. When the reaction is substantially complete and the compound of Formula I is isolated and purified by conventional means, preferably purified by reverse-phase HPLC.

If, instead of preparing a substituted [C] derivative of formula (32), it is desired to make a free acid derivative, the compound of formula (25) can be reacted directly with a "preactivated" dicarboxylic acid of formula (6), as described below.

An alternative method of preparing compounds of Formula I wherein the linkage is [V—V] and the [C]-position is substituted on both glycopeptide units is from reaction of the intermediate of formula (36) the preparation of these intermediates is shown below in Scheme 9.

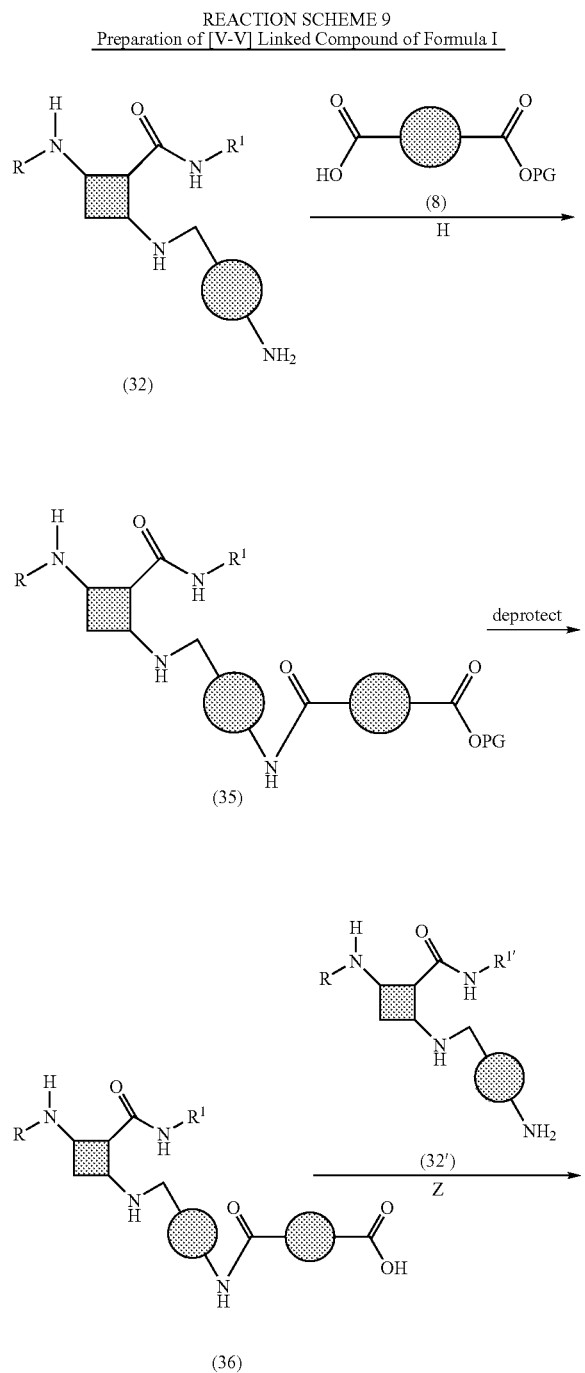

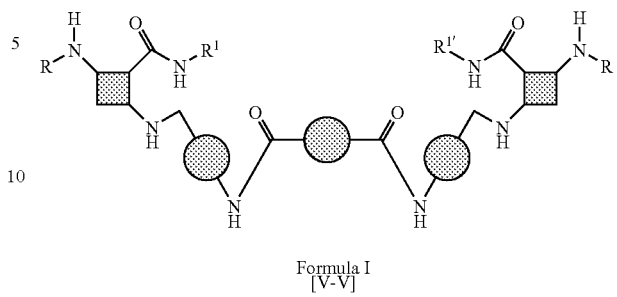

in which R is hydrogen or methyl, PG represents a protecting group, preferably 9-fluorenylmethyl, and where $R^1$, $R^{1'}$ are independently alkyl, aryl, heteroaryl, arylalkyl, heteroarylalkyl, all of which may be optionally substituted.

Preparation of Compounds of Formula (36)

As illustrated in Reaction Scheme 9, the compound of formula (32) is reacted with a monoester of a dicarboxylic acid (8); preferably the monoester is one easily hydrolyzed under mild conditions, for example a 9-fluorenylmethyl ester. In general, about one molar equivalent of (32) is reacted with one molar equivalent of (8). The reaction is carried out under conventional amide coupling conditions. Preferably, a hindered base is employed, preferably diisopropylethylamine, in the presence of PyBOP and 1-hydroxybenzotriazole. The reaction is conducted in an inert polar solvent, preferably DMF, at about room temperature for about 1–3 hours, preferably about 80 minutes. When the reaction is substantially complete, the desired product (35) is isolated by conventional means, and reacted with a mild base, preferably piperidine, to remove the protecting group. The reaction is conducted in an inert polar solvent, preferably DMF, at about room temperature for about 1–3 hours, preferably about 1 hour. When the reaction is substantially complete, the compound of formula (36) is isolated and purified by conventional means, preferably purified by reverse-phase HPLC.

The intermediate of formula (36) is then converted into a [V—V] bivalent compound wherein the [C]-position is substituted on both vancomycin subunits by reaction with a compound of formula (32') [not necessarily the same as starting material (32)].

Preparation of Compounds of Formula I

As illustrated in Reaction Scheme 9, step 3, the compound of formula (36) is reacted with a compound of formula (32'). In general, about equimolar equivalents of the compounds of formula (36) and (32') are reacted under conventional amide coupling conditions. Preferably, a hindered base is employed, preferably diisopropylethylamine, in the presence of PyBOP and 1-hydroxybenzotriazole. The reaction is conducted in an inert polar solvent, preferably DMF, at about room temperature for about 30 minutes to 3 hours, preferably about 1 hour. When the reaction is substantially complete, the compound of Formula I is isolated and purified by conventional means, preferably purified by reverse-phase HPLC.

It should be emphasized that the two glycopeptides (represented as shaded boxes) can be the same or different (or the same but differently substituted), and the linking groups, although always represented by a shaded circle, can be the same or different at each occurrence.

REACTION SCHEME 10
Preparation of an [N-N] linked Compound of Formula I

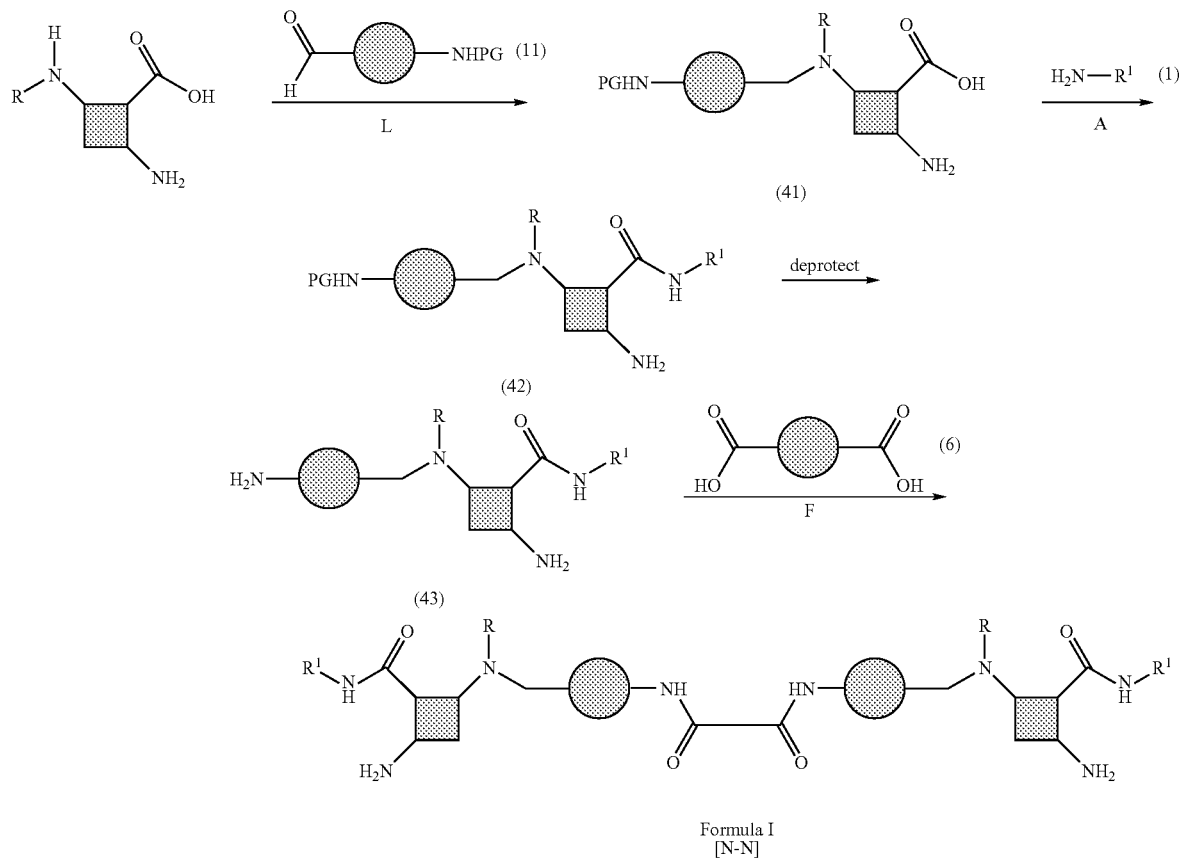

Formula I
[N-N]

in which R is hydrogen or methyl, PG represents a protecting group, preferably 9-fluorenylmethoxycarbonyl, and R is, alkyl, aryl, heteroaryl, arylalkyl, heteroarylalkyl, or a quarternary salt derivative.

Preparation of Compounds of Formula (41)

As illustrated in Reaction Scheme 10, step 1, a glycopeptide, for example vancomycin, is reacted with a protected aminoaldehyde under conditions sufficient to direct the aldehyde to the [N]-position. The Schiff's base thus formed is reduced in the same manner as shown in Reaction Scheme 6, step 1, to form a compound of formula (41).

Preparation of Compounds of Formula (42)

As illustrated in Reaction Scheme 10, step 2, the compound of formula (41) is reacted with an amine (1) in a coupling reaction in the same manner as shown above, for example in Reaction Scheme 8, step 1, to form an amide of formula (42).

Preparation of Compounds of Formula (43)

As illustrated in Reaction Scheme 10, step 3, the compound of formula (42) is deprotected conventionally as shown above, for example in Reaction Scheme 5, step 2, to form a compound of formula (43).

Preparation of Compounds of Formula I

As illustrated in Reaction Scheme 10, step 4, the compound of formula (43) is reacted with a dicarboxylic acid in the same manner as shown above, for example in Reaction Scheme 8, step 3, to give a compound of Formula I which is isolated and purified by conventional means, preferably by reverse-phase HPLC.

Aglycones

As described above, the invention also encompasses aglycone derivatives of glycopeptides, for example vancomycin lacking the amino sugar moiety. Such a compound has a hydroxy group as a point of attachment in place of the [V] amino group of the amino sugar. In the following reaction schemes, aglycones are represented as described above, i.e. they are depicted as a shaded triangle that shows only the carboxyl terminus, the aglycone hydroxy terminus, and the amino terminus.

Reaction Scheme 10 shows the preparation of an aglycone bivalent compound from a glycopeptide. The glycopeptide is initially substituted at the [C] position with an amide, followed by hydrolysis of the aminosugar, and finally coupling of the phenol thus produced.

REACTION SCHEME 11
Preparation of an [O-O] Linked Compound of Formula I

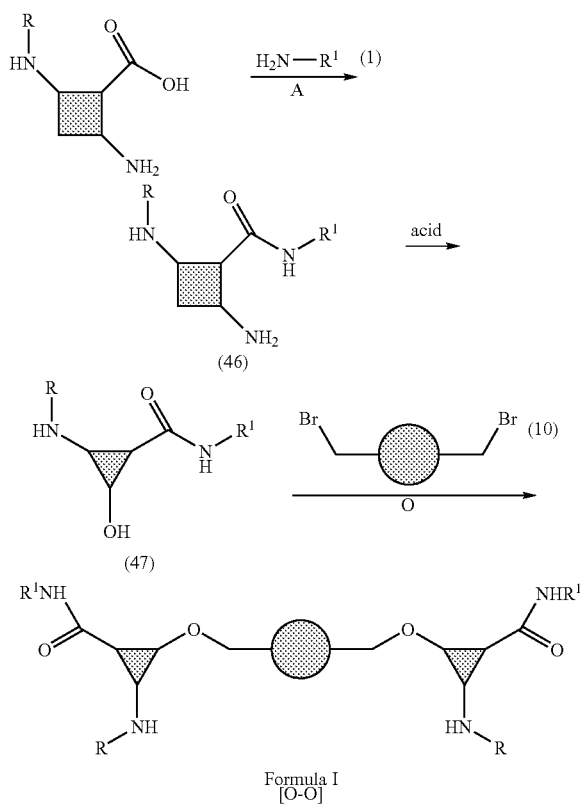

where R is hydrogen or methyl, and $R^1$ is alkyl, aryl, heteroaryl, arylalkyl, heteroarylalkyl, all of which may be optionally substituted Preparation of Compounds of Formula (46)

As illustrated in Reaction Scheme 11, step 1, a glycopeptide, for example vancomycin, is is reacted with an amine (1) in a coupling reaction in the same manner as shown above, for example in Reaction Scheme 8, step 1, to form an amide of formula (46), which is isolated and purified by conventional means.

Preparation of Compounds of Formula (47)

As illustrated in Reaction Scheme 11, step 2, the glycopeptide of formula (46) is hydrolysed with a strong acid, preferably at about 50° C., to produce an aglycone of formula (47), which is isolated and purified by conventional means.

Preparation of Compounds of Formula I

As illustrated in Reaction Scheme 11, step 3, two equivalents of the compound of formula (47) are reacted with a dihalo compound of formula (10) to give a compound of Formula I [O—O]. The reaction is carried out in a polar solvent, preferably DMF, in the presence of a base, preferably potassium carbonate, for about 30 hours. The compound of Formula I is isolated and purified by conventional means.

Alternatively, as shown in Reaction Scheme 12, the compound of formula (47) may be first reacted with a protected haloamine, for example tert-butyl N-(2-bromoethyl)carbamate, to give an aminoether of formula (51), which is then deprotected and reacted further with a dicarboxylic acid to give a compound of Formula I.

REACTION SCHEME 12
Preparation of a [O-O] linked Compound of Formula I

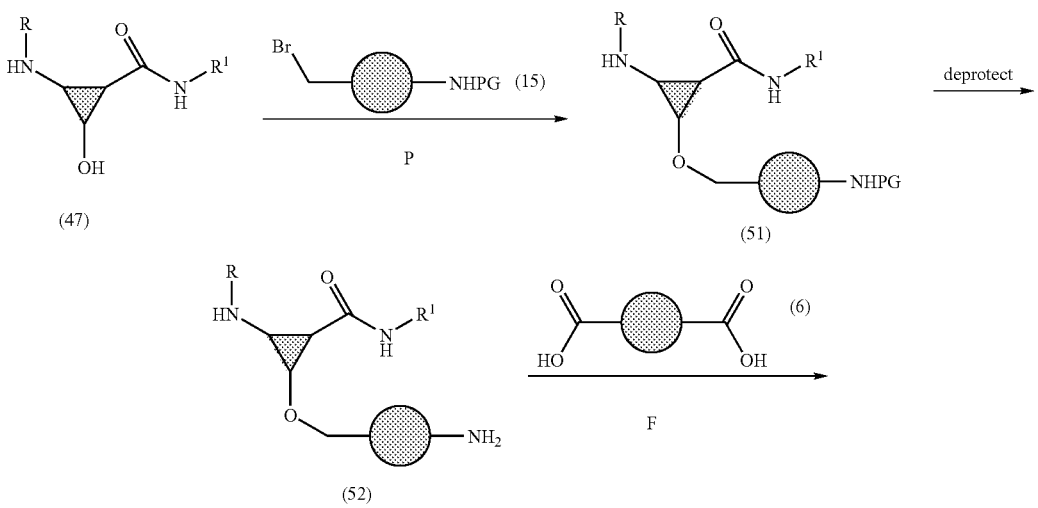

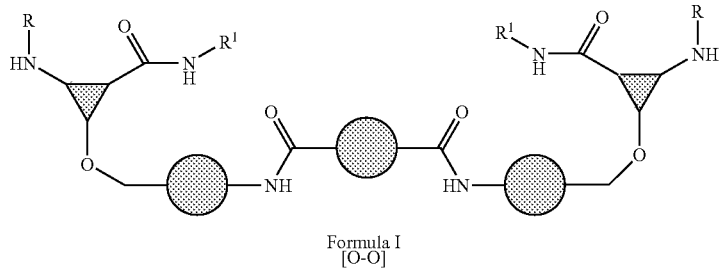

Formula I
[O-O]

where R is hydrogen or methyl, and PG represents a protecting group, preferably BOC, and where $R^1$ is alkyl, aryl, heteroaryl, arylalkyl, heteroarylalkyl, all of which may be optionally substituted.

Preparation of a Compound of Formula (51)

As illustrated in Reaction Scheme 12, step 1, an aglycone of formula (47) is reacted with a protected haloamine, for example tert-butyl N-(2-bromoethyl)carbamate, under conventional coupling conditions, preferably using potassium carbonate as a base in an inert polar solvent, preferably DMF or DMSO, at about room temperature. When the reaction is substantially complete, the compound of formula (51) is isolated and purified by conventional means.

Preparation of a Compound of Formula (52)

As illustrated in Reaction Scheme 12, step 2, the protecting group (carbamate) is hydrolyzed under acidic conditions. In general a preferred acid is trifluoroacetic acid, and the reaction is conducted in an inert solvent, at about room temperature. When the reaction is substantially complete, the compound of formula (52) is isolated and purified by conventional means.

Preparation of Compounds of Formula I

As illustrated in Reaction Scheme 12, step 3, two equivalents of the compound of formula (52) are reacted with a dicarboxylic acid compound of formula (6) to give a compound of Formula I [O—O]. The reaction is carried out under conventional amide coupling conditions as detailed above, for example, as in Reaction Scheme 8, step 3, to give a compound of Formula I.

Alternatively, as shown in Reaction Scheme 13, the compound of formula (47) may be first reacted with a haloester, for example t-butylbromoacetate, to give a carboxy-substituted ether, which is deprotected and then reacted further with a diamine to give a compound of Formula I.

REACTION SCHEME 13
Preparation of a [O-O] Linked Compound of Formula I

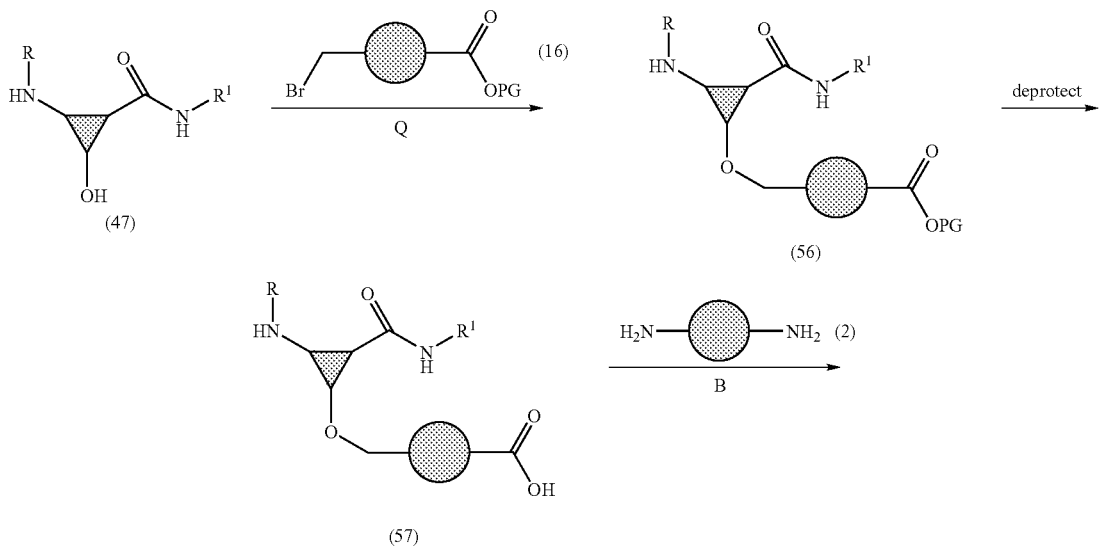

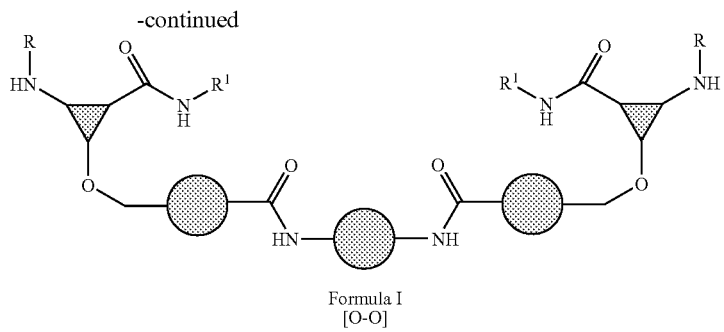

Formula I
[O-O]

where R is hydrogen or methyl, and PG represents a protecting group, and where $R^1$ is alkyl, aryl, heteroaryl, arylalkyl, heteroarylalkyl, all of which may be optionally substituted Preparation of Compounds of Formula (56)

As illustrated in Reaction Scheme 13, step 1, an aglycone of formula (47) is reacted with a haloester under conventional coupling conditions, preferably using potassium carbonate as a base in an inert polar solvent, preferably DMF or DMSO, at about room temperature. When the reaction is substantially complete, the compound of formula (56) is isolated and purified by conventional means.

Preparation of a Compound of Formula (57)

As illustrated in Reaction Scheme 13, step 2, the protecting group (carbamate) is hydrolyzed under acidic conditions. In general a preferred acid is trifluoroacetic acid, and the reaction is conducted in an inert solvent, at about room temperature. When the reaction is substantially complete, the compound of formula (57) is isolated and purified by conventional means.

Preparation of Compounds of Formula I

As illustrated in Reaction Scheme 13, step 3, two equivalents of the compound of formula (57) are reacted with a diamino compound of formula (2) to give a compound of Formula I [O—O]. The reaction is carried out under conventional amide coupling conditions as detailed above. Preferably, a hindered base is employed, preferably diisopropylethylamine, in the presence of PyBOP and 1-hydroxybenzotriazole. The reaction is conducted in an inert polar solvent, preferably DMF, at about room temperature for about 30 minutes to 5 hours, preferably about 2 hours. When the reaction is substantially complete, the compound of Formula I is isolated and purified by conventional means, preferably purified by reverse-phase HPLC.

A new type of chemical modification of glycopeptides is described in a recent publication from The Institute of New Antibiotics, Russian Academy of Medical Sciences, B. Pirogovskaya 11, 119867 Moscow, Russia. The reaction disclosed therein utilizes the Mannich reaction to derivatize the glycopeptide at the position between the two meta hydroxy groups on the "resorcinol" group (identified above in Structure II as the [R] position). This type of reaction can be used to prepare compounds of the invention, as shown below in Reaction Scheme 14.

REACTION SCHEME 14
Preparation of [R-R] linked Compound of Formula I

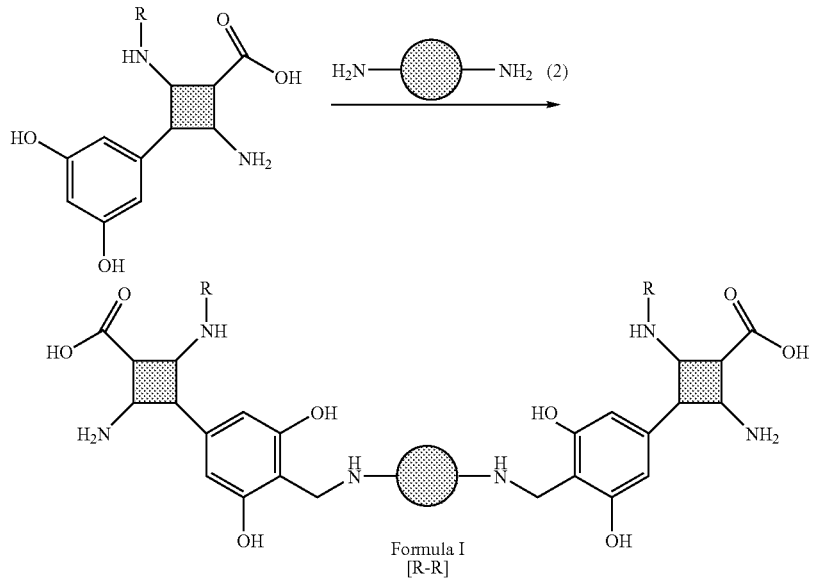

Formula I
[R-R]

where R is hydrogen or methyl.

Preparation of a Compound of Formula I

As illustrated in Reaction Scheme 14, a glycopeptide, for example vancomycin, is linked at the [R] position. In general, about two molar equivalents of a glycopeptide, for example vancomycin, are reacted with about two molar equivalents of formalin and one molar equivalent of diamine (2). The reaction is conducted in an inert polar solvent, preferably aqueous acetonitrile, for about 18 hours. When the reaction is substantially complete, the compound of Formula I is isolated and purified by conventional means, preferably purified by reverse-phase HPLC.

Secondary amines can be used in place of the primary amines of the linker of formula (2) if desired, and the [C] position can be substituted, for example by $NHR^1$, as shown previously if preferred.

Alternatively, the Mannich reaction can be used to introduce an amino sidechain or an acid sidechain at the [R] position (for example, as shown for the compound of formula (82)), which can then be further reacted with an appropriate linker (a diacid, dialdehyde, dihalo compound) as shown above to provide a compound of Formula I.

Compounds of Formula I wherein the link is [C—V] can be prepared as shown below in Reaction Schemes 15–20.

REACTION SCHEME 15
Preparation of a [C-V] Linked Compound of Formula I

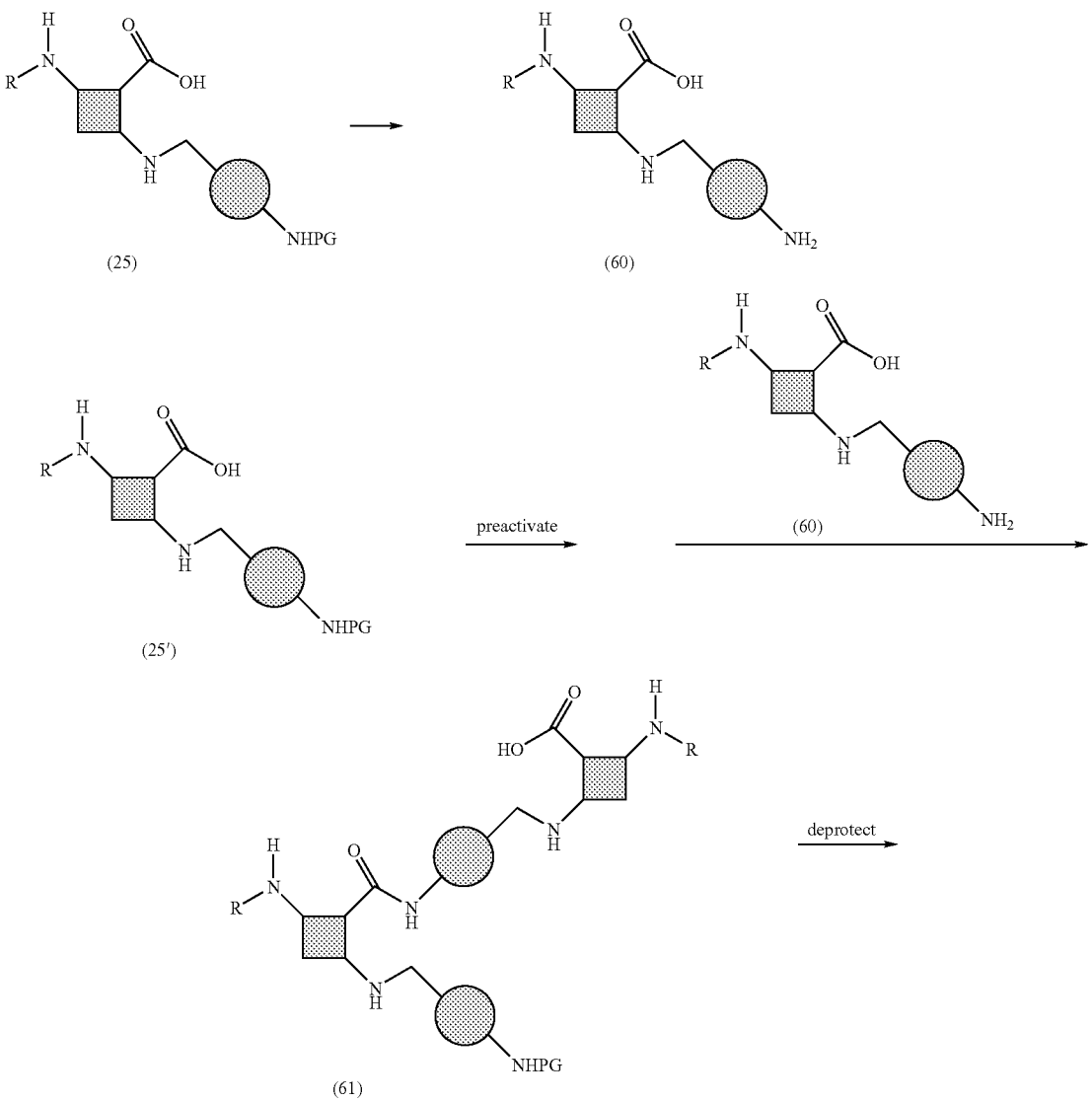

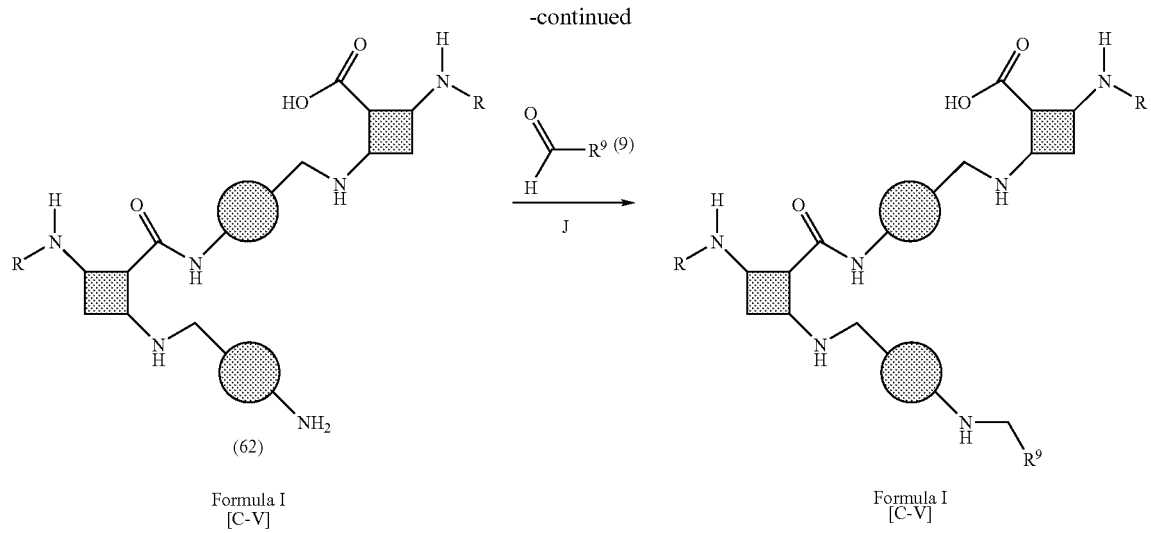

Formula I [C-V]  →  Formula I [C-V]

in which R is hydrogen or methyl, PG represents a protecting group, preferably 9-fluorenylmethoxycarbonyl, and $R^9$ is, alkyl, aryl, heteroaryl, arylalkyl, heteroarylalkyl, or a quarternary salt derivative.

Preparation of a [C—V] Compound of Formula I

In general, the compounds of [C—V] Formula I are prepared by the procedures of Reaction Scheme 15 using reactions described previously. However, one important difference is that the [C] carboxy group of the compound of formula (25) is preferably first "preactivated" before reaction with the compound of formula (60), because (60) also contains a free carboxy group.

REACTION SCHEME 16
Preparation of a [C-V] Linked Compound of Formula I

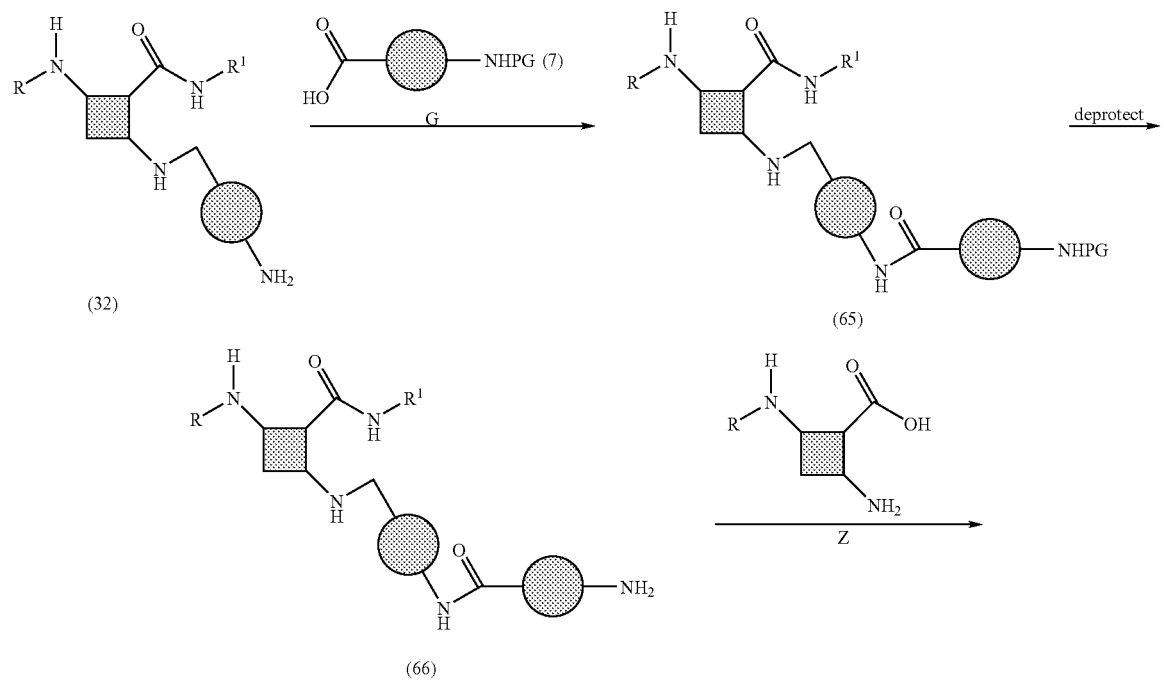

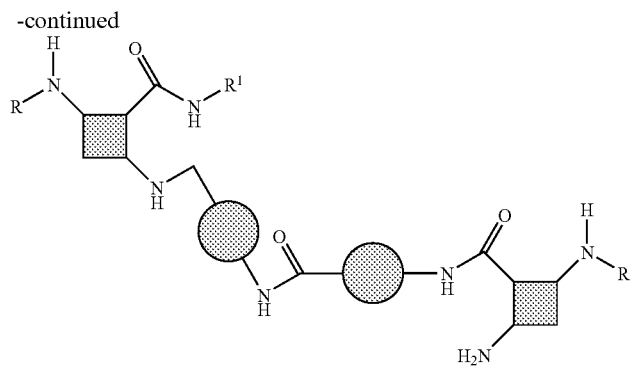

Formula I
[C-V]

in which R is hydrogen or methyl, PG represents a protecting group, preferably 9-fluorenylmethoxycarbonyl, and $R^1$ is, alkyl, aryl, heteroaryl, arylalkyl, heteroarylalkyl, or a quarternary salt derivative.

Preparation of a Compound of Formula (66)

As illustrated in Reaction Scheme 16, the compound of formula (32) is reacted with an N-protected aminoacid (7) in the same manner as shown above, for example in Reaction Scheme 9, step 1, to form a protected amide, which is then deprotected conventionally, for example as in Reaction Scheme 5, step 2, to form a compound of formula (66).

The compound of formula (66) is then converted into a [C—V] bivalent compound of Formula I by reaction with a glycopeptide, for example vancomycin.

Preparation of Compounds of Formula I

As illustrated in Reaction Scheme 16, step 3, the compound of formula (66) is reacted with a glycopeptide in a typical coupling reaction, as shown above, to give a compound of Formula I [C—V].

Reaction Scheme 17 shows the preparation of [C—V] compounds of Formula I using techniques described above, i.e. reductive alkylation to provide a protected amino "handle", followed by coupling of the [C]-position to a [V] amino substituted compound, and deprotection.

REACTION SCEME 17
Preparation of a [C-V] Linked Compound of Formula I

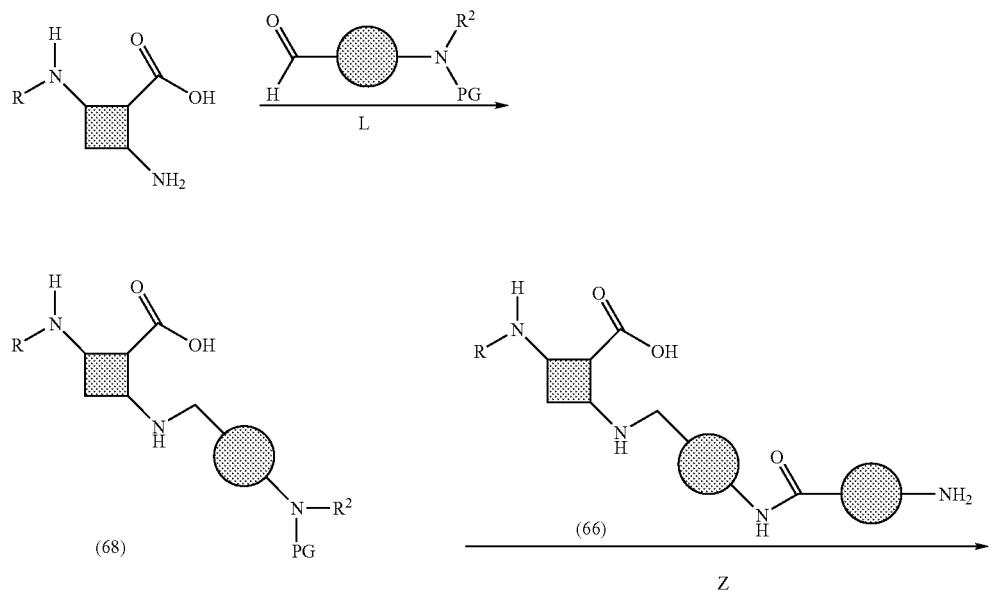

-continued

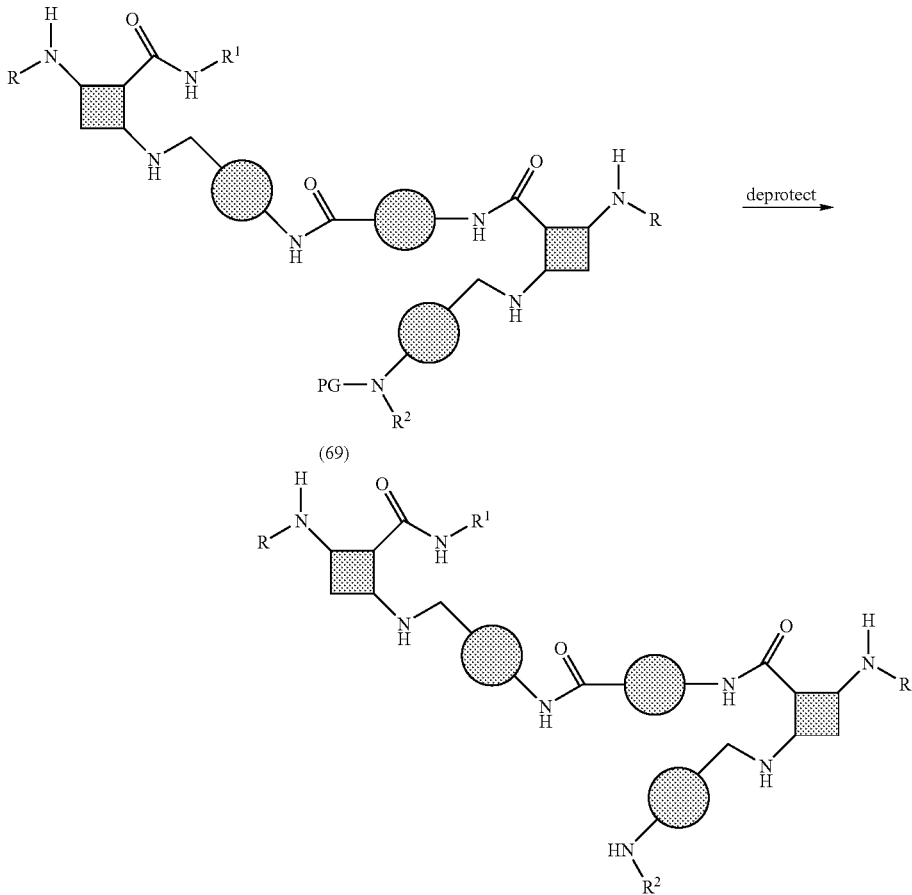

(69)

Formula I
[C-V]

in which R is hydrogen or methyl, PG represents a protecting group, preferably 9-fluorenylmethoxycarbonyl, and R¹ and R² are independently alkyl, aryl, heteroaryl, arylalkyl, heteroarylalkyl, or a quarternary salt derivative.

Compounds of Formula I wherein the linkage is [C—V] may be prepared from intermediates of formula (72), the preparation of which is shown below in Reaction Scheme 18.

REACTION SCHEME 18
Preparation of a [C-V] Linked Compound of Formula I

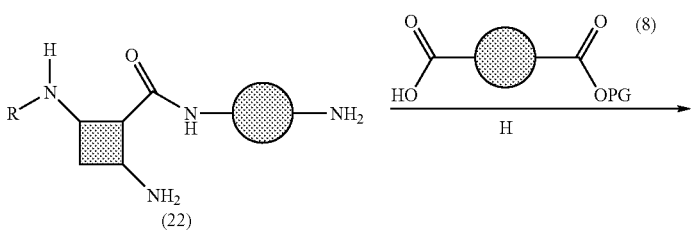

-continued

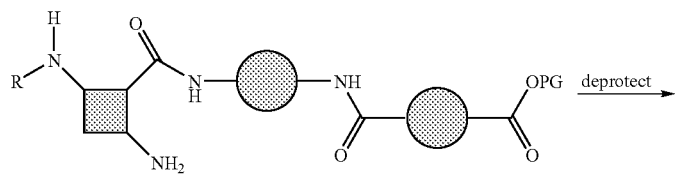

(71)

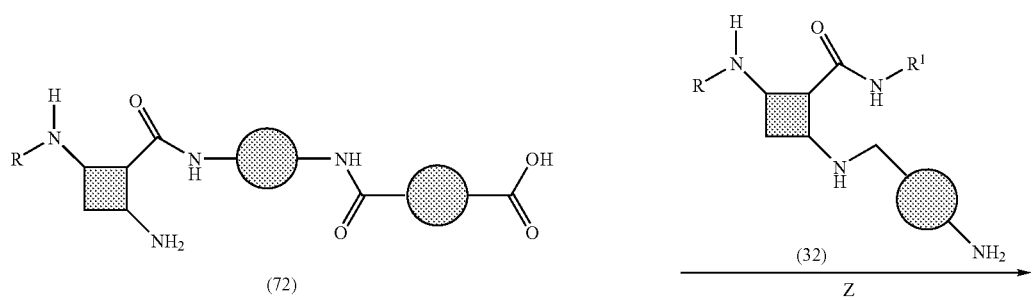

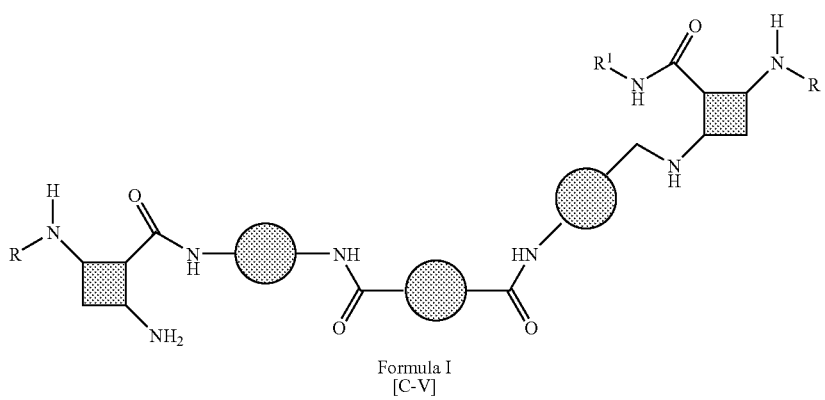

Formula I
[C-V]

in which R is hydrogen or methyl, PG represents a protecting group, for example 9-fluorenylmethyl, and $R^1$ is alkyl, alkylamino, alkylaminoalkyl, aryl, heteroaryl, arylalkyl, heteroarylalkyl, or a quarternary salt derivative.

Preparation of a Compound of Formula (72)

As illustrated in Reaction Scheme 18, step 1, the compound of formula (22) is reacted with an acid in the same manner as shown above, for example in Reaction Scheme 9, step 1, to form a protected amide, which is then deprotected conventionally, for example as in Reaction Scheme 9, step 2, to form a compound of formula (72).

The compound of formula (72) is then converted into a [C—V] bivalent compound of Formula I by reaction with a compound of formula (32), prepared as shown previously, as shown in Reaction Scheme 6.

Preparation of Compounds of Formula I

As illustrated in Reaction Scheme 18, step 3, the compound of formula (72) is reacted with a compound of formula (32) in a typical coupling reaction as shown above, to give a compound of Formula I [C—V].

The compound of [C—V] Formula I thus prepared is substituted at the second [C] terminus (by $R^1$NH). The free acid (i.e., the unsubstiututed [C] terminus) can be obtained, if desired, by substituting the compound of formula (60) for (32), and preactivating the compound of formula (72) as explained above.

Compounds of Formula I wherein the linkage is [C—V] and the [C] terminus of one vancomycin and the [V] terminus of a second vancomycin are both substituted may be prepared from intermediates of formula (77), the preparation of which is shown below in Reaction Scheme 19.

REACTION SCHEME 19
Preparation of a [C-V] Linked Compound of Formula I

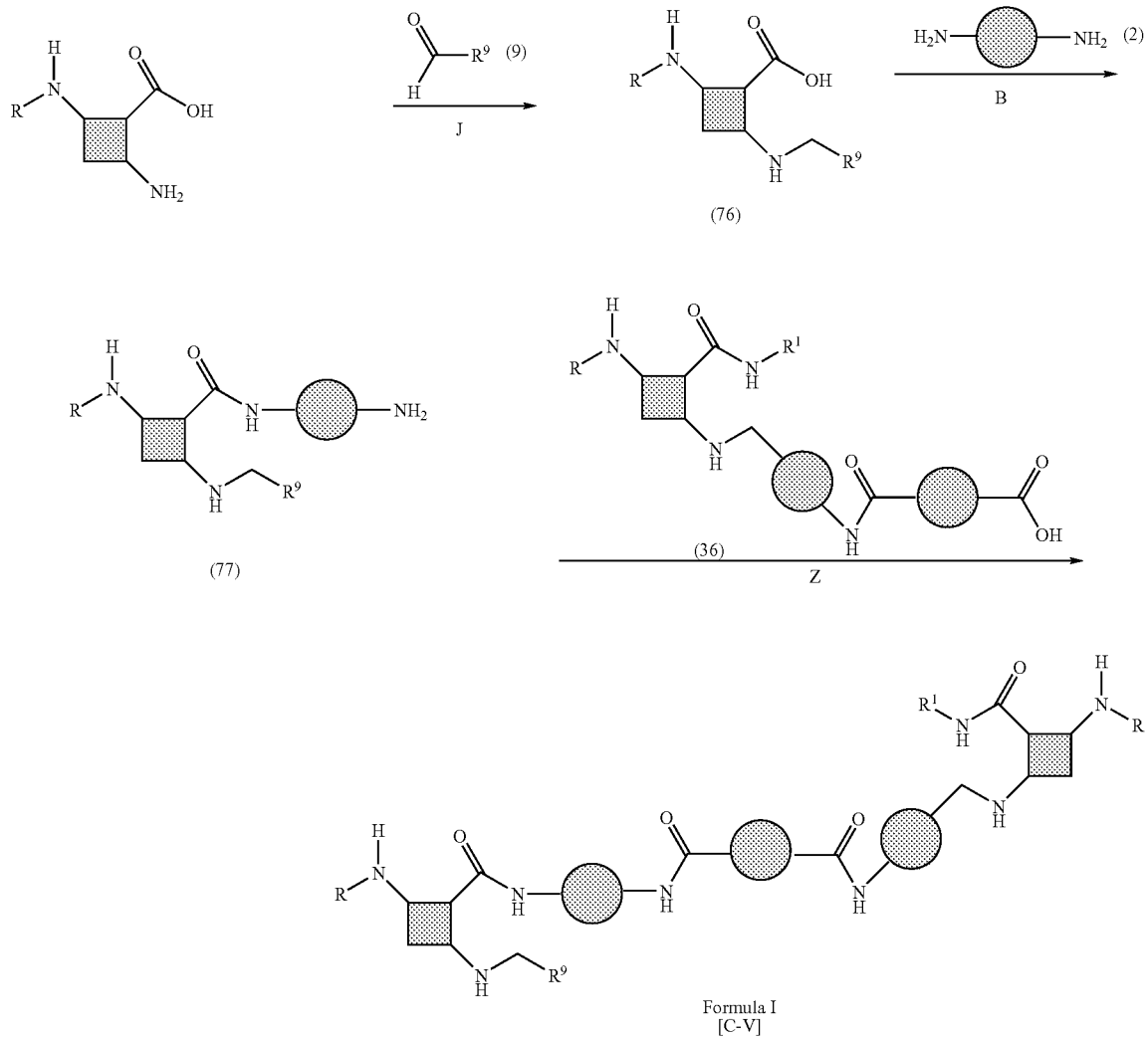

where R is hydrogen or methyl, PG represents a protecting group, preferably 9-fluorenylmethoxycarbonyl, and $R^1$, $R^9$ are independently chosen from hydrogen, alkyl, aryl, heteroaryl, arylalkyl, heteroarylalkyl, and a quarternary salt derivative.

Preparation of a Compound of Formula (76)

As illustrated in Reaction Scheme 19, step 1, a glycopeptide, for example vancomycin, is reacted with an aldehyde of formula $R^9$CHO, using excess base in order to direct the alkylation to the [V] position. The Schiff's base thus formed is reduced in the same manner as shown in Reaction Scheme 6, step 1, to form a compound of formula (76).

Preparation of Compounds of Formula (77)

As illustrated in Reaction Scheme 19, step 2, the compound of formula (76) is reacted with a diamine (2) to form an amide of formula (77).

The compound of formula (77) is then converted into a [C—V] bivalent compound of Formula I (in which the [C] terminus of one glycopeptide and the [V] terminus of a second glycopeptide are both substituted) by reaction with a compound of formula (36), prepared as shown in Reaction Scheme 9.

Preparation of Compounds of Formula I

As illustrated in Reaction Scheme 19, step 3, the compound of formula (77) is reacted with a compound of formula (36) in a typical coupling reaction as shown above to give a compound of Formula I [C—V] in which the [C] terminus of one glycopeptide and the [V] terminus of a second glycopeptide are additionally substituted.

Compounds of Formula I wherein the linkage is [C—V] and the [C] terminus of one vancomycin and the [V] terminus of a second vancomycin are both substituted may also be prepared from intermediates of formula (32), the preparation of which is shown below in Reaction Scheme 20.

REACTION SCHEME 20
Preparation of a [C-V] Linked Compound of Formula I

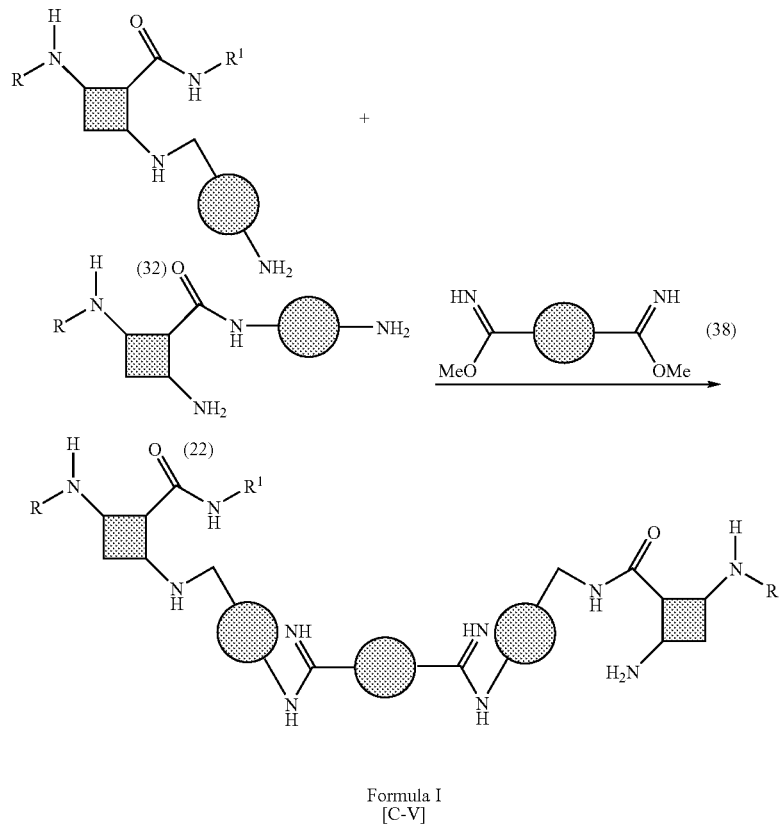

Formula I
[C-V]

where R is hydrogen or methyl, and R¹ is alkyl, aryl, heteroaryl, arylalkyl, or heteroarylalkyl, all of which may be optionally substituted.

Preparation of a Compound of Formula I

In general, one molar equivalent of a compound of Formula (32) and one molar equivalnent of a compound of Formula (22) are reacted with one molar equivalent of a bis-imidate of formula (38) under conventional coupling conditions. Preferably, a hindered base is employed, preferably diisopropylethylamine. The reaction is conducted in an inert polar solvent, for example N,N-dimethylformamide (DMF), for about one hour. When the reaction is substantially complete, the compound of Formula I (with a bis-amidine linker) is isolated and purified by conventional means, preferably purified by reverse-phase HPLC.

It should be noted that this reaction, which provides a bis(amidine) linker, can be employed in the same manner on any amine shown in the foregoing examples to give amidine linkers between all termini of a glycopeptide ([C—C], [V—V], etc).

Compounds of Formula I wherein the linkage is [C—N] may be prepared from intermediates of formula (43), the preparation of which was shown in Reaction Scheme 9.

REACTION SCHEME 21

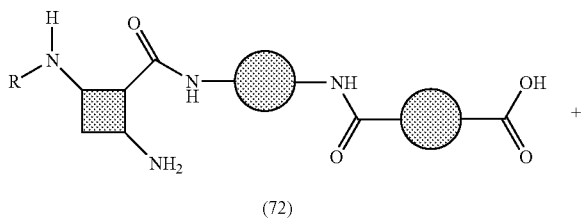

(72)

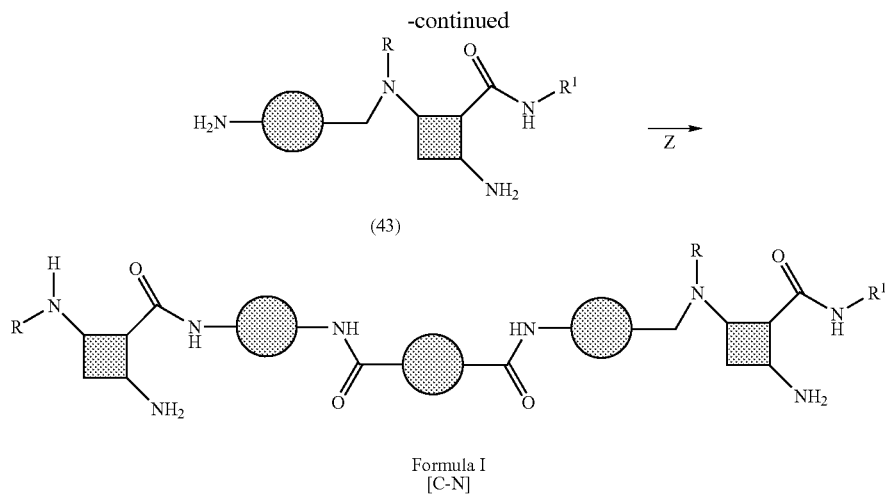

(43)

Formula I
[C-N]

where R is hydrogen or methyl, and $R^1$ is alkyl, aryl, heteroaryl, arylalkyl, or heteroarylalkyl, all of which may be optionally substituted.

Preparation of a [C—N] Linked Compound of Formula I

As illustrated in Reaction Scheme 21, the compound of formula (72) is reacted with a compound of formula (43) in a typical coupling reaction as shown above, to give a compound of Formula I [C—N].

Compounds of Formula I wherein the linkage is [N—V] may be prepared by reaction of a compound of formula (36) with a compound of formula (43), as shown in Reaction Scheme 22

REACTION SCHEME 22

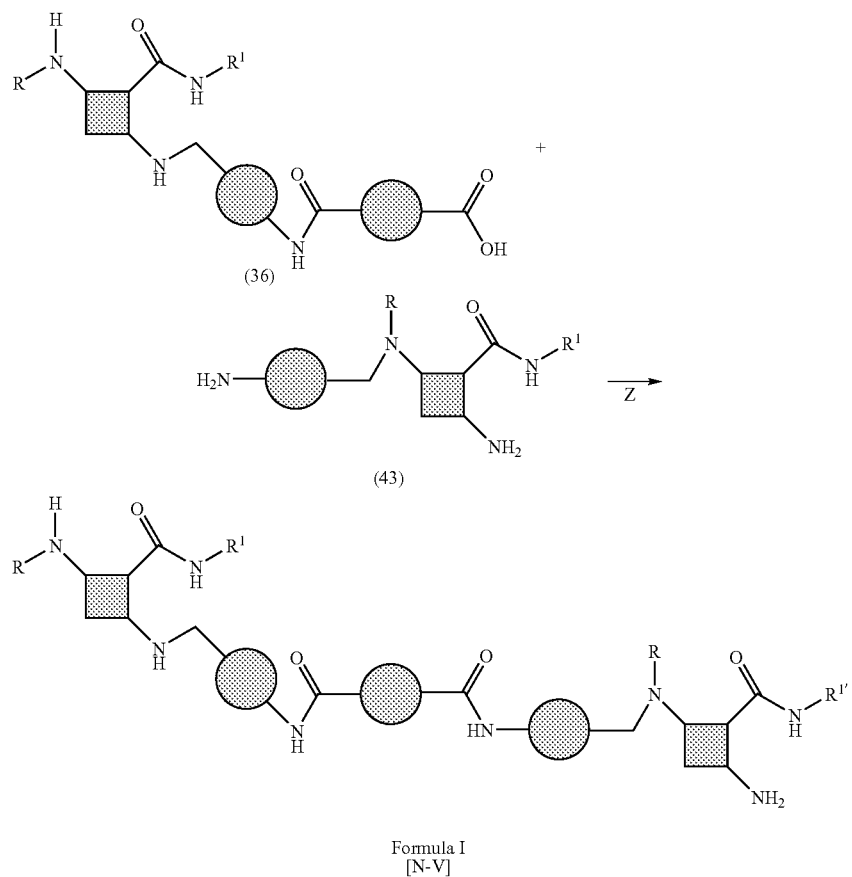

Formula I
[N-V]

where R is hydrogen or methyl, and R¹, R¹' is alkyl, aryl, heteroaryl, arylalkyl, or heteroarylalkyl, all of which may be optionally substituted.

Preparation of a [N—V] Linked Compound of Formula I

As illustrated in Reaction Scheme 22, the compound of formula (36) is reacted with a compound of formula (43), the preparation of which are detailed above, in a typical coupling reaction as shown above to give a compound of Formula I [N—V].

reaction as shown above, to give a compound of Formula I [C—R].

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chro- REACTION SCHEME 23
Preparation of a [C-R] Linked Compound of Formula I

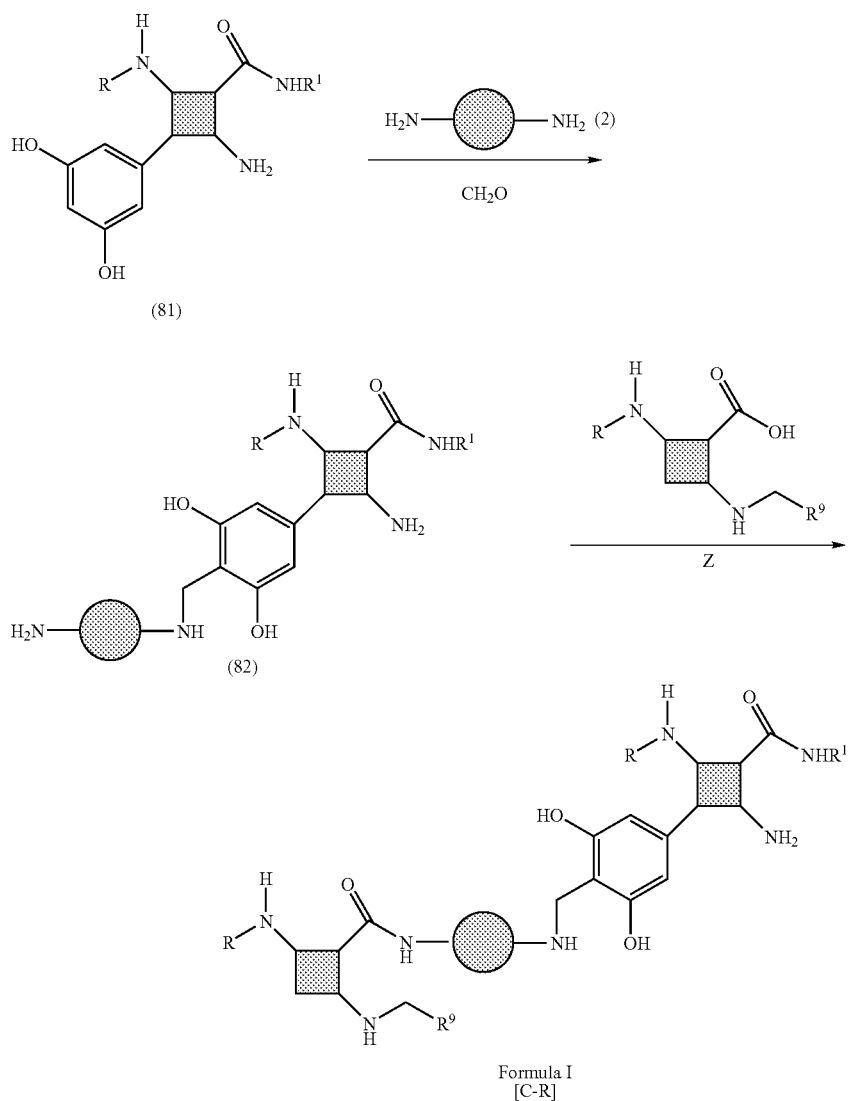

Preparation of a [C—R] Linked Compound of Formula I

As illustrated in Reaction Scheme 23, the compound of formula (81) is reacted with a diamine and formaldehyde, using typical reaction conditions for the Mannich reaction, to give a compound of formula (82). This amino derivative is then coupled with a glycopeptide, in a typical coupling matography, preparative low or high-pressure liquid chromatography or a combination of these procedures. Specific illustrations of suitable separation and isolation procedures can be had by reference to the Examples hereinbelow. However, other equivalent separation or isolation procedures could, of course, also be used.

73

EXAMPLE 1

Preparation of a Diamine of Formula (2)

(1) Preparation of a Compound of Formula (18)

To a solution of tert-butyl N-(2-aminoethyl)carbamate (3) (2.3 g, 14.4 mmol) and N,N-diisopropylethylamine (2.5 mL, 14.3 mmol) in 15 mL methylene chloride at 0° C. was added glutaryl dichloride (17) (0.6 mL, 4.7 mmol) in 15 mL methylene chloride dropwise. The resulting mixture was allowed to warm to room temperature with stirring while adding water (15 mL). The methylene chloride was removed under reduced pressure and more water was added (30 mL). The resulting suspension was filtered and washed sequentially with 10% potassium hydrogen sulfate, water, saturated sodium bicarbonate, and water. The solid was dried under vacuum yielding 1.3 g (3.1 mmol, 66%) of pentanedioic acid bis-[(2-t-butoxycarbonylaminoethyl)amide], a compound of formula (18).

(2) Preparation of a Compound of Formula (19)

The compound of formula (18) prepared above (1.3 g, 3.1 mmol) was suspended in 15 mL methylene chloride. 15 mL of trifluoroacetic acid was added at room temperature giving (with effervescence) a solution that was stirred for 40 minutes, then evaporated in vacuo. The residue was dissolved in methanol and treated with 3 mL 4N hydrogen chloride in dioxane followed by diethyl ether, giving a gum. The liquids were decanted and the gum dried under vacuum yielding 1.0 g (3.4 mmol, 110%) of pentanedioic acid bis-[(2-aminoethyl)amide], a compound of formula (19).

EXAMPLE 2

Preparation of a Protected Aminoaldehyde of Formula (7)

(1) Preparation of a Compound of Formula (21)

9-fluorenylmethyl N-(2-aminoethyl)carbamate (Fmoc-2-aminoethanol), a compound of formula (21), was prepared from aminoethanol, a compound of formula (20), by conventional techniques (see Example 3, step 2).

(2) Preparation of a Compound of Formula (7)

To a mixture of Fmoc-aminoethanol, a compound of formula (21) (37.64 g, 133 mmol, 1.0 equiv), TEMPO [2,2,6,6-tetramethyl-1-piperidinyloxy, free radical] (0.008 M in $CH_2Cl_2$, 332 mL, 2.66 mmol, 0.02 equiv), KBr (0.5 M in water, 53 mL, 26.6 mmol, 0.2 equiv) and ethyl acetate (1,500 mL), at 0° C., was added NaOCl (0.35 M, buffered to pH 8.6 by $NaHCO_3$, 760 mL, 266 mmol, 2.0 equiv). A mechanical stirrer was used to ensure efficient stirring, and the reaction was monitored by TLC. After 20 min, the two layers were separated. The aqueous layer was extracted with ethyl acetate (2×250 mL), the combined organic layers were washed with saturated $Na_2S_2O_3$, water, and brine, dried over $Na_2SO_4$, filtered and concentrated to about 400 mL. Hexane (1,600 mL) was added to give a white precipitate. After filtration, Fmoc aminoacetaldehyde (25.2 g, 67%), a compound of formula (7), was collected as a white powder.

74

EXAMPLE 3A

Preparation of a Protected Aminoaldehyde of Formula (95)

Preparation of a Compound of Formula (93)

A solution of aminoethanol (90) (30.5 g, 500 mmol, 30.1 mL) and 1-bromodecane (13) (27.65 g, 125 mmol, 26 mL) in ethanol was stirred at 65° C. for 4 hr. The solvent was removed under reduced pressure. The residue was diluted with EtOAc (800 mL) and the organic solution was washed with $H_2O$ (2×200 mL), aqueous HCl (2×200 mL, 1.0 M), saturated aqueous $NaHCO_3$ (200 mL) and saturated brine (200 mL). The organic phase was dried over anhydrous $Na_2SO_4$, and concentrated under reduced pressure. The resulting crude product, 2-(n-decylamino)ethanol (93), was used in the next reaction without further purification.

Preparation of a Compound of Formula (94)

A solution of 2-(n-decylamino)ethanol (93) (20.1 g, 100 mmol) in $CH_2Cl_2$ was treated with DIPEA (diisopropylethylamine, Hunig's base) (15.1 g, 120 mmol, 20.9 mL) at 0° C., followed by FmocCl (28.5 g, 110 mmol). The resulting reaction mixture was stirred at 0° C. for 1 hr and was poured into $CH_2Cl_2$ (400 mL). The mixture was washed with $H_2O$ (3×200 mL), aqueous HCl (1×200 mL, 1 N), saturated aqueous $NaHCO_3$ (200 mL) and brine (200 mL). The organic phase was dried over anhydrous $Na_2SO_4$, and concentrated under reduced pressure. The resulting white solid, N,N-n-decyl-Fmoc-aminoethanol (94), was used for the next reaction without further purification.

Preparation of a Compound of Formula (95)

A solution of N,N-n-decyl-Fmoc-aminoethanol (94) (12.7 g, 30 mmol) and DIPEA (15.48 g, 120 mmol, 20.9 mL) in $CH_2Cl_2$ was treated with a solution of sulfur trioxide pyridine complex in DMSO (85 mL) dropwise over 20 min at 0° C. The resulting reaction mixture was stirred at 0° C. for additional 20 min before it was quenched with water. The mixture was extracted with $CH_2Cl_2$ (5×100 mL) and the combined organic solutions were concentrated under reduced pressure. The residue was diluted with EtOAc (500 mL). The organic solution was washed with $H_2O$ (3×200 mL), aqueous HCl (200 mL, 1N), saturated aqueous $NaHCO_3$ (200 mL) and saturated brine (200 mL). The organic phase was dried over anhydrous $Na_2SO_4$, and concentrated under reduced pressure. The crude product was purified by column chromatography (25% EtOAc/hexanes) to yield n-decyl Fmoc-aminoaldehyde (95). MS ($MH^+$) calculated 422.2, found 422.2.

EXAMPLE 3B

Preparation of a Protected Aminoaldehyde of Formula (99)

Preparation of a Compound of Formula (96)

To a solution of decanoyl chloride (5) (2.7 mL, 13 mmol, 1.0 eq) in methylene chloride (20 mL) in an ice/acetone bath was added a mixture of glycine methyl ester hydrochloride (91) (2.0 g, 16 mmol, 1.2 eq) and DIPEA (5.1 mL, 29 mmol, 2.2 eq) in methylene chloride (20 mL) dropwise. The reaction was stirred a further 60 min after complete addition, then washed with 3N hydrochloric acid (50 mL) twice, followed by saturated sodium bicarbonate (50 mL). The organics were dried over magnesium sulfate and the solvents removed under reduced pressure. n-Decylglycine, a compound of formula (96) (3.0 g, 12 mmol, 95%) was obtained, and used in the next step without further purification.

Preparation of a Compound of Formula (97)

Under nitrogen, amide (96) (3.0 g, 12 mmol, 1.0 eq) was dissolved in anhydrous tetrahydrofuran (25 mL) and cooled in an ice bath. A solution of lithium aluminum hydride (1N, mL, 25 mmol, 2.0 eq) was added carefully. The resulting solution was refluxed under nitrogen overnight, then cooled in an ice bath. 50 mL more tetrahydrofuran was added followed by slow addition of sodium sulfate decahydrate until effervescence ceased. The mixture was allowed to warm to room temperature, filtered, then concentrated under vacuum. 2-(n-decylamino)ethanol, a compound of formula (97) (2.3 g, 11 mmol, 93%) was obtained, and used without further purification.

Preparation of a Compound of Formula (98)

2-(n-decylamino)ethanol (97) (2.3 g, 11 mmol, 1.1 eq) and DIPEA (2.0 mL, 11 mmol, 1.1 eq) were dissolved in methylene chloride (15 mL) and cooled in an ice bath. 9-Fluorenylmethyl chloroformate (2.6 g, 10 mmol, 1.0 eq) in methylene chloride (15 mL) was added, the mixture stirred for 30 minutes then washed with 3N hydrochloric acid (50 mL) twice and saturated sodium bicarbonate (50 mL). The organics were dried over magnesium sulfate, and the solvents removed under reduced pressure. Fmoc-2-(n-decylamino)ethanol, a compound of formula (98), (4.6 g, 11 mmol, 108%) was used without further purification.

Preparation of Compound of Formula (99)

Fmoc-2-(n-decylamino)ethanol (98) (4.6 g, 11 mmol, 1.0 eq) and DIPEA (7.6 mL, 44 mmol, 4.0 eq) were dissolved in methylene chloride (30 mL) and cooled in an ice/acetone bath. A solution of sulfur trioxide pyridine complex (6.9 g, 43 mmol, 4.0 eq) in dimethyl sulfoxide (30 mL) was added, and the solution stirred for 20 minutes. Crushed ice was added and the mixture partitioned. The organics were washed with 3N hydrochloric acid twice, saturated sodium bicarbonate and saturated sodium chloride, dried over magnesium chloride, and concentrated under vacuum. Fmoc-2-(n-decylamino)acetaldehyde, a compound of formula (99) (3.4 g, 8 mmol, 74%) was used without further purification.

EXAMPLE 4

Preparation of a [C—C] Compound of Formula I (1) Preparation of a Compound of Formula I At room temperature vancomycin hydrochloride (3.6 g, 2.3 mmol) was dissolved in 36 mL of dimethylsulfoxide. To this solution was added pentanedioic acid-bis-(2-aminoethyl)amide, a compound of formula (2) (1.0 g, 3.4 mmol suspended in 27 mL N,N-dimethylformamide) followed by N,N-diisopropylethylamine (2.4 mL, 13.8 mmol). The resulting suspension was stirred at room temperature for several hours until it was mostly homogenous. Then a solution of PyBOP (1.3 g, 2.5 mmol) and 1-hydroxybenzotriazole (310 mg, 2.3 mmol) in 9 mL N,N-dimethylformamide was added rapidly dropwise. The mixture was stirred at room temperature for 1 hour and then added dropwise to 600 mL of acetonitrile, giving a precipitate that was filtered, washed with acetonitrile, then diethyl ether, and dried under vacuum. The crude product was purified by reverse-phase HPLC (50 minute 2–30% acetonitrile in water containing 0.1% trifluoroacetic acid to yield [C]-N-N' aminoethyl-glutaric amide (vancomycin) (a compound of formula (22) contaminated with-1-hydroxybenzotriazole, elutes at 29 minutes) and [C—C]-[pentane-1,5-dioic acid bis-((2-aminoethyl)amide]-bis-(vancomycin), a compound of Formula I (elutes at 36 minutes) as their respective trifluoroacetic acid salts.

EXAMPLE 5

Preparation of a [C—C] Compound of Formula I (1) Preparation of a Compound of Formula (21)

At room temperature vancomycin hydrochloride (7.3 g, 4.7 mmol) was dissolved in 75 mL of dimethylsulfoxide. To this solution was added N,N-diisopropylethylamine (4.1 mL, 23.5 mmol) followed by 9-fluorenylmethyl N-(2-aminoethyl)carbamate hydrochloride (1.8 g, 5.6 mmol). To the resulting solution at room temperature was added rapidly dropwise a solution of PyBOP (2.7 g, 5.2 mmol) and 1-hydroxybenzotriazole (630 mg, 4.7 mmol) in 75 mL 1,3-dimethyl-3,4,5,6-tetrahydro-2(1H)-pyrimidinone. The resulting solution was stirred at room temperature for 2 hours, then poured into 800 mL diethyl ether, giving a gum. The diethyl ether was decanted and the gum washed with additional diethyl ether to give [C]-[2-Fmoc-aminoethyl] vancomycin, a compound of formula (21).

(2) Preparation of a Compound of Formula (22)

The compound of formula (21) prepared above, as a gum, was then taken up in 40 mL of N,N-dimethylformamide, to which 10 mL of piperidine was added and the solution left to stand at room temperature for 20 minutes. The solution was then added dropwise to 450 mL of acetonitrile giving a precipitate. Centrifugation was followed by decantation of the acetonitrile and the residue washed twice with 450 mL of acetonitrile, once with 450 mL of diethyl ether and air dried. The residue was taken up in water, acidified to pH<5 with a small amount of 3N hydrochloric acid and purified by reverse-phase HPLC using a gradient of 2–30% acetonitrile in water containing 0.1% trifluoroacetic acid yielding [C]-(2-aminoethyl) vancomycin, a compound of formula (22).

(3) Preparation of a [C—C] Linked Compound of Formula I

The compound of formula (22) (400 mg, 220 μmmol) and glutaric acid (6) (10 mg, 76 μmmol) were dissolved in 5 mL N,N-dimethylformamide and N,N-diisopropylethylamine (140 μL, 800 μmol) followed by PyBOP (83 mg, 160 μmol) and 1-hydroxybenzotriazole (10 mg, 74 μmol) in 500 μL N,N-dimethylformamide. The reaction was stirred for 75 minutes at room temperature then an additional 20 mg of PyBOP was added. 75 minutes later the solution was dripped into 45 mL acetonitrile. The resulting precipitate was collected by centrifugation, washed with ether, air dried and purified by reverse-phase HPLC (50 min 2–30% acetonitrile in water containing 0.1% trifluoroacetic acid, elutes at 33 min) to give [C—C]-[pentane-1,5-dioic acid bis-[(2-aminoethyl)amide]-bis-(vancomycin), a compound of Formula I, as its trifluoroacetic salt.

EXAMPLE 6

Preparation of a [C—C] Compound of Formula I (1) Preparation of a Compound of Formula (25)

To an oven-dried, 1000 mL round bottomed flask, equipped with magnetic stirring bar, were added vancomycin hydrochloride (34.1 g, 23 mmol, 1 eq), N-Fmoc-aminoacetaldehyde (7) (6.5 g, 23 mmol, 1 eq), DIPEA (8.5 mL, 46 mmol, 2 eq) and DMF (340 mL). The mixture was stirred at ambient temperature over 2 hours, and monitored by HPLC. The reaction became homogenous, and ~90% conversion to the imine was observed. Methanol (340 mL) and NaCNBH$_3$ (4.3 g, 69 mmol, 3 eq) were added to the solution, followed by TFA (5.2 mL, 69 mmol, 3 eq). Stirring was continued for an additional hour at ambient temperature. After the reaction was complete, methanol was removed in vacuo. The residue containing the crude product and DMF was slowly poured into a 5L flask and stirred with acetonitrile (3.5L). A white precipitate was formed. The suspension was allowed to settle at ambient temperature and the supernatant was decanted. The white solid was filtrated and triturated with ether (2L). After filtration, the crude product (25) was dried under high vacuum overnight.

A 8×26 cm column was packed with octadecyl bonded silical gel. The column was washed with 800 mL of 90% Solvent B [acetonitrile in water, 0.1% TFA] and equilibrated with 800 mL of 10% Solvent B. Crude Fraction A (10 g) was dissolved in 30% Solvent B (150 mL, containing 2 mL of 3 N HCl) and loaded onto the column. It was then flashed with 10% B (800 mL×2), 40% B (800 mL×3) and 90% B (800 mL). The fractions were checked by analytical HPLC. After lyophilization, V-[Fmoc-2-aminoethyl] vancomycin (25) was obtained as its TFA salt.

(2) Preparation of a Compound of Formula (26)

At room temperature the compound of formula (25) prepared above (205 mg, 0.1 mmol) and [C]-[glutaryl bis-[(2-aminoethyl)amide] (vancomycin), a compound of formula (22), prepared as above (200 mg, 0.10 mmol), were dissolved in 2 mL N,N-dimethylformamide. To this solution was added N,N-diisopropylethylamine (126 uL, 0.72 mmol), 1-hydroxybenzotriazole (14 mg, 0.10 mmol) and PyBOP (59 mg, 0.11 mmol). The solution was stirred for 2 hours then added dropwise to 45 mL acetonitrile giving a precipitate that was collected by centrifugation. The precipitate was purified by reverse-phase HPLC (50 minutes 10–70% acetonitrile in water containing 0.1% trifluoroacetic acid, elutes at 24 minutes) giving [V]-[2-Fmoc-aminoethyl] [C—C]-pentane-1,5-dioic acid bis-[(2-aminoethyl)amide]-bis-(vancomycin), a compound of formula (26), as its trifluoroacetic acid salt.

(3) Preparation of a Compound of Formula (27)

To a solution of the compound of formula (26) prepared above, in 5 mL N,N-dimethylformamide was added 0.5 mL piperidine. The resulting solution was left at room temperature for 30 minutes, then added dropwise to acetonitrile, giving a precipitate that was collected by centrifugation, washed with ether and air dried. Reverse-phase HPLC purification (50 minutes 2–50% acetonitrile in water containing 0.1% trifluoroacetic acid, elutes at 24 minutes) yielded ([V]-[2-aminoethyl]) [C—C]-pentane-1,5-dioic acid bis-[(2-aminoethyl)amide]-bis-(vancomycin), a compound of formula (27), as its trifluoroacetic acid salt.

(4) Preparation of a C—C Compound of Formula I in which V is Substituted by n-Decylamidoethyl The compound of formula (27) prepared above (10 mg, 2.8 µmol), decanoic acid (0.5 mg, 2.9 µmol) and N,N-diisopropylethylamine (2.9 µL, 16.6 µmol) were dissolved in 200 µL N,N-dimethylformamide. PyBOP (1.5 mg, 2.9 µmol) and 1-hydroxybenzotriazole (0.4 mg, 3.0 µmol) in 20 µL N,N-dimethylformamide were added, the solution left at room temperature for 30 minutes and then added dropwise to 1.5 mL of acetonitrile, giving a precipitate. The precipitate was collected by centrifugation, washed with ether and air-dried. Reverse-phase HPLC purification (60 minutes 10–50% acetonitrile in water containing 0.1% trifluoroacetic acid, elutes at 42 minutes) yielded ([V]-(2-decylamido)ethyl)vancomycin [C—C]-pentane-1,5-dioic acid bis-[(2-aminoethyl)amide]-(vancomycin) a compound of Formula I, as its trifluoroacetic acid salt.

EXAMPLE 7

Preparation of a [C—C] Compound of Formula I via Alkylation

A mixture of [C]-[2-aminoethyl] vancomycin (22) (50 mg, 0.027 mmol), α,α'-dibromo-m-xylene (3.4 mg, 0.013 mmol) and N,N-diisopropylethylamine (6.5 mg, 0.050 mmol) in dimethylformamide (0.15 mL) was heated at 60° C. for 8 hours, cooled to room temperature for 18 hours and then heated at 60° C. for 8 hours. Upon cooling, the product was precipitated by the addition of acetonitrile (15 mL) and isolated by centrifugation. The solid product was washed with ether (15 mL) and dried in vacuo. Reverse-phase preprative HPLC (5–40% acetonitrile in water containing 0.1% trifluoroacetic acid over 90 min) gave the [C—C]-m-phenyl-bis[methylaminoethylamino] bis vancomycin as its trifluoroacetate salt. MS calculated (M+) 3084.8; found 3084.0.

Preparation of other [C—C] Compounds of Formula I

Accordingly, the following [C—C] compounds of Formula I were prepared following the procedures of Examples 1–7 above. It should be noted that "Class" denotes the point of attachment of the linker; V1, N1, and R1 represent the point of attachment with respect to the first glycopeptide; V2, N2, and R2 represent the point of attachment with respect to the second glycopeptide.

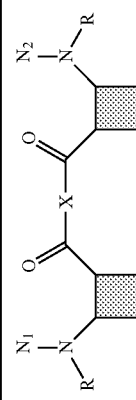

C—C COMPOUNDS

| No. | Class | Linker | V1 | V2 | N1 | N2 | R1 | R2 |
|---|---|---|---|---|---|---|---|---|
| 1 | C—C | —NH—(CH$_2$)$_2$—NH—C(O)—(CH$_2$)$_3$—C(O)—NH—(CH$_2$)$_2$—NH— | H | H | H | H | — | — |
| 2 | C—C | —NH—(CH$_2$)$_2$—NH—C(O)—(CH$_2$)$_2$—CH(NH—C(O)—Ph)—C(O)—NH—(CH$_2$)$_2$—NH— | H | H | H | H | — | — |
| 3 | C—C | —NH—(CH$_2$)$_2$—NH—C(O)—CH$_2$—N$^+$((CH$_2$)$_9$—CH$_3$)(CH$_2$—C(O)—NH—(CH$_2$)$_2$—NH— | H | H | H | H | — | — |
| 4 | C—C | —NH—(CH$_2$)$_2$—NH$_2$)—CH$_2$—C(O)—NH—CH$_2$—N((CH$_2$)$_9$—CH$_3$)—CH$_2$—C(O)—NH— | H | H | H | H | — | — |
| 5 | C—C | —NH—(CH$_2$)$_2$—C(O)—NH—(CH$_2$)$_4$—CH(NH—C(O)—CH$_3$)—C(O)—NH—CH(COOH)—(CH$_2$)$_4$—NH—C(O)—(CH$_2$)$_5$—NH— | H | H | H | H | — | — |
| 6 | C—C | —NH—(CH$_2$)$_2$—C(O)—NH—(CH$_2$)$_2$—C(O)—(CH$_2$)$_2$—C(O)—NH—(CH$_2$)$_3$—C(O)—NH—(CH$_2$)$_2$—C(O)—NH—(CH$_2$)$_2$—NH | H | H | H | H | — | — |
| 7 | C—C | —NH—(CH$_2$)$_2$—C(O)—NH—(CH$_2$)$_2$—NH—C(O)—(CH$_2$)$_3$—C(O)—NH—(CH$_2$)$_2$—NH— | H | H | H | H | — | — |
| 8 | C—C | —NH—(CH$_2$)$_2$—C(O)—Z—C(O)—NH—(CH$_2$)$_2$—NH— Where Z = 5-hydroxy-1,3-phenyl | H | H | H | H | — | — |
| 9 | C—C | —NH—(CH$_2$)$_2$—C(O)—Z—C(O)—NH—(CH$_2$)$_2$—NH— Where Z = 1,4-phenyl | H | H | H | H | — | — |
| 10 | C—C | —NH—(CH$_2$)$_2$—C(O)—Z—C(O)—NH—(CH$_2$)$_2$—NH— Where Z = 1,2-phenyl | H | H | H | H | — | — |
| 11 | C—C | —NH—(CH$_2$)$_3$—C(O)—NH—(CH$_2$)$_2$—NH— | —(CH$_2$)$_2$—NH—C(O)—(CH$_2$)$_8$—CH$_3$ | H | H | H | — | — |
| 12 | C—C | —NH—(CH$_2$)$_3$—C(O)—NH—(CH$_2$)$_2$—NH— | —(CH$_2$)$_2$—NH—C(O)—Z Where Z = biphenyl | H | H | H | — | — |
| 13 | C—C | —NH—(CH$_2$)$_3$—C(O)—NH—(CH$_2$)$_2$—NH— | H | H | —(CH$_2$)$_2$—NH—C(O)—(CH$_2$)$_8$—CH$_3$ | H | — | — |
| 14 | C—C | —NH—(CH$_2$)$_3$—C(O)—NH—(CH$_2$)$_2$—NH— | H | H | —(CH$_2$)$_2$—NH—C(O)—Z Where Z = biphenyl | H | — | — |
| 15 | C—C | —NH—(CH$_2$)$_4$—C(O)—NH—(CH$_2$)$_2$—NH— | H | H | H | H | — | — |
| 16 | C—C | —NH—(CH$_2$)$_2$—C(O)—NH—(CH$_2$)$_2$—NH— | H | H | H | H | — | — |
| 17 | C—C | —NH—(CH$_2$)$_4$—C(O)—NH—(CH$_2$)$_2$—NH— | H | H | H | H | — | — |
| 18 | C—C | —NH—(CH$_2$)$_2$—C(O)—NH—(CH$_2$)$_2$—NH— | H | H | H | H | — | — |
| 19 | C—C | —NH—(CH$_2$)$_3$)$_{10}$—C(O)—NH—(CH$_2$)$_2$—NH— | H | H | H | H | — | — |
| 20 | C—C | —NH—(CH$_2$)$_2$—NH—CH(NH—C(O)—(CH$_2$)$_8$—CH$_3$)—C(O)—NH—(CH$_2$)$_2$—NH— | H | H | H | H | — | — |
| 21 | C—C | —NH—(CH$_2$)$_2$—C(O)—Z—C(O)—NH—(CH$_2$)$_2$—NH— Where Z = 5-(n-octadecyloxy)-1,3-phenyl | H | H | H | H | — | — |

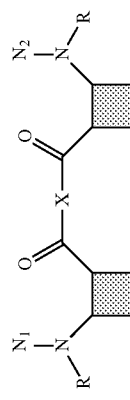

C—C COMPOUNDS

| No. | Class | Linker | V1 | V2 | N1 | N2 | R1 | R2 |
|---|---|---|---|---|---|---|---|---|
| 22 | C—C | —NH—$(CH_2)_2$—NH—C(O)—$(CH_2)_7$—C(O)—NH—$(CH_2)_2$—NH— | H | H | H | H | — | — |
| 23 | C—C | —NH—$(CH_2)_2$—NH—C(O)—$(CH_2)_2$—CH(NH—C(O)—Z)—C(O)—NH—$(CH_2)_2$—NH— Where Z = 4-(n-octyloxy)phenyl | H | H | H | H | — | — |
| 24 | C—C | —NH—$(CH_2)_2$—NH—C(O)—$(CH_2)_3$—C(O)—NH—$(CH_2)_2$—NH— | —$(CH_2)_4$—$CH_3$ | H | H | H | — | — |
| 25 | C—C | —NH—$(CH_2)_2$—NH—C(O)—$(CH_2)_3$—C(O)—NH—$(CH_2)_2$—NH— | —$(CH_2)_2$—NH—$CH_3$ | H | H | H | — | — |
| 26 | C—C | —NH—$(CH_2)_2$—NH—C(O)—$(CH_2)_3$—C(O)—NH—$(CH_2)_2$—NH— | —$(CH_2)_{12}$—NH—$CH_3$ | H | H | H | — | — |
| 27 | C—C | —NH—$(CH_2)_2$—NH—C(O)—$(CH_2)_3$—C(O)—NH—$(CH_2)_2$—NH— | $CH_2$—N$^+$($CH_3$)$_3$ | H | —$(CH_2)_2$—NH—C(O)—$CH_2$—N$^+$($CH_3$)$_3$ | H | — | — |
| 28 | C—C | —NH—$(CH_2)_2$—NH—C(O)—$(CH_2)_3$—C(O)—NH—$(CH_2)_2$—NH— | H | H | —$(CH_2)_2$—NH—$NH_2$ | H | — | — |
| 29 | C—C | —NH—$(CH_2)_2$—NH—C(O)—$(CH_2)_3$—C(O)—NH—$(CH_2)_2$—NH— | —$(CH_2)_8$—$CH_3$ | —$(CH_2)_2$—NH—C(O)—$(CH_2)_8$—$CH_3$ | H | H | — | — |
| 30 | C—C | —NH—$(CH_2)_2$—NH—C(O)—$(CH_2)_3$—C(O)—NH—$(CH_2)_2$—NH— | —$(CH_2)_2$—NH—$CH_3$ | H | H | H | — | — |
| 31 | C—C | —NH—$(CH_2)_2$—NH—C(O)—$(CH_2)_3$—C(O)—NH—$(CH_2)_2$—NH— | —$(CH_2)_8$—$CH_3$ | H | H | H | — | — |
| 32 | C—C | —NH—$(CH_2)_2$—NH—C(O)—$(CH_2)_3$—C(O)—NH—$(CH_2)_2$—NH— | —$(CH_2)_2$—NH—$CH_3$ | H | —$(CH_2)_9$—$CH_3$ | H | — | — |
| 33 | C—C | —NH—$(CH_2)_2$—NH—C(O)—$(CH_2)_3$—C(O)—NH—$(CH_2)_2$—NH— | —$(CH_2)_9$—$CH_3$ | H | —$(CH_2)_3$—COOH | H | — | — |
| 34 | C—C | —NH—$(CH_2)_2$—NH—C(O)—$(CH_2)_3$—C(O)—NH—$(CH_2)_2$—NH— | H | —$(CH_2)_2$—NH—C(O)—$CH_3$ | H | H | — | — |
| 35 | C—C | —NH—$(CH_2)_2$—NH—C(O)—$(CH_2)_3$—C(O)—NH—$(CH_2)_2$—NH— | —$(CH_2)_4$—$CH_3$ | —$(CH_2)_2$—NH—$CH_3$ | —$(CH_2)_2$—NH—C(O)—$CH_3$ | H | — | — |
| 36 | C—C | —NH—$(CH_2)_2$—NH—C(O)—$(CH_2)_3$—C(O)—NH—$(CH_2)_2$—NH— | —$(CH_2)_8$—$CH_3$ | H | —$(CH_2)_8$—$CH_3$ | H | — | — |
| 37 | C—C | —NH—$(CH_2)_2$—NH—C(O)—$(CH_2)_3$—C(O)—NH—$(CH_2)_2$—NH— | —$(CH_2)_8$—$NH_2$ | H | —$(CH_2)_2$—NH—C(O)—$NH_2$ | H | — | — |
| 38 | C—C | —NH—$(CH_2)_2$—NH—C(O)—$(CH_2)_3$—C(O)—NH—$(CH_2)_2$—NH— | —$(CH_2)_2$—NH—$CH_3$ | H | —$(CH_2)_2$—NH—C(O)—$CH_3$ | H | — | — |
| 39 | C—C | —NH—$(CH_2)_2$—NH—C(O)—$(CH_2)_3$—C(O)—NH—$(CH_2)_2$—NH— | —$(CH_2)_3$—COOH —$(CH_2)_8$—$CH_3$ | H | —$(CH_2)_3$—COOH H | H | — | — |
| 40 | C—C | —NH—$(CH_2)_2$—NH—C(O)—$(CH_2)_3$—C(O)—NH—$(CH_2)_2$—NH— | —$(CH_2)_3$—COOH | —$(CH_2)_8$—$CH_3$ | —$(CH_2)_2$—NH—C(O)—$CH_3$ | H | — | — |

C—C COMPOUNDS

| No. | Class | Linker | V1 | V2 | N1 | N2 | R1 | R2 |
|---|---|---|---|---|---|---|---|---|
| 41 | C—C | —NH—(CH$_2$)$_2$—NH—C(O)—(CH$_2$)$_3$—C(O)—NH—(CH$_2$)$_2$—NH—H | H | H | —(CH$_2$)$_2$—NH—C(O)—(CH$_2$)$_3$—C(O)—NH—(CH$_2$)$_3$—NH—(CH$_2$)$_3$—NH$_2$ | H | | |
| 42 | C—C | —NH—(CH$_2$)$_2$—NH—C(O)—(CH$_2$)$_3$—C(O)—NH—(CH$_2$)$_2$—NH— | H | H | —(CH$_2$)$_2$—NH—C(O)—(CH$_2$)$_2$—(CH(OH))$_5$—H | H | | |
| 43 | C—C | —NH—(CH$_2$)$_2$—NH—C(O)—(CH$_2$)$_3$—C(O)—NH—(CH$_2$)$_2$—NH— | —CH$_2$—Z—O—(CH$_2$)$_3$—CH$_3$ Where Z = 1,4-phenyl | H | H | H | | |
| 44 | C—C | —NH—(CH$_2$)$_2$—NH—C(O)—(CH$_2$)$_3$—C(O)—NH—(CH$_2$)$_2$—NH— | H | H | —CH$_2$—Z—O—(CH$_2$)$_3$—CH$_3$ Where Z = 1,4-phenyl | H | | |
| 45 | C—C | —NH—(CH$_2$)$_2$—NH—C(O)—(CH$_2$)$_2$—CH(NH—C(O)—Z)—C(O)—NH—(CH$_2$)$_2$—NH— Where Z = 4-(n-octoxy)phenyl | H | H | H | H | | |
| 46 | C—C | —NH—(CH$_2$)$_2$—NH—C(O)—(CH$_2$)$_3$—C(O)—NH—(CH$_2$)$_2$—NH— | —(CH$_2$)$_2$—NH—C(O)—(CH$_2$)$_3$—C(O)—NH—CH$_2$—(CH(OH))$_5$—H | H | H | H | | |
| 47 | C—C | —NH—(CH$_2$)$_2$—NH—C(O)—(CH$_2$)$_3$—C(O)—NH—(CH$_2$)$_2$—NH— | —CH$_2$—Z Where Z = biphenyl | —CH$_2$—Z Where Z = biphenyl | H | H | | |
| 48 | C—C | —NH—(CH$_2$)$_2$—NH—C(O)—(CH$_2$)$_3$—C(O)—NH—(CH$_2$)$_2$—NH— | H | H | —CH$_2$—Z Where Z = biphenyl | —CH$_2$—Z Where Z = biphenyl | | |
| 49 | C—C | —NH—(CH$_2$)$_2$—NH—C(O)—CH$_2$—O—CH$_2$—C(O)—NH—(CH$_2$)$_2$—NH— | —CH$_2$—Z Where Z = biphenyl | —CH$_2$—Z Where Z = biphenyl | H | H | | |
| 50 | C—C | —NH—(CH$_2$)$_2$—NH—C(O)—CH$_2$—O—CH$_2$—C(O)—NH—(CH$_2$)$_2$—NH— | H | H | —CH$_2$—Z Where Z = biphenyl | —CH$_2$—Z Where Z = biphenyl | | |
| 51 | C—C | —NH—(CH$_2$)$_2$—NH—C(O)—(CH$_2$)$_3$—C(O)—NH—(CH$_2$)$_2$—NH— | —(CH$_2$)$_2$—NH—(CH$_2$)$_9$—CH$_3$ | H | H | H | | |
| 52 | C—C | —NH—(CH$_2$)$_2$—NH—C(O)—(CH$_2$)$_8$—C(O)—NH—(CH$_2$)$_2$—NH— | H | H | H | H | | |
| 53 | C—C | —NH—(CH$_2$)$_2$—NH—C(O)—CH$_2$—O—CH$_2$—C(O)—NH—(CH$_2$)$_2$—NH— | —CH$_2$—Z—O—(CH$_2$)$_3$—CH$_3$ Where Z = 1,4-phenyl | H | H | H | | |
| 54 | C—C | —NH—(CH$_2$)$_2$—NH—C(O)—(CH$_2$)$_2$—CH(NH—C(O)—Z)—C(O)—NH—(CH$_2$)$_2$—NH— Where Z = (biphenyl) | H | H | H | H | | |

-continued

C—C COMPOUNDS

| No. | Class | Linker | V1 | V2 | N1 | N2 | R1 | R2 |
|---|---|---|---|---|---|---|---|---|
| 55 | C—C | —NH—$(CH_2)_2$—NH—C(O)—$CH_2$—O—$CH_2$—C(O)—NH—$(CH_2)_2$—NH— | H | H | H | H | | |
| 56 | C—C | —NH—$(CH_2)_2$—NH—C(O)—$CH_2$—O—$CH_2$—C(O)—NH—$(CH_2)_2$—NH— | —$CH_2$—Z Where Z = biphenyl | H | H | H | | |
| 57 | C—C | —NH—$(CH_2)_2$—NH—C(O)—$(CH_2)_3$—C(O)—NH—$(CH_2)_2$—NH— | —$CH_2$—Z Where Z = biphenyl | H | H | H | | |
| 58 | C—C | —NH—$(CH_2)_2$—NH—C(O)—$(CH_2)_3$—C(O)—NH—$(CH_2)_2$—NH— | —$CH_2$—Z Where Z = 4-(4'-chloro) biphenyl | H | H | H | | |
| 59 | C—C | —NH—$(CH_2)_2$—NH—C(O)—$(CH_2)_3$—C(O)—NH—$(CH_2)_2$—NH— | —$(CH_2)_2$—NH—$(CH_2)_5$—$CH_3$ | H | H | H | | |
| 60 | C—C | —NH—$(CH_2)_2$—NH—C(O)—$(CH_2)_3$—C(O)—NH—$(CH_2)_2$—NH— | —$(CH_2)_2$—NH—$CH_2$—Z Where Z = biphenyl | H | H | H | | |
| 61 | C—C | —NH—$(CH_2)_2$—NH—C(NH)—$(CH_2)_6$—C(NH)—NH—$(CH_2)_2$—NH— | H | H | H | H | | |
| 62 | C—C | —NH—$(CH_2)_2$—NH—C(NH)—$CH_2$—C(NH)—NH—$(CH_2)_2$—NH— | H | H | H | H | | |
| 63 | C—C | —NH—$(CH_2)_2$—NH— | —$(CH_2)_2$—NH—$(CH_2)_5$—$CH_3$ | H | H | H | | |
| 64 | C—C | —NH—$(CH_2)_2$—NH— | —$(CH_2)_2$—$NH_2$ | H | H | H | | |
| 65 | C—C | —NH—$(CH_2)_2$—NH—$CH_2$—Z—$CH_2$—NH—$(CH_2)_2$—NH— Where Z = 1,3 phenyl | H | H | H | H | | |

[a]indicates that the substituent is an aglycone

Preparation of other [C—C] Compounds of Formula I

Similarly, other [C—C] compounds of Formula I are prepared following the procedures of Examples 1–7 above, including those where the ligand is optionally substituted vancomycin, optionally substituted N-desmethylvancomycin, or optionally substituted chloroeremomycin.

EXAMPLE 8

Preparation of [V—V] Compounds of Formula I in which Position C is Substituted (1) Preparation of a Compound of Formula (31)

V-[Fmoc-2-aminoethyl] vancomycin (the compound of formula (25) prepared above) (300 mg, 150 μmol) was dissolved in N,N-dimethylformamide. N,N-diisopropylethylamine (65 μL, 370 μmol) was added followed by 1-hydroxybenzotriazole (20 mg, 150 μmol), 3-(dimethylamino)propylamine (30 μL, 240 μmol) and PyBOP (90 mg, 170 μmol). The solution was kept at room temperature for 30 minutes, then dripped into acetonitrile to give a white precipitate. The precipitate was collected by centrifugation and purified by reverse-phase HPLC (50 minutes 10–50% acetonitrile in water containing 0.1% trifluoroacetic acid, elutes at 35 minutes) to give [C]-[3-dimethylamino)propylamino] [V]-[Fmoc-2-aminoethyl] vancomycin a compound of formula (31), as its trifluoroacetic acid salt.

(2) Preparation of a Compound of Formula (32)

To a solution of the compound of formula (31) prepared in step 1 in 2 mL N,N-dimethylformamide was added 0.5 mL piperidine. The solution was left at room temperature for 10 minutes then added dropwise to 15 mL acetonitrile, yielding a white precipitate. The precipitate was collected by centrifugation, washed with ether, air dried and purified by reverse-phase HPLC (50 minutes 2–50% acetonitrile in water containing 0.1% trifluoroacetic acid, elutes at 21 minutes) to give [C]-[3-(dimethylamino)propylamino]-[V]-[2-aminoethyl] vancomycin, a compound of formula (32) as its trifluoroacetic acid salt (177 mg, 92 μmol, 61%).

(3) Preparation of a Compound of Formula I

To the compound of formula (32) prepared above (20 mg, 10 μmol), was added glutaric acid (6) (0.7 mg, 5 μmol) in 50 μL N,N-dimethylformamide followed by 150 μL N,N-dimethylformamide. To the resulting solution was added PyBOP (5.4 mg, 10 μmol) and 1-hydroxybenzotriazole (1.4 mg, 10 μmol) in 50 μL N,N-dimethylformamide followed by N,N-diisopropylethylamine (8.2 μL, 47 μmol). The solution was left at room temperature overnight, then dripped into 15 mL acetonitrile. The resulting precipitate was collected by centrifugation, washed with ether, air dried and purified by reverse-phase HPLC (50 minutes 2–30% acetonitrile in water containing 0.1% trifluoroacetic acid, elutes at 26 minutes) to give [V—V]-pentane-1,5-dioic acid bis-[(2-ethyl)amide]-bis-([C]-3-dimethylaminopropylamino-(vancomycin)), a [V—V] compound of Formula I as its trifluoroacetic acid salt.

EXAMPLE 9

Preparation of a [V—V] Compound of Formula I in which Position C is Substituted (1) Preparation of a Compound of Formula (36)

To a solution of [C]-(3-dimethylaminopropylamino)-[V]-(2-aminoethyl) vancomycin, the compound of formula (32) prepared as above (20 mg, 10 μmol), and glutaric acid mono-9-fluorenylmethyl ester (15) (3.2 mg, 10 μmol) in 200 μL N,N-dimethylformamide was added N,N-diisopropylethylamine (9.1 μL, 52 μmol) followed by PyBOP (5.4 mg, 10 μmol) and 1-hydroxybenzotriazole (1.4 mg, 10 μmol) in 50 uL N,N-dimethylformamide. The resulting solution was kept at room temperature for 80 minutes, then added dropwise to 15 mL of acetonitrile. The solid was filtered off and then dissolved in 500 uL N,N-dimethylformamide, treated with 150 uL piperidine for 1 hour at room temperature and added dropwise to 15 mL acetonitrile. The resulting precipitate was collected by centrifugation, washed with ether, air dried and purified by reverse-phase HPLC (2–30% acetonitrile in water containing 0.1% trifluoroacetic acid) to give [C]-[(3-(dimethylamino)propylamino]-[V]-pentane-1,5-dioic acid (2-aminoethyl)amide)(vancomycin), a compound of formula (36) as its trifluoroacetic acid salt (13.1 mg, 6.4 μmol, 64%).

(2) Preparation of a Compound of Formula (32')

To a solution of the compound of formula (25) prepared as described in Example 6 (30 mg, 15 μmol) in 300 μL of N,N-dimethylformamide was added dodecylamine (4.3 mg, 23 μmol) 20 μL N,N-dimethylformamide followed by N,N-diisopropylethylamine (67 μL, 38 μmol) then 1-hydroxybenzotriazole (20 mg, 150 μmol) and PyBOP (90 mg, 170 μmol) in 40 μL N,N-dimethylformamide. The solution was kept at room temperature for an hour, then dripped into 15 mL of acetonitrile. The resulting precipitate was collected by centrifugation, washed with ether and air dried. It was then dissolved in 1 mL N,N-dimethylformamide, treated with 200 μL piperidine for 10 minutes, then dripped into 15 mL of acetonitrile. The resulting precipitate was collected by centrifugation, washed with ether, air dried and purified by reverse-phase HPLC (50 minutes 10–70% acetonitrile in water containing 0.1% trifluoroacetic acid, elutes at 38 minutes) to give (C)-n-dodecylamino [V]-pentane-1,5-dioic acid (2-aminoethyl)amide)-vancomycin, a compound of formula (32') as its trifluoroacetic acid salt (22.5 mg, 12 μmol, 77%).

(3) Preparation of a Compound of Formula I

The compound of formula (36) (10.8 mg, 5.3 μmol) and the compound of formula (32') (10.0 mg, 5.3 μmol) and N,N-diisopropylethylamine (6.5 μL, 37 μmol), prepared as above, were dissolved in 200 μL of N,N-dimethylformamide. A solution of PyBOP (2.8 mg, 5.4 μmol) and 1-hydroxybenzotriazole (0.7 mg, 5.2 μmol) in 20 μL of N,N-dimethylformamide was added and the resulting solution left for 1 hour at room temperature. PyBOP (0.7 mg, 1.3 μmol) and 1-hydroxybenzotriazole (0.2 mg, 1.3 μmol) in 5 μL of N,N-dimethylformamide was added. The solution was left for 1 hour and dripped into 15 mL acetonitrile. The resulting precipitate was collected by centrifugation, washed with ether, air dried and purified by reverse-phase HPLC (10–50% acetonitrile in water containing 0.1% trifluoroacetic acid) to give [C]-(3-dimethylaminopropylamino)-[V—V]-pentane-1,5-dioic acid bis-[(2-aminoethyl)amide]-[C']-(n-dodecylamino)-bis-(vancomycin), a compound of Formula I as its trifluoroacetic acid salt.

Preparation of other [V—V] Compounds of Formula I

Following the procedures of Examples 8 and 9, the following [V—V] compounds of Formula I were prepared. It should be noted that "Class" denotes the point of attachment of the linker; C1, N1, and R1 represent the point of attachment with respect to the first glycopeptide; C2, N2, and R2 represent the point of attachment with respect to the second glycopeptide.

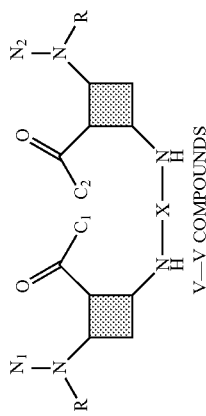

V–V COMPOUNDS

| # | Class | Linker | N1 | N2 | C1 | C2 | R1 | R2 |
|---|---|---|---|---|---|---|---|---|
| 1 | V–V | —$(CH_2)_2$—NH—C(O)—$(CH_2)_3$—C(O)—NH—$(CH_2)_2$— | H | H | —NH—$(CH_2)_3$—N$(CH_3)_2$ | —NH—$(CH_2)_3$—N$(CH_3)_2$ | — | — |
| 2 | V–V | —$(CH_2)_2$—NH—C(O)—$(CH_2)_3$—C(O)—NH—$(CH_2)_2$— | H | H | OH | OH | — | — |
| 3 | V–V | —$(CH_2)_2$—NH—C(O)—Z—C(O)—NH—$(CH_2)_2$— Where Z = 1,4-phenyl | H | H | —NH—$(CH_2)_3$—N$(CH_3)_2$ | —NH—$(CH_2)_3$—N$(CH_3)_2$ | — | — |
| 4 | V–V | —$(CH_2)_2$—NH—C(O)—Z—C(O)—NH—$(CH_2)_2$— Where Z = 1,3-phenyl | H | H | —NH—$(CH_2)_3$—N$(CH_3)_2$ | —NH—$(CH_2)_3$—N$(CH_3)_2$ | — | — |
| 5 | V–V | —$(CH_2)_2$—NH—C(O)—$(CH_2)_4$—C(O)—NH—$(CH_2)_2$— | H | H | —NH—$(CH_2)_3$—N$(CH_3)_2$ | —NH—$(CH_2)_3$—N$(CH_3)_2$ | — | — |
| 6 | V–V | —$(CH_2)_2$—NH—C(O)—Z—O—Z—C(O)—NH—$(CH_2)_2$— Where Z = 1,4-phenyl | H | H | —NH—$(CH_2)_3$—N$(CH_3)_2$ | —NH—$(CH_2)_3$—N$(CH_3)_2$ | — | — |
| 7 | V–V | —$(CH_2)_2$—NH—C(O)—$(CH_2)_3$—C(O)—NH—$(CH_2)_2$— | H | H | —NH—$(CH_2)_{11}$—CH$_3$ | —NH—$(CH_2)_{11}$—CH$_3$ | — | — |
| 8 | V–V | —$(CH_2)_2$—NH—C(O)—$(CH_2)_3$—C(O)—NH—$(CH_2)_2$— | H | H | —NH—$(CH_2)_3$—NH—C(O)—Z Where Z = biphenyl | —NH—$(CH_2)_3$—NH—C(O)—Z Where Z = biphenyl | — | — |
| 9 | V–V | —$(CH_2)_2$—NH—C(O)—$(CH_2)_3$—C(O)—NH—$(CH_2)_2$— | H | H | —NH—$(CH_2)_3$—N$(CH_3)_2$ | —NH—$(CH_2)_3$—N$(CH_3)_2$ | — | — |
| 10 | V–V | —$(CH_2)_2$—NH—C(O)—CH$_2$—C(O)—NH—$(CH_2)_2$— | H | H | —NH—$(CH_2)_3$—N$(CH_3)_2$ | —NH—$(CH_2)_3$—N$(CH_3)_2$ | — | — |
| 11 | V–V | —$(CH_2)_2$—NH—C(O)—$(CH_2)_2$—C(O)—NH—$(CH_2)_2$— | H | H | —NH—$(CH_2)_3$—N$(CH_3)_2$ | —NH—$(CH_2)_3$—N$(CH_3)_2$ | — | — |
| 12 | V–V | —$(CH_2)_2$—NH—C(O)—$(CH_2)_6$—C(O)—NH—$(CH_2)_2$— | H | H | —NH—$(CH_2)_3$—N$(CH_3)_2$ | —NH—$(CH_2)_3$—N$(CH_3)_2$ | — | — |
| 13 | V–V | —$(CH_2)_2$—NH—C(O)—$(CH_2)_{10}$—C(O)—NH—$(CH_2)_2$— | H | H | —NH—$(CH_2)_3$—N$(CH_3)_2$ | —NH—$(CH_2)_3$—N$(CH_3)_2$ | — | — |
| 14 | V–V | —$(CH_2)_2$—NH—C(O)—$(CH_2)_2$—CH(NH—C(O)—$(CH_2)_8$—CH$_3$)—C(O)—NH—$(CH_2)_2$— | H | H | —NH—$(CH_2)_3$—N$(CH_3)_2$ | —NH—$(CH_2)_3$—N$(CH_3)_2$ | — | — |
| 15 | V–V | —$(CH_2)_2$—NH—C(O)—$(CH_2)_3$—C(O)—NH—$(CH_2)_2$— | H | H | —NH—$(CH_2)_{11}$—CH$_3$ | —NH—$(CH_2)_{11}$—CH$_3$ | — | — |
| 16 | V–V | —$(CH_2)_2$—NH—C(O)—Z—C(O)—NH—$(CH_2)_2$— Where Z = 1,2-phenyl | H | H | —NH—$(CH_2)_3$—N$(CH_3)_2$ | —NH—$(CH_2)_3$—N$(CH_3)_2$ | — | — |
| 17 | V–V | —$(CH_2)_2$—NH—C(O)—CH$_2$—O—CH$_2$—C(O)—NH—$(CH_2)_2$— | H | H | —NH—$(CH_2)_3$—N$(CH_3)_2$ | —NH—$(CH_2)_3$—N$(CH_3)_2$ | — | — |
| 18 | V–V | —$(CH_2)_2$—NH—C(O)—Z—C(O)—NH—C(O)—NH—$(CH_2)_2$— Where Z = 5-(n-octadecyloxy)-1,3-phenyl | H | H | —NH—$(CH_2)_3$—N$(CH_3)_2$ | —NH—$(CH_2)_3$—N$(CH_3)_2$ | — | — |
| 19 | V–V | —$(CH_2)_2$—NH—C(O)—$(CH_2)_5$—C(O)—NH—$(CH_2)_2$— | H | H | —NH—$(CH_2)_3$—N$(CH_3)_2$ | —NH—$(CH_2)_3$—N$(CH_3)_2$ | — | — |
| 20 | V–V | —$(CH_2)_2$—NH—C(O)—$(CH_2)_2$—CH(NH—C(O)—Z)—C(O)—NH—$(CH_2)_2$— Where Z = biphenyl | H | H | —NH—$(CH_2)_3$—N$(CH_3)_2$ | —NH—$(CH_2)_3$—N$(CH_3)_2$ | — | — |
| 21 | V–V | —$(CH_2)_2$—NH—C(O)—$(CH_2)_{11}$—C(O)—NH—$(CH_2)_2$— | H | H | —NH—$(CH_2)_3$—N$(CH_3)_2$ | —NH—$(CH_2)_3$—N$(CH_3)_2$ | — | — |
| 22 | V–V | —$(CH_2)_2$—NH—C(O)—$(CH_2)_8$—C(O)—NH—$(CH_2)_2$— | H | H | —NH—$(CH_2)_3$—N$(CH_3)_2$ | —NH—$(CH_2)_3$—N$(CH_3)_2$ | — | — |
| 24 | V–V | —$(CH_2)_2$—NH—C(O)—Z—C(O)—NH—$(CH_2)_2$— Where Z = 1,3-phenyl | H | H | —NH—$(CH_2)_8$—CH$_3$ | —NH—$(CH_2)_8$—CH$_3$ | — | — |
| 25 | V–V | —$(CH_2)_2$—NH—C(O)—Z—C(O)—NH—$(CH_2)_2$— Where Z = 1,3-phenyl | H | H | —NH—$(CH_2)_5$—CH$_3$ | —NH—$(CH_2)_5$—CH$_3$ | — | — |
| 26 | V–V | —$(CH_2)_2$—NH—C(O)—$(CH_2)_{10}$—C(O)—NH—$(CH_2)_2$— | H | H | —NH—$(CH_2)_8$—CH$_3$ | —NH—$(CH_2)_8$—CH$_3$ | — | — |

-continued

V—V COMPOUNDS

| # | Class | Linker | N1 | N2 | C1 | C2 | R1 | R2 |
|---|---|---|---|---|---|---|---|---|
| 27 | V—V | —(CH$_2$)$_2$—NH—C(O)—(CH$_2$)$_{10}$—C(O)—NH—(CH$_2$)$_2$— | H | H | —NH—(CH$_2$)$_5$—CH$_3$ | —NH—(CH$_2$)$_5$—CH$_3$ | — | — |
| 28 | V—V | —(CH$_2$)$_2$—NH—C(O)—Z—C(O)—NH—(CH$_2$)$_2$— Where Z = 5-(n-butyloxy)-1,3-phenyl | H | H | —NH—(CH$_2$)$_3$—N(CH$_3$)$_2$ | —NH—(CH$_2$)$_3$—N(CH$_3$)$_2$ | — | — |
| 29 | V—V | —(CH$_2$)$_2$—NH—C(O)—Z—C(O)—13 NH—(CH$_2$)$_2$— Where Z = 5-(n-octyloxy)-1,3-phdmyl | H | H | —NH—(CH$_2$)$_3$—N(CH$_3$)$_2$ | —NH—(CH$_2$)$_{-3}$—N(CH$_3$)$_2$ | — | — |
| 30 | V—V | —(CH$_2$)$_2$—NH—C(O)—Z—C(O)—NH—(CH$_2$)$_2$— Where Z = 5-(benzyloxy)-1,3-phenyl | H | H | —NH—(CH$_2$)$_3$—N(CH$_3$)$_2$ | —NH—(CH$_2$)$_3$—N(CH$_3$)$_2$ | — | — |
| 31 | V—V | —(CH$_2$)$_2$—NH—C(O)—(CH$_2$)$_8$—(CH=CH)—C(O)—NH—(CH$_2$)$_2$— | H | H | —NH—(CH$_2$)$_3$—N(CH$_3$)$_2$ | —NH—(CH$_2$)$_3$—N(CH$_3$)$_2$ | — | — |
| 32 | V—V | —(CH$_2$)$_2$—NH—C(O)—(CH$_2$)$_2$—CH(NH—C(O)—(CH$_2$)$_{12}$—CH$_3$)—C(O)—NH—(CH$_2$)$_2$— | H | H | —NH—(CH$_2$)$_3$—N(CH$_3$)$_2$ | —NH—(CH$_2$)$_3$—N(CH$_3$)$_2$ | — | — |
| 33 | V—V | —(CH$_2$)$_2$—NH—C(O)—(CH$_2$)$_2$—CH(NH—C(O)—Z—C(O)—NH—(CH$_2$)$_2$— Where Z = 4-(n-octyl)-phenyl | H | H | —NH—(CH$_2$)$_3$—N(CH$_3$)$_2$ | —NH—(CH$_2$)$_3$—N(CH$_3$)$_2$ | — | — |
| 34 | V—V | —(CH$_2$)$_2$—NH—C(O)—(CH$_2$)$_9$—C(O)—NH—(CH$_2$)$_2$— | H | H | —NH—(CH$_2$)$_3$—N(CH$_3$)$_2$ | —NH—(CH$_2$)$_3$—N(CH$_3$)$_2$ | — | — |
| 35 | V—V | —(CH$_2$)$_2$—NH—C(O)—(CH$_2$)$_2$—C(O)—NH—(CH$_2$)$_2$— | H | H | —NH—(CH$_2$)$_8$—CH$_3$ | —NH—(CH$_2$)$_8$—CH$_3$ | — | — |
| 36 | V—V | —(CH$_2$)$_2$—NH—C(O)—(CH$_2$)$_2$—C(O)—NH—(CH$_2$)$_2$— | H | H | —NH—(CH$_2$)$_{11}$—CH$_3$ | —NH—(CH$_2$)$_{11}$—CH$_3$ | — | — |
| 37 | V—V | —(CH$_2$)$_2$—NH—C(O)—(CH$_2$)$_2$—NH—C(O)—(CH$_2$)$_3$—C(O)—NH—(CH$_2$)$_2$— | H | H | —NH—(CH$_2$)$_2$—COOH | —NH—(CH$_2$)$_3$—N(CH$_3$)$_2$ | — | — |
| 38 | V—V | —CH$_2$—Z—O—(CH$_2$)$_6$—O—Z—CH$_2$— Where Z = 1,4-phenyl | H | H | OH | OH | — | — |
| 39 | V—V | —(CH$_2$)$_2$—NH—C(O)—(CH$_2$)$_2$—CH(NH—C(O)—Z—C(O)—NH—(CH$_2$)$_2$— Where Z = biphenyl | H | H | —NH—(CH$_2$)$_3$—N(CH$_3$)$_2$ | —NH—(CH$_2$)$_3$—N(CH$_3$)$_2$ | — | — |
| 40 | V—V | —(CH$_2$)$_2$—Z—O—(CH$_2$)$_6$—O—Z—CH$_2$— Where Z = 1,4-phenyl | H | H | —NH—(CH$_2$)$_2$—O—CH$_3$ | —NH—(CH$_2$)$_2$—O—CH$_3$ | — | — |
| 41 | V—V | —(CH$_2$)$_2$—Z—O—(CH$_2$)$_6$—O—Z—CH$_2$— Where Z = 1,4-phenyl | H | H | —NH—(CH$_2$)$_3$—N(CH$_3$)$_2$ | —NH—(CH$_2$)$_3$—N(CH$_3$)$_2$ | — | — |
| 42 | V—V | —CH$_2$—Z—CH$_2$—NH—C(O)—Y—C(O)—NH—CH$_2$—Z—CH$_2$— Where Z = 1,4-phenyl and Y = 1,3-phenyl | H | H | —NH—(CH$_2$)$_3$—N(CH$_3$)$_2$ | —NH—(CH$_2$)$_3$—N(CH$_3$)$_2$ | — | — |
| 43 | V—V | —CH$_2$—Z—CH$_2$—NH—C(O)—(CH$_2$)$_7$—C(O)—NH—CH$_2$—Z—CH$_2$— Where Z = 1,4-phenyl and Y = 1,3-phenyl | H | H | —NH—(CH$_2$)$_3$—N(CH$_3$)$_2$ | —NH—(CH$_2$)$_3$—N(CH$_3$)$_2$ | — | — |
| 44 | V—V | —(CH$_2$)$_2$—NH—C(NH)—(CH$_2$)$_6$—C(NH)—NH—(CH$_2$)$_2$— | H | H | —NH—(CH$_2$)$_3$—N(CH$_3$)$_2$ | —NH—(CH$_2$)$_3$—N(CH$_3$)$_2$ | — | — |
| 45 | V—V | —(CH$_2$)$_2$—NH—C(NH)—CH$_2$—C(NH)—NH—(CH$_2$)$_2$— | H | H | —NH—(CH$_2$)$_3$—N(CH$_3$)$_2$ | —NH—(CH$_2$)$_3$—N(CH$_3$)$_2$ | — | — |

Preparation of other [V—V] Compounds of Formula I

Similarly, other [V—V] compounds of Formula I are prepared following the procedures of Examples 8 and 9 above, including those where the ligand is optionally substituted vancomycin, optionally substituted N-desmethylvancomycin, or optionally substituted chloroeremomycin.

EXAMPLE 10

Preparation of an [N—N] Compound of Formula I (1) Preparation of a Compound of Formula (41)

Vancomycin hydrochloride (4.00 g, 2.60 mmol) was suspended in 40 mL of 1,3-dimethyl-3,4,5,6-tetrahydro-2-(1H)-pyrimidinone and heated to 70° C. for 15 minutes. N-(9-fluorenylmethoxycarbonyl)-aminoacetaldehyde (7) (720 mg, 2.6 mmol) was added and the mixture was heated at 70° C. for one hour. Sodium cyanoborohydride (160 mg, 2.5 mmol) in 2 mL methanol was added and the mixture was heated at 70° C. for 2 hours, then cooled to room temperature. The reaction solution was added dropwise to 20 mL of acetonitrile, giving a precipitate that was collected by centrifugation. The precipitate was purified by reverse-phase HPLC on a Ranin C18 Dynamax column (2.5 cm×25 cm, 8 µm particle size), at 10 mL/min flow rate using 0.045% TFA in water as buffer A and 0.045% TFA in acetonitrile as buffer B (HPLC gradient of 10–70% B over 90 minutes), which yielded [N]-[Fmoc]-2 aminoethylvancomycin, a compound of formula (41) as its trifluroacetate salt. MS calculated: MH$^+$, 1715; Found, 1715.

(2) Preparation of a Compound of Formula (42)

The compound of formula (41) obtained above (291 mg, 150 µmol) was dissolved in 3 mL of DMF. 3-(dimethylamino)propylamine (1) (28.3 µL, 225 µmol) was added, followed by the addition of PyBOP (85.8 mg, 165 µmol), HOBt (20.3 mg, 150 µmol) and Hunig's base (65.0 µL, 375 µmol). The reaction solution was stirred for one hour then). The reaction solution was stirred for 1 hour and then added dropwise to 20 mL of acetonitrile giving a precipitate, which was collected by centrifugation, to give compound of formula [C]-3-(dimethylamino)propylamino)-[N]-[Fmoc]-2-aminoethylvancomycin (42) as a white solid. MS calculated: MH$^+$, 1800; Found, 1800.

(3) Preparation of a Compound of Formula (43)

The compound of formula (42) obtained above was dissolved in 1 mL of DMF, and 100 µL of piperidine added to the solution. The solution was allowed to stand at room temperature for 30 minutes and the course of the reaction was followed by mass spectroscopy. The reaction solution was added dropwise to 20 mL of acetonitrile, giving a precipitate that was collected by centrifugation. The precipitate was purified by reverse-phase HPLC on a Ranin C18 Dynamax column (2.5 cm×25 cm, 8 µm particle size), at 10 mL/min flow rate using 0.045% TFA in water as buffer A and 0.045% TFA in acetonitrile as buffer B (HPLC gradient of 2–50% B over 90 minutes), which yielded [C]-3-(dimethylamino)propylamino)-[N]-2-aminoethylvancomycin, a compound of formula (43), as its trifluroacetate salt. MS calculated: MH$^+$, 1578; Found, 1578.

Preparation of a Compound of Formula I

The compound of formula (43) prepared above (20.0 mg, 12.7 µmol) was dissolved in 500 µL of DMF. HO$_2$C—(CH$_2$)$_2$—NH—C(O)—(CH$_2$)$_2$—NH—C(O)—(CH$_2$)$_3$—C(O)—NH—(CH$_2$)$_2$—C(O)—NH(CH$_2$)$_2$—CO$_2$H (6) (2.64 mg, 6.34 µmol) was added, followed by PyBOP (8.24 mg, 15.8 µmol), HOBt (2.13 mg, 15.8 µmol) and Hunig's base (8.8 µL, 51.0 µmol). The reaction solution as added dropwise to 20 mL of acetonitrile, giving a precipitate that was collected by centrifugation. The precipitate was purified by reverse-phase HPLC on a Ranin C18 Dynamax column (2.5 cm×25 cm, 8 µL particle size), at 10 mL/min flow rate using 0.045% TFA in water as buffer A and 0.045% TFA in acetonitrile as buffer B (HPLC gradient of 2–50% B over 90 minutes), which yielded a [N—N] Linked compound of Formula I as its trifluoroacetate salt. MS calculated: MH$^+$, 3533; Found, 3533.

Preparation of other [N—N] Compounds of Formula I

Following the procedures of Example 10, the following [N—N] compounds of Formula I were prepared. It should be noted that "Class" denotes the point of attachment of the linker; C1, V1, and R1 represent the point of attachment with respect to the first glycopeptide; C2, V2, and R2 represent the point of attachment with respect to the second glycopeptide.

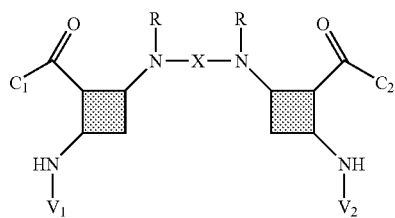

N—N COMPOUNDS

| No. | Class | Linker | C1 | C2 | V1 | V2 | R1 | R2 |
|---|---|---|---|---|---|---|---|---|
| 1 | N—N | —CH$_2$—Z—O—(CH$_2$)$_6$—O—Z—CH$_2$— Where Z = 1,4 phenyl | OH | OH | H | H | — | — |

Preparation of other [N—N] Compounds of Formula I

Following the procedures of Example 10, other [N—N] compounds of Formula I are prepared, including those where the ligand is optionally substituted vancomycin, optionally substituted N-desmethylvancomycin, or optionally substituted chloroeremomycin.

EXAMPLE 11

Preparation of an Aglycone [O—O] Compound of Formula I (1) Preparation of a Compound of Formula (47)

Vancomycin hydrochloride hydrate (10 g, 6.4 mmol) was dissolved in 100 mL of dimethyl sulfoxide (DMSO) and 3-(dimethylamino)propylamine (3.2 mL, 26 mmol) was added. PyBOP (3.3 g, 6.4 mmol) and 1-hydroxybenzotriazole (HOBT, 0.9 g, 6.4 mmol) dissolved in 100 mL N,N-dimethylformamide (DMF) was added dropwise at room temperature. The reaction was stirred for one hour and dripped into acetonitrile to give a white precipitate, which was filtered and washed with acetonitrile, ether and dried under vacuum to give a syrup of crude [C]-3-(dimethylamino)propyl amino vancomycin (46).

A portion of this syrup was dissolved in 100 mL trifluoroacetic acid (TFA), heated at 323K for 2 hours, cooled to room temperature and added dropwise to ether, resulting in a green precipitate. The precipitate was collected by filtration, dried under vacuum and purified by reverse-phase HPLC (2–50% acetonitrile in water containing 0.1% TFA) to give [C]-3-(dimethylamino)propyl amino vancomycin aglycone, a compound of formula (47), as its TFA salt.

(2) Preparation of an [O—O] Compound of Formula I

[C]-3-(dimethylamino)propyl amino vancomycin aglycone trifluoroacetate (32 mg, 22 umol) was dissolved in 320 uL DMF and potassium carbonate (35 mg, 250 umol) was added. The suspension was stirred for 30 minutes at room temperature then 1,3-dibromopropane (0.9 uL, 9 umol) was added in 20 uL DMF. The suspension was stirred for 36 hours and diluted with 1 mL 10% acetic acid in water. Reverse-phase HPLC purification yielded [O—O]-1,3-propane-bis([C]-3-(dimethylamino)propylamino-(vancomycin), as its trifluoroacetate salt.

EXAMPLE 12

Preparation of an Aglycone [O—O] Compound of Formula I (1) Preparation of a Compound of Formula (52)

[C]-3-(dimethylamino)propylamide vancomycin aglycone (47), as its trifluoroacetate salt (500 mg, 340 umol) was dissolved in 5 mL DMF and potassium carbonate (500 mg, 3.6 mmol) was added. The mixture was stirred for 15 minutes at room temperature then tert-butyl N-(2-bromoethyl)carbamate (77 mg, 340 umol) was added. The mixture was stirred at room temperature for 24 hours, then tert-butyl N-(2-bromoethyl)carbamate (70 mg, 310 umol) was added. The mixture was stirred at room temperature for 7 hours then dripped into ether giving a precipitate that was collected by centrifugation, washed with acetonitrile and dissolved in 5:1:2 water/acetic acid/acetonitrile. This solution was purified by reverse-phase HPLC giving vancomycin [C]-dimethylaminopropylamide [O]-2-(N-t-BOC-amino)ethoxy aglycone as the trifluoroacetate salt, which was treated with 1 mL TFA for 30 minutes at room temperature. Reverse-phase HPLC purification yielded [C]-3-(dimethylamino) propylamino [O]-(2-aminoethyl) vancomycin aglycone (52) as the trifluoroacetate salt.

(2) Preparation of a Compound of Formula I

Succinic acid (0.18 mg, 1.5 μmol), HATU (1.2 mg, 3 μmol) and HOAT (0.4 mg, 3 umol) were dissolved in 40 μL DMF at room temperature. N,N-diisopropylethylamine (0.5 μL, 3 μmol) was added, the solution left for 10 minutes, then added to a mixture of vancomycin [C]-dimethylaminopropylamide [O]-(2-aminoethoxy) aglycone (52) as its trifluoroacetate salt (5 mg, 3 μmol) and N,N-diisopropylethylamine (2,2 μL, 12 μmol) in 100 μL DMF. This mixture was left at room temperature for a further 20 minutes, then dripped into acetonitrile giving a white precipitate, which was collected by centrifugation. Reverse-phase HPLC gave [O—O]-butane-1,4-dioic bis-[(2-ethyl)amide][C,C'])-bis-([C]-3-(dimethylamino)propylamino)-bis(vancomycin aglycone), a compound of Formula I, as its trifluoroacetate salt.

EXAMPLE 13

Preparation of an Aglycone [O—O] Compound of Formula I (1) Preparation of a Compound of Formula (57)

A compound of formula (47) prepared as shown in Example 12 above (500 mg, 340 umol) was dissolved in 5 mL DMF and potassium carbonate (500 mg, 3.6 mmol) was added. The mixture was stirred for 15 minutes at room temperature then tert-butyl bromoacetate (12) (46 μL, 310 μmol) was added. The mixture was stirred at room temperature for 1 hour, then dripped into ether giving a precipitate that was collected by centrifugation, washed with acetonitrile and dissolved in 10:1 water/acetic acid. This solution was purified by reverse-phase HPLC giving (in order of elution) recovered starting material, a product formed by alkylation on the dimethylamino group, followed by desired product (i.e. the compound of formula (56), its BOC derivative), which was treated with 1 mL TFA for 20 minutes at room temperature. Reverse-phase HPLC purification yielded [C]-3-(dimethylamino)propyl amino [O]-(2-carboxymethyl) vancomycin aglycone, the compound of formula (57), as its trifluoroacetate salt.

(2) Preparation of a Compound of Formula I

At room temperature the compound of formula (57), prepared as shown above (7 mg, 5 umol), was dissolved in 160 μL DMF, N,N-diisopropylethylamine (3.5 μL, 20 μmol) and 1,3-diaminopropane (2) (0.2 μL, 2.5 μmol) were added followed by PyBOP (2.6 mg, 5 μmol) and HOBT (0.7 mg, 5 μmol) in 20 μL DMF. The mixture was left for 110 minutes then dripped into acetonitrile giving a white precipitate. The precipitate was collected by centrifugation and purified by reverse-phase HPLC giving [O—O]-1,3-bis-(2-acetylamino)propane-bis-([C]-3-(dimethylamino)propylamino)-(vancomycin aglycone), a compound of Formula I, as its trifluoroacetate salt.

(4) Preparation of other Compounds of Formula I

Accordingly, following the procedures of Examples 11–13, other aglycone [O—O] compounds of Formula I were prepared.

O-O COMPOUNDS

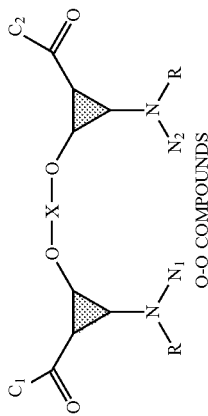

| No. | Class | Linker | C1 | C2 | N1 | N2 | R1 | R2 |
|---|---|---|---|---|---|---|---|---|
| 1 | O-O | —CH$_2$—C(O)—NH—(CH$_2$)$_3$—NH—C(O)—CH$_2$— | —NH—(CH$_2$)$_3$—N(CH$_3$)$_2$ | —NH—(CH$_2$)$_3$—N(CH$_3$)$_2$ | H | H | — | — |
| 2 | O-O | —CH$_2$—C(O)—NH—(CH$_2$)$_6$—NH—C(O)—CH$_2$— | —NH—(CH$_2$)$_3$—N(CH$_3$)$_2$ | —NH—(CH$_2$)$_3$—N(CH$_3$)$_2$ | H | H | — | — |
| 3 | O-O | —CH$_2$—C(O)—NH—(CH$_2$)$_9$—NH—C(O)—CH$_2$— | —NH—(CH$_2$)$_3$—N(CH$_3$)$_2$ | —NH—(CH$_2$)$_3$—N(CH$_3$)$_2$ | H | H | — | — |
| 4 | O-O | —(CH$_2$)$_3$— | —NH—(CH$_2$)$_3$—N(CH$_3$)$_2$ | —NH—(CH$_2$)$_3$—N(CH$_3$)$_2$ | H | H | — | — |
| 5 | O-O | —(CH$_2$)$_2$—NH—C(O)—(CH$_2$)$_2$—C(O)—NH—(CH$_2$)$_2$— | —NH—(CH$_2$)$_3$—N(CH$_3$)$_2$ | —NH—(CH$_2$)$_3$—N(CH$_3$)$_2$ | H | H | — | — |
| 6 | O-O | —(CH$_2$)$_2$—NH—C(O)—(CH$_2$)$_3$—C(O)—NH—(CH$_2$)$_2$— | —NH—(CH$_2$)$_3$—N(CH$_3$)$_2$ | —NH—(CH$_2$)$_3$—N(CH$_3$)$_2$ | H | H | — | — |
| 7 | O-O | —(CH$_2$)$_6$— | —NH—(CH$_2$)$_3$—N(CH$_3$)$_2$ | —NH—(CH$_2$)$_3$—N(CH$_3$)$_2$ | H | H | — | — |
| 8 | O-O | —(CH$_2$)$_{10}$— | —NH—(CH$_2$)$_3$—N(CH$_3$)$_2$ | —NH—(CH$_2$)$_3$—N(CH$_3$)$_2$ | H | H | — | — |
| 9 | O-O | —(CH$_2$)$_{12}$— | —NH—(CH$_2$)$_3$—N(CH$_3$)$_2$ | —NH—(CH$_2$)$_3$—N(CH$_3$)$_2$ | H | H | — | — |
| 10 | O-O | —CH$_2$—Z—CH$_2$— Where Z = 1,2-phenyl | —NH—(CH$_2$)$_3$—N(CH$_3$)$_2$ | —NH—(CH$_2$)$_3$—N(CH$_3$)$_2$ | H | H | — | — |
| 11 | O-O | —CH$_2$—Z—CH$_2$— Where Z = 1,3 phenyl | —NH—(CH$_2$)$_3$—N(CH$_3$)$_2$ | —NH—(CH$_2$)$_3$—N(CH$_3$)$_2$ | H | H | — | — |
| 12 | O-O | —CH$_2$—Z—CH$_2$— Where Z = 1,3 phenyl | —NH—(CH$_2$)$_3$—N(CH$_3$)$_2$ | —NH—(CH$_2$)$_3$—N(CH$_3$)$_2$ | H | H | — | — |
| 13 | O-O | —(CH$_2$)$_2$—O—(CH$_2$)$_2$— | —NH—(CH$_2$)$_2$—O—CH$_3$ | —NH—(CH$_2$)$_2$—O—CH$_3$ | H | H | — | — |
| 14 | O-O | —CH$_2$—C(O)—NH—(CH$_2$)$_2$—NH—C(O)—CH$_2$— | —NH—(CH$_2$)$_3$—N(CH$_3$)$_2$ | —NH—(CH$_2$)$_3$—N(CH$_3$)$_2$ | H | H | — | — |
| 15 | O-O | —CH$_2$—C(O)—NH—(CH$_2$)$_3$—NH—C(O)—CH$_2$— | —NH—(CH$_2$)$_2$—O—CH$_3$ | —NH—(CH$_2$)$_2$—O—CH$_3$ | H | H | — | — |
| 16 | O-O | —CH$_2$—C(O)—NH—(CH$_2$)$_4$—NH—C(O)—CH$_2$— | —NH—(CH$_2$)$_3$—N(CH$_3$)$_2$ | —NH—(CH$_2$)$_3$—N(CH$_3$)$_2$ | H | H | — | — |
| 17 | O-O | —(CH$_2$)$_2$—NH—C(O)—CH$_2$— | —NH—(CH$_2$)$_3$—N(CH$_3$)$_2$ | —NH—(CH$_2$)$_3$—N(CH$_3$)$_2$ | H | H | — | — |
| 18 | O-O | —(CH$_2$)$_5$— | —NH—(CH$_2$)$_3$—N(CH$_3$)$_2$ | —NH—(CH$_2$)$_3$—N(CH$_3$)$_2$ | H | H | — | — |
| 19 | O-O | —(CH$_2$)$_2$—O—(CH$_2$)$_2$— | —NH—(CH$_2$)$_3$—N(CH$_3$)$_2$ | —NH—(CH$_2$)$_3$—N(CH$_3$)$_2$ | H | H | — | — |
| 20 | O-O | —(CH$_2$)$_2$—N(CH$_3$)—(CH$_2$)$_2$— | —NH—(CH$_2$)$_3$—N(CH$_3$)$_2$ | —NH—(CH$_2$)$_3$—N(CH$_3$)$_2$ | H | H | — | — |
| 21 | O-O | —(CH$_2$)$_4$— | —NH—(CH$_2$)$_3$—N(CH$_3$)$_2$ | —NH—(CH$_2$)$_3$—N(CH$_3$)$_2$ | H | H | — | — |
| 22 | O-O | —(CH$_2$)$_2$—NH—C(O)—Z—C(O)—NH—(CH$_2$)$_2$— Where Z = 1,2 phenyl | —NH—(CH$_2$)$_3$—N(CH$_3$)$_2$ | —NH—(CH$_2$)$_3$—N(CH$_3$)$_2$ | H | H | — | — |
| 23 | O-O | —(CH$_2$)$_2$—NH—C(O)—Z—C(O)—NH—(CH$_2$)$_2$— Where Z = 1,3 phenyl | —NH—(CH$_2$)$_3$—N(CH$_3$)$_2$ | —NH—(CH$_2$)$_3$—N(CH$_3$)$_2$ | H | H | — | — |
| 24 | O-O | —(CH$_2$)$_2$—NH—C(O)—Z—C(O)—NH—(CH$_2$)$_2$— Where Z = 1,4 phenyl | —NH—(CH$_2$)$_3$—N(CH$_3$)$_2$ | —NH—(CH$_2$)$_3$—N(CH$_3$)$_2$ | H | H | — | — |
| 25 | O-O | —CH$_2$—C(O)—NH—CH(C(O)—O—Z)—(CH$_2$)$_2$—NH—C(O)—CH$_2$— Where Z = 9-fluorenylmethyl | —NH—(CH$_2$)$_3$—N(CH$_3$)$_2$ | —NH—(CH$_2$)$_3$—N(CH$_3$)$_2$ | H | H | — | — |
| 26 | O-O | —CH$_2$—C(O)—NH—CH(COOH)—(CH$_2$)$_2$—NH—C(O)—CH$_2$— | —NH—(CH$_2$)$_3$—N(CH$_3$)$_2$ | —NH—(CH$_2$)$_3$—N(CH$_3$)$_2$ | H | H | — | — |
| 27 | O-O | —CH$_2$—C(O)—NH—(CH$_2$)$_5$—CH$_3$)—(CH$_2$)$_2$—NH—C(O)—CH$_2$— | —NH—(CH$_2$)$_3$—N(CH$_3$)$_2$ | —NH—(CH$_2$)$_3$—N(CH$_3$)$_2$ | H | H | — | — |
| 28 | O-O | —CH$_2$—C(O)—NH—(CH$_2$)$_2$—NH—C(O)—CH$_2$— | —NH—(CH$_2$)$_3$—N(CH$_3$)$_2$ | —NH—(CH$_2$)$_3$—N(CH$_3$)$_2$ | H | H | — | — |

-continued

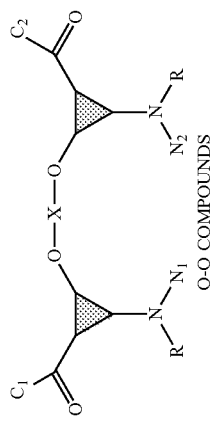

O-O COMPOUNDS

| No. | Class | Linker | C1 | C2 | N1 | N2 | R1 | R2 |
|---|---|---|---|---|---|---|---|---|
| 30 | O-O | —CH₂—C(O)—NH—CH(C(O)—NH—(CH₂)₈—CH₃)—(CH₂)₂—NH—C(O)—CH₂— | —NH—(CH₂)₃—N(CH₃)₂ | —NH—(CH₂)₃—N(CH₃)₂ | H | H | — | — |
| 31 | O-O | —CH₂—C(O)—NH—CH(C(O)—NH—(CH₂)₁₁—CH₃)—(CH₂)₂—NH—C(O)—CH₂— | —NH—(CH₂)₃—N(CH₃)₂ | —NH—(CH₂)₃—N(CH₃)₂ | H | H | — | — |
| 32 | O-O | —CH₂—C(O)—NH—CH(C(O)—NH—Z)—(CH₂)₂—NH—C(O)—CH₂— Where Z = —CH₂—(CH(OH))₄—CH₂OH | —NH—(CH₂)₃—N(CH₃)₂ | —NH—(CH₂)₃—N(CH₃)₂ | H | H | — | — |
| 33 | O-O | —CH₂—C(O)—NH—CH(C(O)—NH—(CH₂)₃—Z)—(CH₂)₂—NH—C(O)—CH₂— Where Z = N-morpholino | —NH—(CH₂)₃—N(CH₃)₂ | —NH—(CH₂)₃—N(CH₃)₂ | H | H | — | — |
| 34 | O-O | —CH₂—C(O)—NH—CH(C(O)—NH—(CH₂)₄—Z)—(CH₂)₂—NH—C(O)—CH₂— Where Z = phenyl | —NH—(CH₂)₃—N(CH₃)₂ | —NH—(CH₂)₃—N(CH₃)₂ | H | H | — | — |
| 35 | O-O | —CH₂—C(O)—NH—CH(C(O)—NH—(CH₂)₃—NH—(CH₂)₃—NH₂)—(CH₂)₂—NH—C(O)—CH₂— | —NH—(CH₂)₃—N(CH₃)₂ | —NH—(CH₂)₃—N(CH₃)₂ | H | H | — | — |
| 36 | O-O | —CH₂—C(O)—NH—CH(C(O)—NH—(CH₂)₃—NH₂)—(CH₂)₂—NH—C(O)—CH₂— | —NH—(CH₂)₃—N(CH₃)₂ | —NH—(CH₂)₃—N(CH₃)₂ | H | H | — | — |

Preparation of other [O—O] Compounds of Formula I

Following the procedures of Example 11–13, other [O—O] compounds of Formula I are prepared, including those where the ligand is optionally substituted vancomycin, optionally substituted N-desmethylvancomycin, or optionally substituted chloroeremomycin.

EXAMPLE 14

Preparation of a [R—R] Compound of Formula I via Scheme 13

Preparation of a Compound of Formula I

To 50% aqueous acetonitrile (4.0 mL) was added sequentially 37% formalin (15 uL, 0.20 mmol), 1,4-diaminobutane (8.8 mg, 0.10 mmol), N,N-diisopropylethylamine (174 uL, 1.0 mmol) and vancomycin hydrochloride (300 mg, 0.20 mmol). After stirring 18 h, the product was precipitated by the addition of acetonitrile (45 mL). The solid was isolated by centrifugation, dried in vacuo, and purified by reverse-phase HPLC (5–20% B over 45 min at a flow rate of 50 mL.min). Fractions containing the desired product were identified by mass spectrometry, pooled, and lyophilized to give [R—R]-1,4-bis-(methylamino)butane-bis-(vancomycin), a white powder. MS calculated (M+, 3010.7; found, 3009.2).

mixture of DMF (2.0 mL) and piperidine (1.0 mL). After 45 minutes, the product was isolated by the addition of acetonitrile (45 mL) followed by centrifugation. The resulting solid was washed with ether (45 mL) followed by centrifugation. The crude product was dried in vacuo and purified by reverse phase preprative HPLC (5–15% acetonitrile in water containing 0.1% trifluoroacetic acid over 30 min). The appropriate fractions were combined and lyophylized to give [V]-2-(aminoethyl)vancomycin (a compound of formula (60)) (200 mg) as its trifluoroacetate salt. MS calculated (MH+) 1493.3; found 1493.6.

Preparation of a Compound of Formula (62)

A 0.010 M solution of PyBOP and HOBt in DMF (9.05 mL, 0.0905 mmol each) was added to [V]-2-[Fmoc-aminoethyl]vancomycin (a compound of formula 25') (176 mg, 0.0905 mmol) followed by diisopropylethylamine (12.8 mg, 0.10 mmol). After stirring for 15 minutes, another portion of diisopropylethylamine (12.8 mg, 0.10 mmol) was added. After a further 5 minutes, the compound of formula (60) obtained above (166 mg, 0.0905 mmol) and diisopropylethylamine (35 mg 0.27 mmol) in DMF (1.5 mL) were added. The reaction mixture was stirred for 30 minutes, at which time the product of formula (61) was isolated by the addition of acetonitrile (905 mL) followed by centrifugation. The resulting solid was dried in vacuo and then dissolved in DMF (4 mL) and piperidine (1.0 mL). After 10 minutes, the product was isolated by the addition of acetonitrile (90 mL)

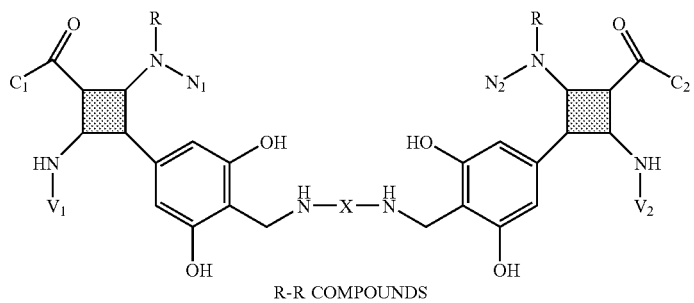

R-R COMPOUNDS

| No. | Class | Linker | C1 | C2 | V1 | V2 | N1 | N2 |
|---|---|---|---|---|---|---|---|---|
| 1 | R-R | —CH$_2$—NH—(CH$_2$)$_4$—NH—CH$_2$— | OH | OH | H | H | H | H |
| 2 | R-R | —CH$_2$—NH—(CH$_2$)$_6$—NH—CH$_2$— | OH | OH | H | H | H | H |
| 3 | R-R | CH$_2$—NH—(CH$_2$)$_2$—NH—C(O)—(CH$_2$)$_3$—C(O)—NH—(CH$_2$)$_2$—NH—CH$_2$— | —NH—(CH$_2$)$_3$—N(CH$_3$)$_2$ | —NH—(CH$_2$)$_3$—N(CH$_3$)$_2$ | H | H | H | H |
| 4 | R-R | —CH$_2$—NH—(CH$_2$)$_{10}$—NH—CH$_2$— | OH | OH | H | H | H | H |

Preparation of other [R—R] Compounds of Formula I

Following the procedures of Example 14, other [R—R] compounds of Formula I are prepared, including those where the ligand is optionally substituted vancomycin, optionally substituted N-desmethylvancomycin, or optionally substituted chloroeremomycin.

EXAMPLE 15

Preparation of a [C—V] Compound of Formula I

Preparation of a Compound of Formula (60)

[V]-2-[Fmoc-aminoethyl]vancomycin (a compound of formula 25) (263 mg, 0.135 mmol) was dissolved in a followed by centrifugation. The resulting solid was washed with ether (90 mL) followed by centrifugation. The solid was dried in vacuo and purified by reverse phase preprative HPLC (5–15% acetonitrile in water containing 0.1% trifluoroacetic acid over 20 min). The appropriate fractions were combined and lyophylized to give namely ([V]-aminoethyl-vancomycin) [C—V]-N-(2-aminoethyl)-(vancomycin)-the product of formula 62 (173 mg) as its trifluoroacetate salt. MS calculated (M+) 2966.6 found 2966.4.

Preparation of a Compound of Formula I [C—V]

The compound of formula (62) obtained above (300 mg, 0.085 mmol) was dissolved in DMF (3.0 mL) and then decanal was added (13.3 mg, 0.085 mmol). After stirring for 30 minutes, methanol (3.0 mL) was added followed by 1.0 M sodium cyanoborohydride in methanol (0.085 mL, 0.085 mmol). After 1 hour, the product was precipitated by the addition of ether (45 mL) followed by centrifugation. The resulting solid was dried in vacuo and purified by reverse phase preprative HPLC (15–35% acetonitrile in water containing 0.1% trifluoroacetic acid over 35 min). The appropriate fractions were combined and lyophylized to give ([V]-n-decylaminoethyl-vancomycin) [C—V]-N-(2-aminoethyl)-(vancomycin), a compound of formula I (126 mg) as its trifluoroacetate salt. MS calculated (M+) 3106.9; found 3106.8.

EXAMPLE 16

Preparation of a [C—V] Compound of Formula I

Preparation of a Compound of Formula (65)

To a stirred solution of [C]-(3-(dimethylamino)propylamine)-[V]-2-[Fmoc-aminoethyl]vancomycin (500 mg, 0.26 mmol, 1.0 equivalent) and succinic acid mono-(2-aminoethylamide (109 mg, 0.29 mmol, 1.1 eq) in 6 ml DMF was added PyBOP (151 mg, 0.29 mmol), HOBT (35 mg, 0.26 mmol), and finally diisopropylethylamine (120 microliters, 0.65 mmol, 2.5 eq). This was allowed to stir at room temperature for twenty minutes, at which time the electrospray mass spectrogram of the crude reaction mixture indicated complete conversion to product (M+=1940). This reaction was poured into 60 ml of acetonitrile; the resulting precipitate was collected by centrifugation, redissolved in 6 ml DMF, and treated with 1 ml piperidine. This reaction was stirred for 20 minutes then checked by HPLC and MS which showed complete conversion to the desired product (M+=1718) 6. The reaction mixture was poured into 60 ml acetonitrile and the resulting precipitate was collected by centrifugation. The product was purified by reversed phase HPLC to provide pure material as the TFA salt.

Preparation of a Compound of Formula I [C—V]

To a stirred solution of 100 mg of the compound obtained as above (0.058 mmol) in 1.0 ml DMSO was added 104 mg (0.070 mmol) of vancomycin. The resulting suspension was stirred until a clear solution was obtained. To this solution was then added 1.0 ml DMF, 37 mg (0.070 mmol) PyBOP, 8 mg (0.058 mmol) HOBT, and diisopropylethylamine (27 microliters, 0.145 mmol). The reaction was stirred for one hour, then added to 15 ml acetonitrile. The resulting precipitate was collected by centrifugation, then purified by reversed phase HPLC to afford (vancomycin)-[C—V]-butane-1,4-dioic acid-(2-aminoethyl)-amide-(2-ethyl)-amide-([C]-3-(dimethylamino)propylamino-vancomycin), (M+=3150).

EXAMPLE 17

Preparation of Formula I (C—V)

The compound of formula (68) (61 mg, 30 µmol), PyBOP (16 mg, 31 µmol) and HOBt (5 mg, 31 µmol) were dissolved in 1 mL of DMF. To the solution were added compound (66) (60 mg, 28 µmol) in 1 mL of DMF and Hunig's base (15 mL, 86 µmol). The reaction was stirred at room temperature for 1 hour. Piperidine (0.5 mL) was added to the solution and the reaction was continued for additional 15 min. The reaction solution was added to 45 mL of ether, giving a precipitate which was collected by centrifugation. The precipitate was dried under vacuum and purified by reverse phase HPLC (80 min 5–45% acetonitrile in water containing 0.1% trifluoroacetic acid, compound eluted at 50 min), yielding ([V]-decylaminoethylvancomycin)-[C—V]-butane-1,4-dioic acid-(2-aminoethyl)-amide-(2-ethyl)-amide-([C]-N-glucosamino-vancomycin), a compound of formula 1 (61 mg, 55%) as its trifluoroacetate salt. MS calculated, MH+3409; Found, 3409.

(In this case, $R^1$=glucosamine, $R^2$=decyl)

EXAMPLE 18

Preparation of a [C—V] Compound of Formula I in which Position [C] is Substituted (1) Preparation of a Compound of Formula (72)

To a solution of [C]-2-aminoethyl vancomycin (22) (40.0 mg, 26.8 µmol) in DMF (2.0 mL) was added a compound of the formula:

$HO_2C$—$CH_2CH_2NHOCCH_2CH_2NHOCCH_2CH_2CH_2$ $CONHCH_2CH_2CONHCH_2CH_2CO_2Fm$ (15) (Fm refers to Fluorenylmethyl) (20.0 mg, 26.8 µmol), followed by PyBOP (20.9 mg, 40.2 µmol), HOBt (5.40 mg, 40.2 µmol), and Hunig's base (23.3 µL, 134 µmol). The reaction solution was stirred for 1 hour and then added dropwise to 20 mL of acetonitrile giving a precipitate, which was collected by centrifugation. The crude precipitate was dried in air, yielding a compound having a MS calculated: MH+, 2068; Found, 2068. The compound (71) was used in the next step without further purification by dissolving in 1 mL of DMF, and 100 µL of piperidine added to the solution. The solution was allowed to stand at room temperature for 30 minutes, following the course of the reaction by mass spectroscopy. The reaction solution was added dropwise to 20 mL of acetonitrile, giving a precipitate that was collected by centrifugation. The precipitate was purified by reverse-phase HPLC on a Ranin C18 Dynamax column (2.5 cm×25 cm, 8☐m particle size), at 10 mL/min flow rate using 0.045% TFA in water as buffer A and 0.045% TFA in acetonitrile as buffer B (HPLC gradient of 2–50% B over 90 minutes). The desired product was identified by mass spectroscopy using an API 300 electrospray mass spectrometer and afterwards lyophilized to a white powder to afford compound (72) as a white powder. MS calculated: MH+, 1890; Found, 1890.

(3) Preparation of a Compound of Formula I

The compound of formula (72) prepared above (10.0 mg, 4.80 µmol) was dissolved in 500 µL of DMF. [C]-(3-dimethylaminopropylamino)-[V]-2-(aminoethyl) vancomycin, a compound of formula (32) (7.20 mg, 4.80 µmol) was added to the solution, followed by PyBOP (2.50 mg, 4.8 umol), HOBt (0.65 mg, 4.80 µmol) and Hunig's base (6.70 µl, 38.4 µmol). The reaction solution was added dropwise to 20 mL of acetonitrile, giving a precipitate that was collected by centrifugation. The precipitate was purified by reverse-phase HPLC on a Ranin C18 Dynamax column (2.5 cm×25 cm, 8 µm particle size), at 10 mL/min flow rate using 0.045% TFA in water as buffer A and 0.045% TFA in acetonitrile as buffer B (HPLC gradient of 2–50% B over 90 minutes). The desired product was identified by mass spectroscopy using an API 300 electrospray mass spectrometer. The compound of Formula I was obtained as a white powder. MS calculated: MH+, 3448; Found, 3448.

EXAMPLE 19

Preparation of a [C—V] Compound of Formula I (1) Preparation of a Compound of Formula (76)

Vancomycin hydrochloride (5.0 g, 3.2 mmol) was suspended in 40 mL of 1,3-dimethyl-3,4,5,6-tetrahydro-2-(1H)-pyrimidinone and heated to 70° C. for 15 minutes. 4-Butoxybenzaldehyde (9)(570 mg, 3.2 mmol) was added and the mixture heated at 70° C. for 1 hour. Sodium cyanoborohydride (241 mg, 3.8 mmol) in 2 mL methanol was added and the mixture was heated at 70° C. for 2 hours, then cooled to room temperature. The reaction solution was added dropwise to 20 mL of acetonitrile, giving a precipitate that was collected by centrifugation. The precipitate was purified by reverse-phase HPLC on a Ranin C18 Dynamax column (2.5 cm×25 cm, 8 μm particle size), at 10 mL/min flow rate using 0.045% TFA in water as buffer A and 0.045% TFA in acetonitrile as buffer B (HPLC gradient of 10–70% B over 90 minutes), yielding a compound of formula (76) as its trifluoroacetate salt. MS calculated: $MH^+$, 1610; Found, 1610.

2. Preparation of a compound of Formula (77)

The compound of formula (76) prepared above (82 mg, 45.0 μmol) was dissolved in 2 mL of DMF. Ethylene diamine (2) (13.4 mg, 22.3 μmol) was added followed by PyBOP (28.0 mg, 54.0 μmol), HOBt (7.2 mg, 54.0 μmol) and Hunig's base (63.0 μL, 360 μmol). The reaction solution was added dropwise to 20 mL of acetonitrile, giving a precipitate that was collected by centrifugation. The precipitate was purified by reverse-phase HPLC on a Ranin C18 Dynamax column (2.5 cm×25 cm, 8 μm particle size), at 10 mL/min flow rate using 0.045% TFA in water as buffer A and 0.045% TFA in acetonitrile as buffer B (HPLC gradient of 2–50% B over 90 minutes), yielding a compound of formula (77) as its trifluroacetate salt. MS calculated: $MH^+$, 1654; Found, 1654.

3. Preparation of a C—V Compound of Formula I in which one V position is substituted The compound of formula (77) prepared above (9.7 mg, 4.9 μmol) was dissolved in 500 μL of DMF. The compound of formula (36) (10.0 mg, 4.9 μmol) was added to the solution, followed by PyBOP (3.06 mg, 5.9 μmol), HOBt (0.80 mg, 5.9 μmol) and Hunig's base (6.7 μL, 38.4 μmol). The reaction solution was added dropwise to 20 mL of acetonitrile, giving a precipitate that was collected by centrifugation. The precipitate was purified by reverse-phase HPLC on a Ranin C18 Dynamax column (2.5 cm×25 cm, 8 μm particle size), at 10 mL/min flow rate using 0.045% TFA in water as buffer A and 0.045% TFA in acetonitrile as buffer B (HPLC gradient of 2–50% B over 90 minutes), yielding a compound of Formula I as its trifluroacetate salt. MS calculated: $MH^+$, 3312; Found, 3312.

EXAMPLE 20

Preparation of a [C—V] Compound of Formula I

To a solution of [C]-3-(dimethylaminopropylamido)-[V]-(2-aminoethyl)vancomycin tetra-TFA salt (32) (30 mg, 0.015 mmol) and [C]-(2-aminoethylamido)vancomycin di-TFA salt (27 mg, 0.015 mmol) in DMF (0.20 mL) was added a solution of dimethyl suberimidate dihydrochloride (4.1 mg, 0.015 mmol) and diisopropylethylamine (3.9 mg, volume, 0.030 mmol) in DMF (0.41 mL). After one hour, the reaction was judged complete by mass spectrometry. The solution was added to acetonitrile (14 mL), and the resultant precipitate isolated by centrifugation, resuspended in ether (14 mL) and isolated again by centrifugation. After drying in vacuo, the precipate was purified by reverse-phase HPLC on a Ranin C18 Dynamax column (2.5 cm×25 cm, 8 μ particle size) at 16 mL/min flow rate using 0.045% TFA in water as buffer A and 0.045% TFA in acetonitrile as buffer B (HPLC gradient of 5–20% B over 60 minutes). Fractions were analyzed by mass spectrometry and analytical HPLC, and those containing the title product were combined and lyophylized to give a [C—V] linked compound of Formula I as a white powder (9 mg, 15%). $M^+$ calculated: 3204.01 found: 3203.6.

(4) Preparation of other Compounds of Formula I

Accordingly, following the procedures of Examples 15–20 other [C—V] compounds of Formula I were prepared (see Table below).

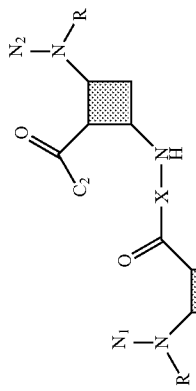

C-V COMPOUNDS

| No. | Class | Linker | N1 | N2 | V1 | C2 | R1 | R2 |
|---|---|---|---|---|---|---|---|---|
| 1 | C-V | —NH—$(CH_2)_2$—NH—C(O)—$(CH_2)_3$—C(O)—NH—$(CH_2)_2$— | H | H | H | —NH—$(CH_2)_3$—$N(CH_3)_2$ | | |
| 2 | C-V | —$(CH_2)_2$—C(O)—NH—$(CH_2)_2$—NH—C(O)—$(CH_2)_3$—NH—C(O)—NH—$(CH_2)_2$— | H | H | H | —NH—$(CH_2)_3$—$N(CH_3)_2$ | | |
| 3 | C-V | —NH—$(CH_2)_2$—NH—C(O)—$(CH_2)_3$—C(O)—NH—$(CH_2)_2$— | H | H | —$(CH_2)_9$—$CH_3$ | —NH—$(CH_2)_3$—$N(CH_3)_2$ | | |
| 4 | C-V | —NH—$(CH_2)_2$—NH—C(O)—$(CH_2)_3$—C(O)—NH—$(CH_2)_2$— | H | H | —$(CH_2)_9$—$CH_3$ | —NH—$(CH_2)_3$—$N(CH_3)_2$ | | |
| 5 | C-V | —NH—$(CH_2)_2$—NH—C(O)—$(CH_2)_3$—C(O)—NH—$(CH_2)_2$— | H | H | —$CH_2$—Z—O—$(CH_2)_3$—$CH_3$ Where Z = 1,4-phenyl | —NH—$(CH_2)_3$—$N(CH_3)_2$ | | |
| 6 | C-V | —NH—$(CH_2)_2$—NH—C(O)—$CH_2$—O—$CH_2$—C(O)—NH—$(CH_2)_2$— | H | H | —$CH_2$—Z Where Z = biphenyl | —NH—$(CH_2)_3$—$N(CH_3)_2$ | | |
| 7 | C-V | —NH—$(CH_2)_2$—NH—C(O)—$CH_2$—O—$CH_2$—C(O)—NH—$(CH_2)_2$—NH— | H | H | H | —NH—$(CH_2)_8$—$CH_3$ | | |
| 8 | C-V | —NH—$(CH_2)_2$—NH—C(O)—$CH_2$—O—$CH_2$—C(O)—NH—$(CH_2)_2$—NH— | H | H | H | —NH—$(CH_2)_{11}$—$CH_3$ | | |
| 9 | C-V | —NH—$(CH_2)_2$—NH—C(O)—$CH_2$—O—$CH_2$—C(O)—NH—$(CH_2)_2$—NH— | H | H | —$CH_2$—Z—O—$(CH_2)_3$—$CH_3$ Where Z = 1,4-phenyl | —NH—$(CH_2)_3$—$N(CH_3)_2$ | | |
| 10 | C-V | —NH—$(CH_2)_2$—C(O)—NH—$(CH_2)_2$—NH— | H | H | —$CH_2$—Z Where Z = biphenyl | —NH—$(CH_2)_3$—$N(CH_3)_2$ | | |
| 11 | C-V | —NH—$(CH_2)_2$— | H | H | —$(CH_2)_2$—NH—C(O)—$(CH_2)_8$—$CH_3$ | OH | | |
| 12 | C-V | —NH—$(CH_2)_2$—C(O)—NH—$(CH_2)_2$— | H | H | —$CH_2$—Z Where Z = 4-(4'-chloro)biphenyl | —NH—$(CH_2)_3$—$N(CH_3)_2$ | | |
| 13 | C-V | —NH—$(CH_2)_2$—C(O)—NH—$(CH_2)_2$— | H | H | —$CH_2$—Z—O—Ph Where Z = 1,4 phenyl | —NH—$(CH_2)_3$—$N(CH_3)_2$ | | |
| 14 | C-V | —NH—$(CH_2)_2$—C(O)—NH—$(CH_2)_2$— | H | H | —$CH_2$—Z Where Z = 2,4-dichlorophenyl | —NH—$(CH_2)_3$—$N(CH_3)_2$ | | |
| 15 | C-V | —NH—$(CH_2)_2$—C(O)—NH—$(CH_2)_2$— | H | H | —$CH_2$—Z—Z' Where Z = 1,2-phenyl, Z' = glucoside | —NH—$(CH_2)_3$—$N(CH_3)_2$ | | |

C-V COMPOUNDS

| No. | Class | Linker | N1 | N2 | V1 | C2 | R1 |
|---|---|---|---|---|---|---|---|
| 16 | C-V | —NH—(CH$_2$)$_2$—NH—C(O)—(CH$_2$)$_2$—C(O)—NH—(CH$_2$)$_2$— | —CH$_2$—Z—Z' Where Z = 1,2-phenyl, Z' = glucoside | H | H | —NH—(CH$_2$)$_3$—N(CH$_3$)$_2$ | |
| 17 | C-V | —NH—(CH$_2$)$_2$—NH—C(O)—(CH$_2$)$_2$—C(O)—NH—(CH$_2$)$_2$— | H | H | —CH$_2$—Z—CF$_3$ Where Z = 4,4'-biphenyl | —NH—(CH$_2$)$_3$—N(CH$_3$)$_2$ | |
| 18 | C-V | —NH—(CH$_2$)$_2$—NH—C(O)—(CH$_2$)$_2$—C(O)—NH—(CH$_2$)$_2$— | H | H | —CH$_2$—Z—CH(CH$_3$)$_2$ Where Z = 1,4 = phenyl | —NH—(CH$_2$)$_3$—N(CH$_3$)$_2$ | |
| 19 | C-V | —NH—CH$_2$—Z—CH$_2$ Where Z = 1,4-phenyl | H | H | H | —NH—(CH$_2$)$_3$—N(CH$_3$)$_2$ | |
| 20 | C-V | —NH—CH$_2$—Z—CH$_2$ Where Z = 1,4-phenyl | H | H | —CH$_2$—Z— Where Z = biphenyl | —NH—(CH$_2$)$_3$—N(CH$_3$)$_2$ | |
| 21 | C-V | —NH—(CH$_2$)$_2$— | H | H | —(CH$_2$)$_b$—CH$_3$ | OH | |
| 22 | C-V | —NH—(CH$_2$)$_2$— | H | H | —CH$_2$—Z— Where Z = 2,4-dichlorophenyl | —NH—(CH$_2$)$_3$—N(CH$_3$)$_2$ | |
| 23 | C-V | —NH—(CH$_2$)$_2$— | H | H | —CH$_2$—Z—O—(CH$_2$)$_3$—CH$_3$ Where Z = 1,4-phenyl | —NH—(CH$_2$)$_3$—N(CH$_3$)$_2$ | |
| 24 | C-V | —NH—(CH$_2$)$_2$— | H | H | —CH$_2$—Z—CF$_3$ Where Z = 4,4'-biphenyl | —NH—(CH$_2$)$_3$—N(CH$_3$)$_2$ | |
| 25 | C-V | —NH—(CH$_2$)$_2$— | H | H | —CH$_2$—Z— Where Z = biphenyl | —NH—(CH$_2$)$_3$—N(CH$_3$)$_2$ | |
| 26 | C-V | —NH—(CH$_2$)$_2$— | H | H | —CH$_2$—Z— Where Z = 4-(4'-chloro) biphenyl | —NH—(CH$_2$)$_3$—N(CH$_3$)$_2$ | |
| 27 | C-V | —NH—(CH$_2$)$_2$— | H | H | H | —NH—(CH$_2$)$_3$—N(CH$_3$)$_2$ | |
| 28 | C-V | —NH—(CH$_2$)$_2$— | H | H | —(CH$_2$)$_2$—NH$_2$ | —NH—(CH$_2$)$_3$—N(CH$_3$)$_2$ | |
| 29 | C-V | —NH—(CH$_2$)$_2$— | H | H | —(CH$_2$)$_2$—NH—C(O)—(CH$_2$)$_8$—CH$_3$ | —NH—(CH$_2$)$_3$—N(CH$_3$)$_2$ | |
| 30 | C-V | —NH—(CH$_2$)$_2$— | H | H | —(CH$_2$)$_2$—NH$_2$ | OH | |
| 31 | C-V | —NH—(CH$_2$)$_2$— | H | H | —(CH$_2$)$_2$—NH—C(O)—Z Where Z = biphenyl | OH | |

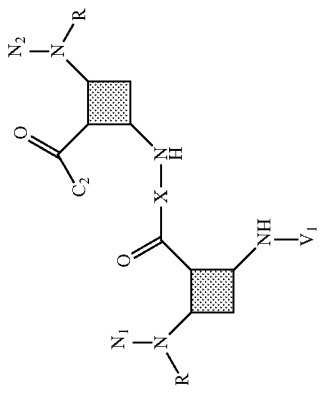

C-V COMPOUNDS

| No. | Class | Linker | N1 | N2 | V1 | C2 | R1 | R2 |
|---|---|---|---|---|---|---|---|---|
| 32 | C-V | —NH—$(CH_2)_2$— | H | H | —$(CH_2)_2$—NH—C(O)—Z Where Z = biphenyl | —NH—$(CH_2)_3$—N$(CH_3)_2$ | |
| 33 | C-V | —NH—$(CH_2)_2$— | H | H | —$(CH_2)_2$—NH—$(CH_2)_9$—$CH_3$ | OH | |
| 34 | C-V | —NH—$(CH_2)_2$— | H | H | —$(CH_2)_2$—NH—$(CH_2)_9$—$CH_3$ | OH | |
| 35 | C-V | —NH—$(CH_2)_2$—NH—C(O)—$(CH_2)_2$—C(O)—NH—$(CH_2)_2$— | H | H | —$CH_2$—Z Where Z = biphenyl | OH | |
| 36 | C-V | —NH—$(CH_2)_2$— | H | H | —$(CH_2)_{12}$—C(O)— | OH | |
| 37 | C-V | —NH—$(CH_2)_2$— | H | H | —$(CH_2)_4$—$CH_3$ | —NH—$(CH_2)_3$—N$(CH_3)_2$ | |
| 38 | C-V | —NH—$(CH_2)_2$— | H | H | —$(CH_2)_2$—NH—C(O)—$CH_3$ | OH | |
| 39 | C-V | —NH—$(CH_2)_2$— | H | H | —$(CH_2)_4$—$CH_3$ | —NH—$(CH_2)_3$—N$(CH_3)_2$ | |
| 40 | C-V | —NH—$(CH_2)_2$—C(O)—NH—$(CH_2)_2$— | H | H | —$(CH_2)_4$—$CH_3$ | —NH—$(CH_2)_3$—N$(CH_3)_2$ | |
| 41 | C-V | —NH—CH(CH$(CH_3)_2$)—C(O)—NH—$(CH_2)_2$— | H | H | —$(CH_2)_2$—$NH_2$ | —NH—$(CH_2)_3$—N$(CH_3)_2$ | |
| 42 | C-V | —NH—CH(CH$_2$—Ph)—C(O)—NH—$(CH_2)_2$— | H | H | | —NH—$(CH_2)_3$—N$(CH_3)_2$ | |
| 43 | C-V | —NH—$(CH_2)_2$—NH—C(O)—$(CH_2)_2$—C(O)—NH—$(CH_2)_2$— | H | H | | —NH—$(CH_2)_3$—N$(CH_3)_2$ | |
| 44 | C-V | —NH—CH(CH$(CH_3)_2$)—C(O)—NH—$(CH_2)_2$— | H | H | | —NH—$(CH_2)_3$—N$(CH_3)_2$ | |
| 45 | C-V | —NH—$(CH_2)_2$— | —$CH_2$—Z—Z' Where Z = glucoside, Z' = 1,2-phenyl, | H | | —NH—$(CH_2)_3$—N$(CH_3)_2$ | |
| 46 | C-V | —NH—CH(CH$_2$—Ph)—C(O)—NH—$(CH_2)_2$— | —$CH_2$—Z—Z' Where Z = glucoside, Z' = 1,2-phenyl, | H | | —NH—$(CH_2)_3$—N$(CH_3)_2$ | |
| 47 | C-V | —NH—$(CH_2)_3$—C(O)—NH—$(CH_2)_2$— | H | H | | —NH—$(CH_2)_3$—N$(CH_3)_2$ | |
| 48 | C-V | —NH—$(CH_2)_4$—C(O)—NH—$(CH_2)_2$— | H | H | | —NH—$(CH_2)_3$—N$(CH_3)_2$ | |
| 49 | C-V | —NH—$(CH_2)_2$—NH—C(O)—$(CH_2)_2$—C(O)—NH—$(CH_2)_2$— | H | H | —$(CH_2)_8$—$CH_3$ | —NH—$(CH_2)_3$—N$(CH_3)_2$ | |
| 50 | C-V | —NH—$(CH_2)_2$—NH—C(O)—$(CH_2)_2$—C(O)—NH—$(CH_2)_2$— | H | H | —$(CH_2)_2$—NH—C(O)—Z Where Z = biphenyl | —NH—$(CH_2)_3$—N$(CH_3)_2$ | |

C-V COMPOUNDS

| No. | Class | Linker | N1 | N2 | V1 | C2 | R1 | R2 |
|---|---|---|---|---|---|---|---|---|
| 51 | C-V | —NH—(CH$_2$)$_2$—NH—C(O)—(CH$_2$)$_2$—C(O)—NH—(CH$_2$)$_2$— | H | H | —(CH$_2$)$_2$—NH—C(O)—(CH$_2$)$_8$—CH$_3$ | OH | | |
| 52 | C-V | —NH—(CH$_2$)$_2$—NH—C(O)—(CH$_2$)$_2$—C(O)—NH—(CH$_2$)$_2$— | H | H | —(CH$_2$)$_2$—NH—(CH$_2$)$_9$—CH$_3$ | —NH—(CH$_2$)$_3$—N(CH$_3$)$_2$ | | |
| 53 | C-V | —NH—(CH$_2$)$_2$—NH—C(O)—(CH$_2$)$_2$—C(O)—NH—(CH$_2$)$_2$— | H | H | —(CH$_2$)$_2$—NH—CH$_2$—Z Where Z = biphenyl | —NH—(CH$_2$)$_3$—N(CH$_3$)$_2$ | | |
| 54 | C-V | —NH—(CH$_2$)$_2$— | H | H | H | —NH—(CH$_2$)$_8$—CH$_3$ | | |
| 55 | C-V | —NH—(CH$_2$)$_2$— | H | H | H | —NH—(CH$_2$)$_{11}$—CH$_3$ | | |
| 56 | C-V | —NH—(CH$_2$)$_2$— | H | H | H | —(CH$_2$)$_3$—NH—C(O)—Z Where Z = biphenyl | | |
| 57 | C-V | —NH—(CH$_2$)$_2$— | H | H | —(CH$_2$)$_2$—NH$_2$ | —NH—(CH$_2$)$_2$—O—CH$_3$ | | |
| 58 | C-V | —NH—(CH$_2$)$_2$— | H | H | —(CH$_2$)$_2$—NH—(CH$_2$)$_9$—CH$_3$ | —NH—(CH$_2$)$_2$—O—CH$_3$ | | |
| 59 | C-V | —NH—(CH$_2$)$_2$— | H | H | H | —NH—(CH$_2$)$_3$—CH$_3$ | | |
| 60 | C-V | —NH—(CH$_2$)$_2$— | H | H | H | OH | | |
| 61 | C-V | —NH—(CH$_2$)$_2$— | H | H | H | —NH—(CH$_2$)$_2$—NH$_2$ | | |
| 62 | C-V | —NH—(CH$_2$)$_2$— | H | H | H | C(O)—(CH$_2$)$_8$—CH$_3$ | | |
| 63 | C-V | —NH—(CH$_2$)$_2$— | H | H | H | OH | | |
| 64 | C-V | —NH—(CH$_2$)$_3$— | H | H | —(CH$_2$)$_2$—N((CH$_2$)$_9$—CH$_3$)$_2$ | —NH—(CH$_2$)$_3$—N(CH$_3$)$_2$ | | |
| 65 | C-V | —NH—(CH$_2$)$_6$— | H | H | H | —NH—(CH$_2$)$_3$—N(CH$_3$)$_2$ | | |
| 66 | C-V | —NH—(CH$_2$)$_6$— | H | H | —(CH$_2$)$_2$—NH—(CH$_2$)$_9$—CH$_3$ | —NH—(CH$_2$)$_3$—N(CH$_3$)$_2$ | | |
| 67 | C-V | —NH—(CH$_2$)$_2$— | H | H | —(CH$_2$)$_2$—NH$_2$ | —NH—(CH$_2$)$_3$—N(CH$_3$)$_2$ | | |
| 68 | C-V | —NH—(CH$_2$)$_2$— | H | H | —(CH$_2$)$_2$—NH—(CH$_2$)$_9$—CH$_3$ | —NH—(CH$_2$)$_3$—N(CH$_3$)$_2$ | | |
| 69 | C-V | —NH—(CH$_2$)$_2$— | H | H | —(CH$_2$)$_2$—NH$_2$ | —NH—(CH$_2$)$_3$—N(CH$_3$)$_2$ | | |
| 70 | C-V | —NH—(CH$_2$)$_3$— | H | H | —(CH$_2$)$_3$—NH$_2$ | —NH—(CH$_2$)$_3$—N(CH$_3$)$_2$ | | |
| 71 | C-V | —NH—(CH$_2$)$_2$— | H | H | —(CH$_2$)$_6$—NH$_2$ | —NH—(CH$_2$)$_3$—N(CH$_3$)$_2$ | | |
| 72 | C-V | —NH—(CH$_2$)$_2$— | H | H | —(CH$_2$)$_6$—NH$_2$ | —NH—(CH$_2$)$_3$—N(CH$_3$)$_2$ | | |
| 73 | C-V | —NH—(CH$_2$)$_2$— | H | H | —(CH$_2$)$_2$—NH—(CH$_2$)$_5$—CH$_3$ | —NH—(CH$_2$)$_3$—N(CH$_3$)$_2$ | | |
| 74 | C-V | —NH—(CH$_2$)$_2$— | H | H | —(CH$_2$)$_2$—NH—(CH$_2$)$_7$—CH$_3$ | —NH—(CH$_2$)$_2$—NH—CH$_3$ (CH$_2$)$_9$—CH$_3$ | | |
| 75 | C-V | —NH—(CH$_2$)$_2$— | H | H | —(CH$_2$)$_2$—NH—(CH$_2$)$_5$—CH$_3$ | —NH—(CH$_2$)$_3$—N(CH$_3$)$_2$ | | |
| 76 | C-V | —NH—(CH$_2$)$_2$— | H | H | —(CH$_2$)$_2$—NH—(CH$_2$)$_7$—CH$_3$ | —NH—(CH$_2$)$_3$—N(CH$_3$)$_2$ | | |
| 77 | C-V | —NH—(CH$_2$)$_2$— | H | H | —(CH$_2$)$_2$—NH—CH$_2$—Z Where Z = biphenyl | —NH—(CH$_2$)$_3$—N(CH$_3$)$_2$ | | |

C-V COMPOUNDS

| No. | Class | Linker | N1 | N2 | V1 | C2 | R1 | R2 |
|---|---|---|---|---|---|---|---|---|
| 78 | C-V | —NH—(CH$_2$)$_2$— | H | H | —(CH$_2$)$_2$—N((CH$_2$)$_5$—CH$_3$)$_2$ | —NH—(CH$_2$)$_3$—N(CH$_3$)$_2$ | | |
| 79 | C-V | —NH—(CH$_2$)$_2$— | H | H | —(CH$_2$)$_2$—NH—(CH$_2$)$_2$—NH$_2$ | —NH—(CH$_2$)$_3$—N(CH$_3$)$_2$ | | |
| 80 | C-V | —NH—(CH$_2$)$_2$— | H | H | —(CH$_2$)$_2$—NH—C(O)—CH$_2$—N$^+$(CH$_3$)$_2$((CH$_2$)$_5$—CH$_3$) | —NH—(CH$_2$)$_3$—N(CH$_3$)$_2$ | | |
| 81 | C-V | —NH—(CH$_2$)$_2$— | H | H | —(CH$_2$)$_2$—NH—C(O)—CH$_2$—N$^+$(CH$_3$)$_2$((CH$_2$)$_7$—CH$_3$) | —NH—(CH$_2$)$_3$—N(CH$_3$)$_2$ | | |
| 82 | C-V | —NH—(CH$_2$)$_2$— | H | H | —(CH$_2$)$_2$—NH—C(O)—CH$_2$—N$^+$(CH$_3$)$_2$((CH$_2$)$_{10}$—CH$_3$) | —NH—(CH$_2$)$_3$—N(CH$_3$)$_2$ | | |
| 83 | C-V | —NH—(CH$_2$)$_2$— | H | H | —(CH$_2$)$_2$—NH—(CH$_2$)$_3$—CH$_3$ | —NH—(CH$_2$)$_3$—N(CH$_3$)$_2$ | | |
| 84 | C-V | —NH—(CH$_2$)$_2$— | H | H | —(CH$_2$)$_2$—NH—(CH$_2$)$_9$—CH$_3$ | —NH—(CH$_2$)$_3$—N(CH$_3$)$_2$ | | |
| 85 | C-V | —NH—CH(COOH)—CH$_2$—C(O)—NH—(CH$_2$)$_2$— | H | H | H | —NH—(CH$_2$)$_3$—N(CH$_3$)$_2$ | | |
| 86 | C-V | —NH—CH(C(O)—NH—(CH$_2$)$_3$—N(CH$_3$)$_2$)—CH$_2$—C(O)—NH—(CH$_2$)$_2$— | H | H | H | —NH—(CH$_2$)$_3$—N(CH$_3$)$_2$ | | |
| 87 | C-V | —NH—CH(C(O)—NH—(CH$_2$)$_3$—CH$_3$)—CH$_2$—C(O)—NH—(CH$_2$)$_2$— | H | H | H | —NH—(CH$_2$)$_3$—N(CH$_3$)$_2$ | | |
| 88 | C-V | —NH—CH(C(O)—NH—(CH$_2$)$_{11}$—CH$_3$)—CH$_2$—C(O)—NH—(CH$_2$)$_2$— | H | H | H | —NH—(CH$_2$)$_3$—N(CH$_3$)$_2$ | | |
| 89 | C-V | —NH—CH(COOH)—CH$_2$—C(O)—NH—(CH$_2$)$_2$— | H | H | —(CH$_2$)$_2$—NH$_2$ | —NH—(CH$_2$)$_3$—N(CH$_3$)$_2$ | | |
| 90 | C-V | —NH—(CH$_2$)$_2$— | H | H | —CH$_2$—Z—CH$_2$—NH$_2$ Where Z = 1,4-phenyl | —NH—(CH$_2$)$_3$—N(CH$_3$)$_2$ | | |
| 91 | C-V | —NH—CH$_2$—Z—CH$_2$— Where Z = 1,4 phenyl | H | H | —(CH$_2$)$_2$—NH$_2$ | —NH—(CH$_2$)$_3$—N(CH$_3$)$_2$ | | |
| 92 | C-V | —NH—(CH$_2$)$_2$— | H | H | —CH$_2$—Z—CH$_2$—NH—(CH$_2$)$_9$—CH$_3$ Where Z = 1,4-phenyl | —NH—(CH$_2$)$_3$—N(CH$_3$)$_2$ | | |
| 93 | C-V | —NH—(CH$_2$)$_2$— | H | H | —(CH$_2$)$_2$—NH—CH$_2$—Ph | —NH—(CH$_2$)$_3$—N(CH$_3$)$_2$ | | |
| 94 | C-V | —NH—CH(COOH)—CH$_2$—C(O)—NH—(CH$_2$)$_2$— | H | H | —(CH$_2$)$_2$—N((CH$_2$)$_9$—CH$_3$)$_2$ | —NH—(CH$_2$)$_3$—N(CH$_3$)$_2$ | | |
| 95 | C-V | —NH—(CH$_2$)$_2$— | H | H | —(CH$_2$)$_2$—NH—(CH$_2$)$_9$—CH$_3$ | —NH—(CH$_2$)$_3$—N(CH$_3$)$_2$ | | |
| 96 | C-V | —NH—CH(C(O)—N(CH$_3$)$_2$)—CH$_2$—C(O)—NH—(CH$_2$)$_2$— | H | H | —(CH$_2$)$_2$—NH—(CH$_2$)$_9$—CH$_3$ | —NH—(CH$_2$)$_3$—N(CH$_3$)$_2$ | | |
| 97 | C-V | —NH—(CH$_2$)$_2$— | H | H | —(CH$_2$)$_2$—NH—(CH$_2$)$_9$—CH$_3$ | —NH—(CH$_2$)$_3$—N(CH$_3$)$_2$ | | |
| 98 | C-V | —NH—(CH$_2$)$_2$— | H | H | —(CH$_2$)$_2$—NH—(CH$_2$)$_9$—CH$_3$ | —NH—(CH$_2$)$_3$—N(CH$_3$)$_2$ | | |

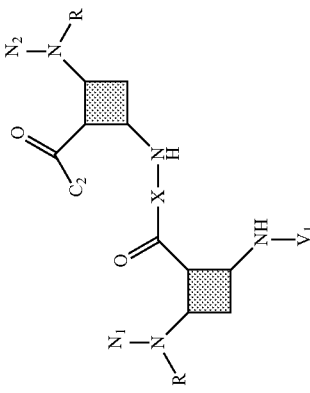

C-V COMPOUNDS

| No. | Class | Linker | N1 | N2 | V1 | C2 | R1 | R2 |
|---|---|---|---|---|---|---|---|---|
| 99 | C-V | —NH—CH(C(O)—NH—(CH₂)₂—Z)—CH₂—C(O)—NH—(CH₂)₂— Where Z = N-morpholino | H | H | —(CH₂)₂—NH—(CH₂)₉—CH₃ | —NH—(CH₂)₃—N⁺(CH₃)₃ | | |
| 100 | C-V | —NH—CH(COOH)—CH₂—C(O)—NH—(CH₂)₂— | H | H | —(CH₂)₂—NH—(CH₂)₉—CH₃ | —NH—(CH₂)₃—N(CH₃)₂ | | |
| 101 | C-V | —NH—(CH₂)₂— | H | H | —(CH₂)₂—NH—CH₂—Z Where Z = 3,4-(15-crown-5)-phenyl | OH | | |
| 102 | C-V | —NH—(CH₂)₂— | H | H | —CH₂—Z Where Z = 3,4-(15-crown-5)-phenyl | —NH—(CH₂)₃—N(CH₃)₂ | | |
| 103 | C-V | —NH—(CH₂)₂—NH—C(O)—(CH₂)₂—C(O)—NH—(CH₂)₂— | H | H | —CH₂—Z Where Z = 3,4-(15-crown-5)-phenyl | —NH—(CH₂)₃—N(CH₃)₂ | | |
| 104 | C-V | —NH—(CH₂)₂— | H | H | —(CH₂)₂—NH—CH₂—Z Where Z = biphenyl | —NH—(CH₂)₃—Z Where Z = N-morpholino | | |
| 105 | C-V | —NH—(CH₂)₂— | H | H | —(CH₂)₂—NH—CH₂—Z Where Z = biphenyl | NH—CH₂—(CH(OH))₄—CH₂OH | | |
| 106 | C-V | —NH—(CH₂)₂— | H | H | —(CH₂)₂—NH—CH₂—Z Where Z = biphenyl | -N-glucosamine | | |
| 107 | C-V | —NH—(CH₂)₂— | H | H | —(CH₂)₂—NH—CH₂—Z Where Z = biphenyl | NH—(CH₂)₂—NH₂ | | |
| 108 | C-V | —NH—(CH₂)₂— | H | H | —(CH₂)₂—NH—CH₂—Z Where Z = biphenyl | NH—(CH₂)₃—NH—(CH₂)₃—NH—(CH₂)₃—NH | | |
| 109 | C-V | —NH—(CH₂)₂— | H | H | —(CH₂)₂—NH—CH₂—Z Where Z = biphenyl | NH—(CH₂)₂—O—CH₃ | | |
| 110 | C-V | —NH—(CH₂)₂— | H | H | —(CH₂)₂—NH—CH₂—Z Where Z = biphenyl | —NH—(CH₂)₂—N⁺(CH₃)₃ | | |
| 111 | C-V | —NH—(CH₂)₂— | H | H | —(CH₂)₂—NH—(CH₂)₉—CH₃ | —NH—(CH₂)₅—CH₃ | | |
| 112 | C-V | —NH—(CH₂)₂— | H | H | —(CH₂)₂—NH—(CH₂)₉—CH₃ | —NH—(CH₂)₃—Z Where Z = N-morpholino | | |
| 113 | C-V | —NH—(CH₂)₂— | H | H | —(CH₂)₂—NH—(CH₂)₉—CH₃ | NH—CH₂—(CH(OH))₄—CH₂OH | | |

-continued

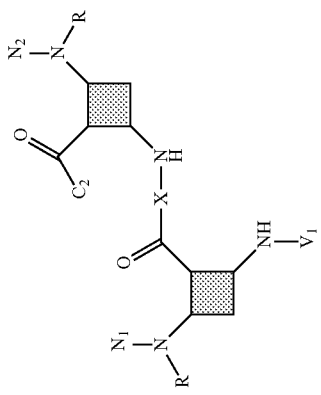

C-V COMPOUNDS

| No. | Class | Linker | N1 | N2 | V1 | C2 | R1 | R2 |
|---|---|---|---|---|---|---|---|---|
| 114 | C-V | —NH—(CH$_2$)$_2$— | H | H | —(CH$_2$)$_2$—NH—(CH$_2$)$_9$—CH$_3$ | -N-glucosamine | | |
| 115 | C-V | —NH—(CH$_2$)$_2$— | H | H | —(CH$_2$)$_2$—NH—(CH$_2$)$_9$—CH$_3$ | —(CH$_2$)$_2$—NH$_2$ | | |
| 116 | C-V | —NH—(CH$_2$)$_2$— | H | H | —(CH$_2$)$_2$—NH—(CH$_2$)$_9$—CH$_3$ | —NH—(CH$_2$)$_3$—NH—(CH$_2$)$_3$—NH$_2$ | | |
| 117 | C-V | —NH—(CH$_2$)$_2$— | H | H | —(CH$_2$)$_2$—NH—(CH$_2$)$_2$—NH—(CH$_2$)$_2$—NH—(CH$_2$)$_2$—CH$_3$ | —NH—(CH$_2$)$_3$—N(CH$_3$)$_2$ | | |
| 118 | C-V | —NH—(CH$_2$)$_2$— | H | H | (trans)-(CH$_2$)$_3$—CH=CH—(CH$_2$)$_4$—CH$_3$ | —NH—(CH$_2$)$_3$—N(CH$_3$)$_2$ | | |
| 119 | C-V | —NH—(CH$_2$)$_2$— | H | H | (cis)-(CH$_2$)$_3$—CH=CH—(CH$_2$)$_4$—CH$_3$ | —NH—(CH$_2$)$_3$—N(CH$_3$)$_2$ | | |
| 120 | C-V | —NH—(CH$_2$)$_2$— | H | H | —CH$_2$—Z—O—Ph  Where Z = 1,4-phenyl | —NH—(CH$_2$)$_3$—N(CH$_3$)$_2$ | | |
| 121 | C-V | —NH—(CH$_2$)$_2$— | H | H | —CH$_2$—Z—O—CH$_2$—Ph  Where Z = 1,4-phenyl | —NH—(CH$_2$)$_3$—N(CH$_3$)$_2$ | | |
| 122 | C-V | —NH—(CH$_2$)$_2$— | H | H | (R)—CH$_2$—CH(CH$_3$)—(CH$_2$)$_3$—CH=CH(CH$_3$)—CH$_2$—Z  Where Z = 5-norbornenyl | —NH—(CH$_2$)$_3$—N(CH$_3$)$_2$ | | |
| 123 | C-V | —NH—(CH$_2$)$_2$— | H | H | | —NH—(CH$_2$)$_3$—N(CH$_3$)$_2$ | | |
| 124 | C-V | —NH—(CH$_2$)$_2$— | H | H | (trans-trans)-(CH$_2$)$_2$—NH—CH$_2$—CH=C(CH$_3$)—(CH$_2$)$_2$—CH=C(CH$_3$)$_2$ | —NH—(CH$_2$)$_3$—N(CH$_3$)$_2$ | | |
| 125 | C-V | —NH—(CH$_2$)$_2$— | H | H | —CH$_2$—CH=C(CH$_3$)—(CH$_2$)$_2$—CH=C(CH$_3$)$_2$ | —NH—(CH$_2$)$_3$—N(CH$_3$)$_2$ | | |
| 126 | C-V | —NH—(CH$_2$)$_2$— | H | H | (CH$_2$)$_2$—CH=C(CH$_3$)—(CH$_2$)$_2$—CH=C(CH$_3$)$_2$  (CH$_2$)$_2$—CH=C(CH$_3$)—(CH$_2$)$_2$—CH=C(CH$_3$)$_2$ | OH | | |

-continued

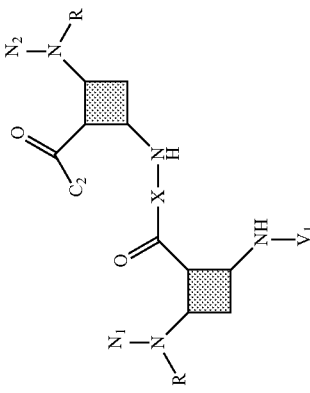

C-V COMPOUNDS

| No. | Class | Linker | N1 | N2 | V1 | C2 | R1 | R2 |
|---|---|---|---|---|---|---|---|---|
| 127 | C-V | —NH—(CH$_2$)$_2$— | H | H | —(CH$_2$)$_2$—NH—CH$_2$—CH=C(CH$_3$)—(CH$_2$)$_2$—CH=C(CH$_3$)$_2$ | OH | | |
| 128 | C-V | —NH—(CH$_2$)$_2$— | H | H | —(CH$_2$)$_2$—NH—(CH$_2$)$_2$—O—CH$_3$ | | | |
| 129 | C-V | —NH—(CH$_2$)$_2$— | H | H | —(CH$_2$)$_2$—O—(CH$_2$)$_2$—N((CH$_2$)$_2$—O—(CH$_2$)$_2$—O—CH$_3$)$_2$ | —NH—(CH$_2$)$_3$—N(CH$_3$)$_2$ | | |
| 130 | C-V | —NH—(CH$_2$)$_2$— | H | H | —(CH$_2$)$_2$—NH—CH$_2$—Z—O—(CH$_2$)$_2$—CH$_3$ Where Z = 1,4-phenyl | —NH—(CH$_2$)$_3$—N(CH$_3$)$_2$ | | |
| 131 | C-V | —NH—(CH$_2$)$_2$— | H | H | —(CH$_2$)$_2$—NH—CH$_2$—Z—O—(CH$_2$)$_3$—CH$_3$ Where Z = 1,4-phenyl | —NH—(CH$_2$)$_3$—N(CH$_3$)$_2$ | | |
| 132 | C-V | —NH—(CH$_2$)$_2$— | H | H | —(CH$_2$)$_2$—NH—CH$_2$—Z—O—(CH$_2$)$_5$—CH$_3$ Where Z = 1,4-phenyl | —NH—(CH$_2$)$_3$—N(CH$_3$)$_2$ | | |
| 133 | C-V | —NH—(CH$_2$)$_2$— | H | H | —(CH$_2$)$_2$—NH—CH$_2$—Z—O—(CH$_2$)$_7$—CH$_3$ Where Z = 1,4-phenyl | —NH—(CH$_2$)$_3$—N(CH$_3$)$_2$ | | |
| 134 | C-V | —NH—(CH$_2$)$_2$— | H | H | —(CH$_2$)$_2$—NH—CH$_2$—Z—O—(CH$_2$)$_{11}$—CH$_3$ Where Z = 1,4-phenyl | —NH—(CH$_2$)$_3$—N(CH$_3$)$_2$ | | |
| 135 | C-V | —NH—(CH$_2$)$_2$— | H | H | —(CH$_2$)$_2$—NH—CH$_2$—Z—O—CH$_3$ Where Z = 1,4-phenyl | —NH—(CH$_2$)$_3$—N(CH$_3$)$_2$ | | |
| 136 | C-V | —NH—(CH$_2$)$_2$— | H | H | —(CH$_2$)$_2$—NH—CH$_2$—Z—O—Ph Where Z = 1,4-phenyl | —NH—(CH$_2$)$_3$—N(CH$_3$)$_2$ | | |
| 137 | C-V | —NH—(CH$_2$)$_2$— | H | H | —(CH$_2$)$_2$—NH—(CH$_2$)$_4$—S—CH$_3$ | —NH—(CH$_2$)$_3$—N(CH$_3$)$_2$ | | |

-continued

C-V COMPOUNDS

| No. | Class | Linker | N1 | N2 | V1 | C2 | R1 | R2 |
|-----|-------|--------|----|----|----|----|----|-----|
| 138 | C-V | —NH—(CH$_2$)$_2$— | H | H | —(CH$_2$)$_2$—N((CH$_2$)$_4$—S—CH$_3$)$_2$ | —NH—(CH$_2$)$_3$—N(CH$_3$)$_2$ | | |
| 139 | C-V | —NH—(CH$_2$)$_2$— | H | H | H | (trans-trans)CH=C(CH$_3$)—CH=C(CH$_3$)—CH=C(CH$_3$)$_2$ | —NH—CH$_2$— | |
| 140 | C-V | —NH—(CH$_2$)$_2$— | H | H | —(CH$_2$)$_2$—NH—CH$_2$—Ph | —NH—(CH$_2$)$_2$—O—CH$_3$ | | |
| 141 | C-V | —NH—(CH$_2$)$_2$— | H | H | —(CH$_2$)$_2$—NH—(CH$_2$)$_5$—CH$_3$ | —NH—(CH$_2$)$_2$—O—CH$_3$ | | |
| 142 | C-V | —NH—(CH$_2$)$_2$— | H | H | —(CH$_2$)$_2$—NH—(CH$_2$)$_3$—CH$_3$ | —NH—(CH$_2$)$_2$—O—CH$_3$ | | |
| 143 | C-V | —NH—(CH$_2$)$_2$— | H | H | —(CH$_2$)$_2$—NH—(CH$_2$)$_5$—CH$_3$ | OH | | |
| 144 | C-V | —NH—(CH$_2$)$_2$— | H | H | —(CH$_2$)$_2$—NH—(CH$_2$)$_3$—CH$_3$ | OH | | |
| 145 | C-V | —NH—(CH$_2$)$_2$— | H | H | —(CH$_2$)$_2$—NH—CH$_2$—Ph | OH | | |
| 146 | C-V | —NH—(CH$_2$)$_2$— | H | H | —(CH$_2$)$_2$—NH—CH—Z Where Z = 4-pyridyl | —NH—(CH$_2$)$_3$—N(CH$_3$)$_2$ | | |
| 147 | C-V | —NH—(CH$_2$)$_2$— | H | H | —(CH$_2$)$_2$—NH—CH—Z Where Z = 4-(N-(CH$_2$)$_2$CH$_3$)pyridyl | —NH—(CH$_2$)$_3$—N(CH$_3$)$_2$ | | |
| 148 | C-V | —NH—(CH$_2$)$_2$— | H | H | —(CH$_2$)$_2$—NH—CH—Z Where Z = 4-(N-(CH$_2$)$_5$CH$_3$)pyridyl | —NH—(CH$_2$)$_3$—N(CH$_3$)$_2$ | | |
| 149 | C-V | —NH—(CH$_2$)$_2$— | H | H | —(CH$_2$)$_2$—NH—C(O)—(CH$_2$)$_5$—S—S—(CH$_2$)$_3$—CH$_3$ | —NH—(CH$_2$)$_3$—N(CH$_3$)$_2$ | | |
| 150 | C-V | —NH—CH$_2$—C(O)—NH—(CH$_2$)$_2$— | H | H | H | —NH—(CH$_2$)$_3$—N(CH$_3$)$_2$ | | |
| 151 | C-V | —NH—(CH$_2$)$_5$—C(O)—NH—(CH$_2$)$_2$— | H | H | H | —NH—(CH$_2$)$_3$—N(CH$_3$)$_2$ | | |
| 152 | C-V | —NH—CH((CH$_2$)$_3$—CH$_3$)—C(O)—NH—(CH$_2$)$_2$— | H | H | H | —NH—(CH$_2$)$_3$—N(CH$_3$)$_2$ | | |
| 153 | C-V | —NH—(CH$_2$)$_2$—NH—C(O)—Z—C(O)—NH—(CH$_2$)$_2$— Where Z = 1,3 phenyl | H | H | H | —NH—(CH$_2$)$_3$—N(CH$_3$)$_2$ | | |
| 154 | C-V | —NH—(CH$_2$)$_2$—NH—C(O)—Z—C(O)—NH—(CH$_2$)$_2$— Where Z = 1,2 phenyl | H | H | H | —NH—(CH$_2$)$_3$—N(CH$_3$)$_2$ | | |
| 155 | C-V | —NH—(CH$_2$)$_2$—NH—C(O)—Z—C(O)—NH—(CH$_2$)$_2$— Where Z = 1,4 phenyl | H | H | H | —NH—(CH$_2$)$_3$—N(CH$_3$)$_2$ | | |
| 156 | C-V | —NH—(CH$_2$)$_2$—NH—C(O)—CH$_2$—C(O)—NH—(CH$_2$)$_2$— | H | H | H | —NH—(CH$_2$)$_3$—N(CH$_3$)$_2$ | | |
| 157 | C-V | —NH—(CH$_2$)$_2$—NH—C(O)—(CH$_2$)$_4$—C(O)—NH—(CH$_2$)$_2$— | H | H | H | —NH—(CH$_2$)$_3$—N(CH$_3$)$_2$ | | |

C-V COMPOUNDS

| No. | Class | Linker | N1 | N2 | V1 | C2 | R1 | R2 |
|---|---|---|---|---|---|---|---|---|
| 158 | C-V | —NH—(CH$_2$)$_2$—NH—C(O)—(CH$_2$)$_6$—C(O)—NH(CH$_2$)$_2$— | H | H | H | —NH—(CH$_2$)$_3$—N(CH$_3$)$_2$ | | |
| 159 | C-V | —NH—(CH$_2$)$_2$—NH—C(O)—(CH$_2$)$_2$—C(O)—NH—(CH$_2$)$_2$— | H | H | H | —NH—(CH$_2$)$_3$—Z Where Z = N-morpholino | | |
| 160 | C-V | —NH—CH$_2$—Z—C(O)—(CH$_2$)$_2$—C(O)—NH—(CH$_2$)$_2$— Where Z = N,3 piperidine | H | H | H | —NH—(CH$_2$)$_3$—N(CH$_3$)$_2$ | | |
| 161 | C-V | —NH—CH$_2$—Z—C(O)—(CH$_2$)$_2$—C(O)—NH—(CH$_2$)$_2$— Where Z = N,4 piperidine | H | H | H | —NH—(CH$_2$)$_3$—N(CH$_3$)$_2$ | | |
| 162 | C-V | —Z—C(O)—NH—(CH$_2$)$_2$— Where Z = N,3 piperidine | H | H | H | —NH—(CH$_2$)$_3$—N(CH$_3$)$_2$ | | |
| 163 | C-V | —NH—(CH$_2$)$_3$—C(O)—Z—CH$_2$— Where Z = N,3 piperidine | H | H | H | —NH—(CH$_2$)$_3$—N(CH$_3$)$_2$ | | |
| 164 | C-V | —NH—(CH$_2$)$_3$—C(O)—Z—CH$_2$— Where Z = N,4 piperidine | H | H | H | —NH—(CH$_2$)$_3$—N(CH$_3$)$_2$ | | |
| 165 | C-V | —NH—(CH$_2$)$_2$—C(O)—NH—(CH$_2$)$_2$— | H | H | H | —NH—(CH$_2$)$_3$—N(CH$_3$)$_2$ | | |
| 166 | C-V | —NH—CH((CH$_2$)$_4$—NHBoc)—C(O)—NH—(CH$_2$)$_2$— | H | H | H | —NH—(CH$_2$)$_3$—N(CH$_3$)$_2$ | | |
| 167 | C-V | —NH—(CH$_2$)$_2$—NH—C(O)—(CH$_2$)$_2$—C(O)—NH—(CH$_2$)$_2$— | H | H | H | OH | | |
| 168 | C-V | —NH—(CH$_2$)$_2$—NH—C(O)—(CH$_2$)$_2$—C(O)—NH—(CH$_2$)$_2$— | H | H | H | —NH—(CH$_2$)$_5$—CH$_3$ | | |
| 169 | C-V | —NH—(CH$_2$)$_2$—NH—C(O)—(CH$_2$)$_2$—C(O)—NH—(CH$_2$)$_2$— | H | H | H | —NH—(CH$_2$)$_5$—OH | | |
| 170 | C-V | —NH—(CH$_2$)$_2$—NH—C(O)—(CH$_2$)$_2$—C(O)—NH—(CH$_2$)$_2$— | H | H | H | -N-glucosamine | | |
| 171 | C-V | —NH—(CH$_2$)$_2$—NH—C(O)—(CH$_2$)$_2$—C(O)—NH—(CH$_2$)$_2$— | H | H | H | —NH—(CH$_2$)$_3$—SO$_3$H | | |
| 172 | C-V | —NH—(CH$_2$)$_2$—NH—C(O)—(CH$_2$)$_2$—C(O)—NH—(CH$_2$)$_2$— | H | H | H | —NH—(CH$_2$)$_2$—O—CH$_3$ | | |
| 173 | C-V | —NH—(CH$_2$)$_2$—NH—C(O)—(CH$_2$)$_2$—C(O)—NH—(CH$_2$)$_2$— | H | H | H | —NH—CH$_2$—(CH(OH))$_4$—CH$_2$OH | | |
| 174 | C-V | (S)—NH—CH(CH(CH$_3$)$_2$)—C(O)—NH—(CH$_2$)$_2$— | H | H | H | —NH—(CH$_2$)$_3$—N(CH$_3$)$_2$ | | |
| 175 | C-V | (R)—NH—CH(CH(CH$_3$)$_2$)—C(O)—NH—(CH$_2$)$_2$— | H | H | H | —NH—(CH$_2$)$_3$—N(CH$_3$)$_2$ | | |
| 176 | C-V | (cis)-NH—(CH$_2$)$_2$—C(O)—CH=CH—C(O)—NH—(CH$_2$)$_2$— | H | H | H | —NH—(CH$_2$)$_3$—N(CH$_3$)$_2$ | | |
| 177 | C-V | (trans)-NH—(CH$_2$)$_2$—C(O)—CH=CH—C(O)—NH—(CH$_2$)$_2$— | H | H | H | —NH—(CH$_2$)$_3$—N(CH$_3$)$_2$ | | |
| 178 | C-V | —NH—(CH$_2$)$_2$—C(O)—Z—C(O)—NH—(CH$_2$)$_2$— Where Z = 1,2 cyclopropyl | H | H | H | —NH—(CH$_2$)$_3$—N(CH$_3$)$_2$ | | |
| 179 | C-V | —NH—(CH$_2$)$_2$—NH—C(O)—(CH$_2$)$_2$—C(O)—NH—(CH$_2$)$_2$— | H | H | H | —NH—(CH$_2$)$_2$—Z Where Z = N-piperidine | | |

-continued

C-V COMPOUNDS

| No. | Class | Linker | N1 | N2 | V1 | C2 | R1 | R2 |
|---|---|---|---|---|---|---|---|---|
| 180 | C-V | —NH—(CH$_2$)$_2$—NH—C(O)—(CH$_2$)$_3$—C(O)—NH—(CH$_2$)$_2$— | H | H | H | —NH—(CH$_2$)$_3$—N(CH$_3$)$_2$ | | |
| 181 | C-V | —NH—(CH$_2$)$_2$—NH—CH((CH$_2$)—CH(CH$_3$)$_2$)—C(O)—NH—(CH$_2$)$_2$— | H | H | H | —NH—(CH$_2$)$_3$—N(CH$_3$)$_2$ | | |
| 182 | C-V | (R)—NH—(CH$_2$)$_2$—NH—CH((CH$_3$)$_2$)—C(O)—NH—(CH$_2$)$_2$— | H | H | H | —NH—(CH$_2$)$_3$—N(CH$_3$)$_2$ | | |
| 183 | C-V | (S)—NH—(CH$_2$)$_2$—NH—CH((CH$_3$)$_2$)—C(O)—NH—(CH$_2$)$_2$— | H | H | H | —NH—(CH$_2$)$_3$—N(CH$_3$)$_2$ | | |
| 184 | C-V | —NH—(CH$_2$)$_2$—NH—C(O)—(CH$_2$)$_2$—C(O)—NH—(CH$_2$)$_2$— | H | H | H | —NH—(CH$_2$)$_4$—CH$_3$ | | |
| 185 | C-V | —NH—(CH$_2$)$_2$—NH—C(O)—(CH$_2$)$_2$—C(O)—NH—(CH$_2$)$_2$— | H | H | H | —NH—(CH$_2$)$_3$—CH$_3$ | | |
| 186 | C-V | —NH—(CH$_2$)$_2$—NH—C(O)—(CH$_2$)$_2$—C(O)—NH—(CH$_2$)$_2$— | H | H | H | —NH—(CH$_2$)$_6$—CH$_3$ | | |
| 187 | C-V | —NH—(CH$_2$)$_2$—NH—C(O)—(CH$_2$)$_2$—C(O)—NH—(CH$_2$)$_2$— | H | H | H | —NH—CH$_2$—Ph | | |
| 188 | C-V | —NH—(CH$_2$)$_2$—NH—C(O)—(CH$_2$)$_2$—C(O)—NH—(CH$_2$)$_2$— | H | H | H | —NH—(CH$_2$)$_2$—OH | | |
| 189 | C-V | —NH—(CH$_2$)$_2$—NH—C(NH)—(CH$_2$)$_6$—C(NH)—NH—(CH$_2$)$_2$— | H | H | H | —NH—(CH$_2$)$_3$—N(CH$_3$)$_2$ | | |
| 190 | C-V | —NH—(CH$_2$)$_2$—NH—C(O)—(CH$_2$)$_2$—C(O)—NH—(CH$_2$)$_2$— | H | H | H | —NH—(CH$_2$)$_2$—CH$_3$ | | |
| 191 | C-V | —NH—(CH$_2$)$_2$—NH—C(O)—(CH$_2$)$_2$—C(O)—NH—(CH$_2$)$_2$— | H | H | H | —NH—Z Where Z = cyclobutyl | | |
| 192 | C-V | —NH—(CH$_2$)$_2$—NH—C(O)—(CH$_2$)$_2$—C(O)—NH—(CH$_2$)$_2$— | H | H | H | —NH—CH$_2$—COOH | | |
| 193 | C-V | —NH—(CH$_2$)$_2$—NH—C(O)—(CH$_2$)$_2$—C(O)—NH—(CH$_2$)$_2$— | H | H | H | —NH—(CH$_2$)$_4$—NH—C(NH)—NH$_2$ | | |
| 194 | C-V | —NH—(CH$_2$)$_{11}$—NH—C(O)—(CH$_2$)$_2$—C(O)—NH—(CH$_2$)$_2$— | H | H | H | —NH—(CH$_2$)$_3$—N(CH$_3$)$_2$ | | |
| 195 | C-V | —NH—(CH$_2$)$_2$—NH—C(O)—(CH$_2$)$_2$—C(O)—NH—(CH$_2$)$_2$— | H | H | H | —NH—CH(COOH)—(CH$_2$)$_3$—NH—C(NH)—NH$_2$ | | |
| 196 | C-V | —NH—(CH$_2$)$_2$—NH—C(O)—(CH$_2$)$_2$—C(O)—NH—(CH$_2$)$_2$— | H | H | H | —NH—CH(COOH)—CH$_2$—COOH | | |
| 197 | C-V | —NH—(CH$_2$)$_2$—NH—C(O)—(CH$_2$)$_2$—C(O)—NH—(CH$_2$)$_2$— | H | H | H | —NH—CH(COOH)—(CH$_2$)$_3$—CH$_3$ | | |
| 198 | C-V | (R)—NH—CH((CH$_2$)$_4$—NH$_2$)—C(O)—NH—(CH$_2$)$_2$— | H | H | H | —NH—(CH$_2$)$_3$—N(CH$_3$)$_2$ | | |
| 199 | C-V | —NH—(CH$_2$)$_2$—NH—C(O)—(CH$_2$)$_2$—C(O)—NH—(CH$_2$)$_2$— | H | H | H | NH—CH$_2$—Z Where Z = 2-furan | | |
| 200 | C-V | —NH—(CH$_2$)$_2$—NH—C(O)—(CH$_2$)$_2$—C(O)—NH—(CH$_2$)$_2$— | H | H | H | NH—Z Where Z = cyclohexane | | |
| 201 | C-V | —NH—(CH$_2$)$_2$—NH—C(O)—(CH$_2$)$_2$—C(O)—NH—(CH$_2$)$_2$— | H | H | H | -N-piperidine | | |
| 202 | C-V | —Z—C(O)—NH—(CH$_2$)$_2$— Where Z = N,4 piperidine | H | H | H | —NH—(CH$_2$)$_3$—N(CH$_3$)$_2$ | | |
| 203 | C-V | —NH—(CH$_2$)$_2$—NH—(CH$_2$)$_5$—C(O)—NH—(CH$_2$)$_2$— | H | H | H | —NH—(CH$_2$)$_3$—N(CH$_3$)$_2$ | | |

-continued

C-V COMPOUNDS

| No. | Class | Linker | N1 | N2 | V1 | C2 | R1 | R2 |
|---|---|---|---|---|---|---|---|---|
| 204 | C-V | —NH—(CH$_2$)$_4$—CH(NH$_2$)—C(O)—NH—(CH$_2$)$_2$— | H | H | H | —NH—(CH$_2$)$_3$—N(CH$_3$)$_2$ | | |
| 205 | C-V | —NH—(CH$_2$)$_2$—NH—C(O)—(CH$_2$)$_2$—C(O)—NH—(CH$_2$)$_2$— | H | H | H | —NH—(CH$_2$)$_3$—N$^+$(CH$_3$)$_3$ | | |
| 206 | C-V | —NH—(CH$_2$)$_2$—NH—C(O)—(CH$_2$)$_2$—C(O)—NH—(CH$_2$)$_2$— | H | H | H | N((CH$_2$)$_3$CH$_3$)$_2$ | | |
| 207 | C-V | —NH—(CH$_2$)$_2$—NH—C(O)—(CH$_2$)$_2$—C(O)—NH—(CH$_2$)$_2$— | H | H | H | NH—(CH$_2$)$_3$—Z<br>Where Z = imidazol-1-yl | | |
| 208 | C-V | —NH—(CH$_2$)$_2$—NH—C(O)—(CH$_2$)$_2$—C(O)—NH—(CH$_2$)$_2$— | H | H | H | —N(CH$_2$)$_3$—NH—<br>(CH$_2$)$_2$—CH$_3$ | | |
| 209 | C-V | —NH—(CH$_2$)$_2$—NH—C(O)—(CH$_2$)$_2$—C(O)—NH—(CH$_2$)$_2$— | H | H | H | 4-(N-piperidino)-piperidino⊕ | | |
| 210 | C-V | —NH—(CH$_2$)$_2$—NH—C(O)—(CH$_2$)$_2$—C(O)—NH—(CH$_2$)$_2$— | H | H | H | —NH—CH$_2$—Z<br>Where Z = 4-pyridino | | |
| 211 | C-V | —NH—(CH$_2$)$_2$— | H | H | —(CH$_2$)$_2$—NH—(CH$_2$)$_9$—CH$_3$ | —NH—(CH$_2$)$_3$—O—(CH$_2$)$_2$—<br>O—(CH$_2$)$_2$—O—(CH$_2$)$_3$—<br>NH—C(O)—CH$_2$—O—CH$_3$ | | |
| 212 | C-V | —NH—(CH$_2$)$_2$—NH—C(O)—(CH$_2$)$_2$—C(O)—NH—(CH$_2$)$_2$— | H | H | H | —N(CH$_3$)—(CH$_2$)$_3$—N(CH$_3$)—<br>CH$_2$—C(O)—NH—Z<br>Where Z = 2,6-dimethylphenyl | | |
| 213 | C-V | —NH—(CH$_2$)$_2$—NH—C(O)—(CH$_2$)$_2$—C(O)—NH—(CH$_2$)$_2$— | H | H | H | —NH—(CH$_2$)$_3$—N(CH$_3$)$_2$ | | |
| 214 | C-V | —NH—(CH$_2$)$_2$—NH—C(O)—(CH$_2$)$_2$—C(O)—NH—(CH$_2$)$_2$— | H | H | H | —NH—(CH$_2$)$_7$—N(CH$_3$)$_2$ | | |
| 215 | C-V | —NH—(CH$_2$)$_2$—NH—C(O)—(CH$_2$)$_2$—C(O)—NH—(CH$_2$)$_2$— | H | H | H | —N((CH$_2$)$_3$—N(CH$_3$)$_2$)$_2$ | | |
| 216 | C-V | —NH—(CH$_2$)$_2$— | H | H | H | —NH—(CH$_2$)$_2$—NH—<br>(CH$_2$)$_7$—CH$_3$ | | |
| 217 | C-V | —NH—(CH$_2$)$_2$— | H | H | H | —NH—(CH$_2$)$_2$—N(CH$_3$)$_2$—<br>CH$_3$ | | |
| 218 | C-V | —NH—(CH$_2$)$_2$— | H | H | —(CH$_2$)$_2$—NH—(CH$_2$)$_9$—CH$_3$ | —NH—CH(COOH)(CH$_2$—<br>COOH) | | |
| 219 | C-V | —NH—(CH$_2$)$_2$— | H | H | —(CH$_2$)$_2$—NH—(CH$_2$)$_9$—CH$_3$ | NH—(CH$_2$)$_2$—(O—(CH$_2$)$_2$)$_8$—<br>O—CH$_3$ | | |
| 220 | C-V | N(CH$_3$)—(CH$_2$)$_2$—N(CH$_3$)—C(O)—(CH$_2$)$_2$—C(O)—N(CH$_3$)—(CH$_2$)$_2$— | H | H | H | —N(CH$_3$)—(CH$_2$)$_3$—N(CH$_3$)$_2$ | | |
| 221 | C-V | —NH—(CH$_2$)$_2$— | H | H | H | —NH—(CH$_2$)$_3$—N(CH$_3$)$_2$ | | |
| 222 | C-V | —NH—(CH$_2$)$_2$—NH—C(O)—(CH$_2$)$_2$— | H | H | —(CH$_2$)$_5$—CH$_3$ | -N-glucosamine | —CH$_2$—Z<br>Where Z = N-methyl-D-glucamine | |

-continued

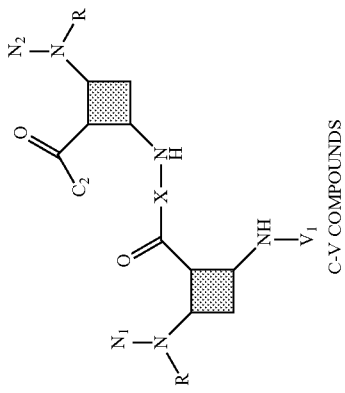

C-V COMPOUNDS

| No. | Class | Linker | N1 | N2 | V1 | C2 | R1 | R2 |
|---|---|---|---|---|---|---|---|---|
| 223 | C-V | —NH—(CH$_2$)$_2$—NH—C(O)—(CH$_2$)$_2$—C(O)—NH—(CH$_2$)$_2$— | H | H | —(CH$_2$)$_7$—CH$_3$ | -N-glucosamine | | |
| 224 | C-V | —NH—(CH$_2$)$_2$—NH—C(O)—(CH$_2$)$_2$—C(O)—NH—(CH$_2$)$_2$— | H | H | —(CH$_2$)$_9$—CH$_3$ | -N-glucosamine | | |
| 225 | C-V | —NH—(CH$_2$)$_2$—NH—C(O)—(CH$_2$)$_2$—C(O)—NH—(CH$_2$)$_2$— | H | H | —CH$_2$—Ph | -N-glucosamine | | |
| 226 | C-V | —NH—(CH$_2$)$_2$—NH—C(O)—(CH$_2$)$_2$—C(O)—NH—(CH$_2$)$_2$— | H | H | —CH$_2$—Z Where Z = biphenyl | -N-glucosamine | | |
| 227 | C-V | —NH—(CH$_2$)$_2$—NH—C(O)—(CH$_2$)$_2$—C(O)—NH—(CH$_2$)$_2$— | H | H | —(CH$_2$)$_5$—NH—(CH$_2$)$_7$—CH$_3$ | -N-glucosamine | | |
| 228 | C-V | —NH—(CH$_2$)$_2$—NH—C(O)—(CH$_2$)$_2$—C(O)—NH—(CH$_2$)$_2$— | H | H | —(CH$_2$)$_2$—NH—(CH$_2$)$_9$—CH$_3$ | -N-glucosamine | | |
| 229 | C-V | —NH—(CH$_2$)$_2$—NH—C(O)—(CH$_2$)$_2$—C(O)—NH—(CH$_2$)$_2$— | H | H | —(CH$_2$)$_2$—NH—(CH$_2$)$_9$—CH$_3$ | -N-glucosamine | | |
| 230 | C-V | —NH—(CH$_2$)$_2$—NH—C(O)—(CH$_2$)$_2$—C(O)—NH—(CH$_2$)$_2$— | H | H | —(CH$_2$)$_2$—NH—CH$_2$—Ph | -N-glucosamine | | |
| 231 | C-V | —NH—(CH$_2$)$_2$—NH—C(O)—(CH$_2$)$_2$—C(O)—NH—(CH$_2$)$_2$— | H | H | —(CH$_2$)$_2$—NH—Z Where Z = biphenyl | -N-glucosamine | | |
| 232 | C-V | —NH—CH(COOH)—CH$_2$—C(O)—NH—(CH$_2$)$_2$— | H | H | —(CH$_2$)$_2$—NH—(CH$_2$)$_9$—CH$_3$ | OH | | |
| 233 | C-V | —NH—CH(COOH)—CH$_2$—C(O)—NH—(CH$_2$)$_2$— | H | H | —(CH$_2$)$_2$—NH—(CH$_2$)$_9$—CH$_3$ | —NH—(CH$_2$)$_3$—Z Where Z = N-morpholino | | |
| 234 | C-V | —NH—CH(COOH)—CH$_2$—C(O)—NH—(CH$_2$)$_2$— | H | H | —(CH$_2$)$_2$—NH—(CH$_2$)$_9$—CH$_3$ | -N-glucosamine | | |
| 235 | C-V | —NH—(CH$_2$)$_2$— | H | H | —(CH$_2$)$_5$—CH$_3$ | —NH—(CH$_2$)$_3$—N(CH$_3$)$_2$ | | |
| 236 | C-V | —NH—(CH$_2$)$_2$— | H | H | —(CH$_2$)$_7$—CH$_3$ | —NH—(CH$_2$)$_3$—N(CH$_3$)$_2$ | | |
| 237 | C-V | —NH—(CH$_2$)$_2$— | H | H | —(CH$_2$)$_5$—CH$_3$ | —NH—(CH$_2$)$_3$—N(CH$_3$)$_2$ | | |
| 238 | C-V | —NH—(CH$_2$)$_2$— | H | H | —(CH$_2$)$_7$—CH$_3$ | —NH—(CH$_2$)$_3$—N(CH$_3$)$_2$ | | |
| 239 | C-V | —NH—(CH$_2$)$_2$— | H | H | —CH$_2$—Z Where Z = biphenyl | —NH—(CH$_2$)$_3$—N(CH$_3$)$_2$ | | |
| 240 | C-V | —NH—CH(C(O)—Z)—CH$_2$—C(O)—NH—(CH$_2$)$_2$— Where Z = N-glucosamine | H | H | —(CH$_2$)$_2$—NH—(CH$_2$)$_9$—CH$_3$ | —NH—(CH$_2$)$_3$—N(CH$_3$)$_2$ | | |
| 241 | C-V | —NH—CH(C(O)—Z)—CH$_2$—C(O)—NH—(CH$_2$)$_2$— Where Z = N-morpholino | H | H | —(CH$_2$)$_2$—NH—(CH$_2$)$_9$—CH$_3$ | -N-glucosamine | | |
| 242 | C-V | —NH—CH(C(O)—NH—(CH$_2$)$_3$—N(CH$_3$)$_2$)—CH$_2$—C(O)—NH—(CH$_2$)$_2$— | H | H | —(CH$_2$)$_2$—NH—(CH$_2$)$_9$—CH$_3$ | -N-glucosamine | | |
| 243 | C-V | —NH—CH(C(O)—NH—(CH$_2$)$_2$—Z)—CH$_2$—C(O)—NH—(CH$_2$)$_2$— Where Z = N-morpholino | H | H | —(CH$_2$)$_2$—NH—(CH$_2$)$_9$—CH$_3$ | -N-glucosamine | | |
| 244 | C-V | —Z—C(O)—NH—(CH$_2$)$_2$— Where Z = N,3 piperidine | H | H | —(CH$_2$)$_5$—CH$_3$ | —NH—(CH$_2$)$_5$—CH$_3$ | | |
| 245 | C-V | —NH—CH(C(O)—NH—(CH$_2$)$_2$—Z)—CH$_2$—C(O)—NH—(CH$_2$)$_2$— Where Z = N-morpholino | H | H | —(CH$_2$)$_2$—NH—(CH$_2$)$_9$—CH$_3$ | —NH—(CH$_2$)$_3$—Z Where Z = N-morpholino | | |

-continued

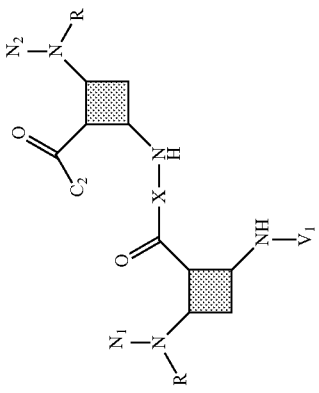

C-V COMPOUNDS

| No. | Class | Linker | N1 | N2 | V1 | C2 | R1 | R2 |
|---|---|---|---|---|---|---|---|---|
| 246 | C-V | —NH—CH(C(O)—Z)—CH$_2$—C(O)—NH—(CH$_2$)$_2$— Where Z = N-glucosamine | | H | —(CH$_2$)$_2$—NH—(CH$_2$)$_9$—CH$_3$ | —NH—(CH$_2$)$_3$—Z Where Z = N-morpholino | | —CH$_2$—Z Where Z = N-methyl-D-glucamine |
| 247 | C-V | —NH—(CH$_2$)$_2$— | H | H | —(CH$_2$)$_2$—NH—(CH$_2$)$_9$—CH$_3$ | OH | | —CH$_2$— —NH— (CH$_2$)$_3$— N(CH$_3$)$_2$ |
| 248 | C-V | —NH—(CH$_2$)$_2$— | H | H | —(CH$_2$)$_2$—NH—(CH$_2$)$_9$—CH$_3$ | OH | | —CH$_2$—Z Where Z = N-methyl-D-glucamine |
| 249 | C-V | —NH—(CH$_2$)$_2$— | H | H | —(CH$_2$)$_2$—NH—(CH$_2$)$_9$—CH$_3$ | D-glucosamide | | —CH$_2$— —NH— (CH$_2$)$_3$— N(CH$_3$)$_2$ |
| 250 | C-V | —NH—(CH$_2$)$_2$— | H | H | —(CH$_2$)$_2$—NH—(CH$_2$)$_9$—CH$_3$ | D-glucosamide | | —CH$_2$—Z Where Z = N-methyl-D-glucamine |
| 251 | C-V | —NH—(CH$_2$)$_2$— | H | H | —(CH$_2$)$_2$—NH—(CH$_2$)$_9$—CH$_3$ | —NH—(CH$_2$)$_3$—N(CH$_3$)$_2$ | | —CH$_2$— —NH— (CH$_2$)$_3$— N(CH$_3$)$_2$ |
| 252 | C-V | —NH—(CH$_2$)$_2$— | H | H | —(CH$_2$)$_2$—NH—(CH$_2$)$_9$—CH$_3$ | —NH—(CH$_2$)$_3$—N(CH$_3$)$_2$ | | —CH$_2$—Z Where Z = N-methyl-D-glucamine |

| No. | Class | Linker | N1 | N2 | V1 | C2 | R1 | R2 |
|---|---|---|---|---|---|---|---|---|
| 253 | C-V | —NH—(CH₂)₂— | H | H | —(CH₂)₂—NH—(CH₂)₉—CH₃ | OH | | —CH₂—Z Where Z = N-methyl-D-glucamine |
| 254 | C-V | —NH—(CH₂)₂—NH—C(O)—(CH₂)₂—C(O)—NH—(CH₂)₂— | H | H | —(CH₂)₂—NH—(CH₂)₅—CH₃ | —NH—(CH₂)₃—N(CH₃)₂ | | |
| 255 | C-V | —NH—(CH₂)₂—NH—C(O)—(CH₂)₂—C(O)—NH—(CH₂)₂— | H | H | —(CH₂)₂—NH—(CH₂)₇—CH₃ | —NH—(CH₂)₃—N(CH₃)₂ | | |
| 256 | C-V | —NH—(CH₂)₂— | H | H | —(CH₂)₂—NH—(CH₂)₉—CH₃ | -N-glucosamine | —CH₂—Z Where Z = N-methyl-D-glucamine | |
| 257 | C-V | —NH—(CH₂)₂— | H | H | —(CH₂)₂—NH—(CH₂)₉—CH₃ | —NH—(CH₂)₃—N(CH₃)₂ | —CH₂—Z Where Z = N-methyl-D-glucamine | |
| 258 | C-V | —NH—(CH₂)₂— | H | H | —(CH₂)₂—NH—(CH₂)₉—CH₃ | OH | | —CH₂—Z Where Z = N-methyl-D-glucamine |
| 259 | C-V | —NH—(CH₂)₂— | H | H | —(CH₂)₂—NH—(CH₂)₉—CH₃ | -N-glucosamine | | —CH₂—Z Where Z = N-methyl-D-glucamine |
| 260 | C-V | —NH—(CH₂)₂—NH—C(O)—(CH₂)₂—C(O)—NH—(CH₂)₂— | H | H | H | —NH—(CH₂)₂—N((CH₂)₂—OH)₂ | | |
| 261 | C-V | —NH—(CH₂)₂— | H | H | H | —NH—(CH₂)₂—NH₂ | | |
| 262 | C-V | —NH—(CH₂)₂— | H | H | —(CH₂)₂—NH—(CH₂)₉—CH₃ | —NH—CH(C(O)—Z)—C(O)—Z) Where Z = N-glucosamine | | |
| 263 | C-V | —NH—(CH₂)₂— | ⊕ | H | H | —NH—(CH₂)₃—N(CH₃)₂ | | |
| 264 | C-V | —NH—(CH₂)₂— | H | ⊕ | H | OH | | |
| 265 | C-V | —NH—(CH₂)₂—NH—C(O)—(CH₂)₂—C(O)—NH—(CH₂)₂— | ⊕ | H | H | —NH—(CH₂)₃—N(CH₃)₂ | | |

C-V COMPOUNDS

| No. | Class | Linker | N1 | N2 | V1 | C2 | R1 | R2 |
|---|---|---|---|---|---|---|---|---|
| 266 | C-V | —NH—(CH₂)₂— | H | H | —(CH₂)₂—NH—(CH₂)₉—CH₃ | OH | | —CH₂—NH—(CH₂)₂—OH |
| 267 | C-V | —NH—(CH₂)₂—NH—C(O)—(CH₂)₂—C(O)—NH—(CH₂)₂— | H | H | —(CH₂)₂—NH—(CH₂)₉—CH₃ | —NH—(CH₂)₃—N(CH₃)₂ | | |
| 268 | C-V | —NH—(CH₂)₂—NH—C(O)—(CH₂)₂—C(O)—NH—(CH₂)₂— | H | H | —(CH₂)₂—NH—CH₂—Ph | —NH—(CH₂)₃—N(CH₃)₂ | | |
| 269 | C-V | —NH—(CH₂)₂—NH—C(O)—(CH₂)₂—C(O)—NH—(CH₂)₂— | H | H | —(CH₂)₂—N((CH₃)₉—CH₃)—Z Where Z = 9-fluroenyl methoxycarbonyl | OH | | |
| 270 | C-V | —NH—(CH₂)₂— | H | H | —CH₂—Z Where Z = 4-(4'-chloro) biphenyl | OH | | |
| 271 | C-V | —NH—(CH₂)₂—NH—C(O)—(CH₂)₂—C(O)—NH—(CH₂)₂— | H | H | —CH₂—Z Where Z = 4-(4'-chloro) biphenyl | OH | | |
| 272 | C-V | —NH—CH(C(O)—Z)—CH₂—C(O)—NH—(CH₂)₂— Where Z = N-glucosamine | H | H | —(CH₂)₂—NH—(CH₂)₉—CH₃ | OH | | |
| 273 | C-V | —NH—(CH₂)₂— | H | H | —(CH₂)₂—NH—CH₂—Z—Cl Where Z = 4,4'-biphenyl | OH | | |
| 274 | C-V | —NH—(CH₂)₂—NH—C(O)—(CH₂)₂—C(O)—NH—(CH₂)₂— | H | H | —(CH₂)₂—NH—CH₂—Z—Cl Where Z = 4,4'-biphenyl | OH | | |
| 275 | C-V | —NH—(CH₂)₂—NH—C(O)—(CH₂)₂—C(O)—NH—(CH₂)₂— | H | H | —(CH₂)₂—NH—(CH₂)₉—CH₃ | OH | —CH₂—Z Where Z = N-methyl-D-glucamine | |
| 276 | C-V | —NH—(CH₂)₂—NH—C(O)—(CH₂)₂—C(O)—NH—(CH₂)₂— | H | H | —(CH₂)₂—NH—(CH₂)₉—CH₃ | N-glucosamine | —CH₂—Z Where Z = N-methyl-D-glucamine | |
| 277 | C-V | —NH—(CH₂)₂—NH—C(O)—(CH₂)₂—C(O)—NH—(CH₂)₂— | H | H | —(CH₂)₂—NH—(CH₂)₉—CH₃ | OH | | —CH₂—Z Where Z = N-methyl-D-glucamine |

-continued

C-V COMPOUNDS

| No. | Class | Linker | N1 | N2 | V1 | C2 | R1 | R2 |
|---|---|---|---|---|---|---|---|---|
| 278 | C-V | —NH—$(CH_2)_2$—NH—C(O)—$(CH_2)_2$—C(O)—NH—$(CH_2)_2$— | H | H | —$(CH_2)_2$—NH—$(CH_2)_9$—$CH_3$ | N-glucosamine | | —$CH_2$—Z Where Z = N-methyl-D-glucamine |
| 279 | C-V | —NH—$(CH_2)_2$—NH—C(O)—$(CH_2)_2$—C(O)—NH—$(CH_2)_2$— | H | H | —$(CH_2)_2$—NH—$(CH_2)_7$—$CH_3$ | OH | | |
| 280 | C-V | —NH—$(CH_2)_2$—NH—C(O)—$(CH_2)_2$—C(O)—NH—$(CH_2)_2$— | H | H | —$(CH_2)_2$—NH—$(CH_2)_9$—$CH_3$ | OH | | |
| 290 | C-V | —NH—$(CH_2)_2$—NH—C(O)—$(CH_2)_2$—C(O)—NH—$(CH_2)_2$— | H | H | H | OH | | —$CH_2$—Z Where Z = N-methyl-D-glucamine |
| 291 | C-V | —NH—$(CH_2)_2$—NH—C(O)—$(CH_2)_2$—C(O)—NH—$(CH_2)_2$— | H | H | —$(CH_2)_9$—$CH_3$ | OH | | |
| 292 | C-V | —NH—$(CH_2)_2$—NH—C(O)—$(CH_2)_2$—C(O)—NH—$(CH_2)_2$— | H | H | —$(CH_2)_7$—$CH_3$ | OH | | |
| 293 | C-V | —NH—$(CH_2)_2$—NH—C(O)—$(CH_2)_2$—C(O)—NH—$(CH_2)_2$— | H | H | —$(CH_2)_2$—NH—$(CH_2)_8$—$CH_3$ | N-glucosamine | | |
| 294 | C-V | —NH—$(CH_2)_2$—NH—C(O)—$(CH_2)_2$—C(O)—NH—$(CH_2)_2$— | H | H | —$(CH_2)_2$—NH—$(CH_2)_8$—$CH_3$ | OH | | |

⊕indicates that the substituent is N-desmethylvancomycin (R=H)

Preparation of other [C—V] Compounds of Formula I

Following the procedures of Examples 14–20, other [C—V] compounds of Formula I are prepared, including those where the ligand is optionally substituted vancomycin, optionally substituted N-desmethylvancomycin, or optionally substituted chloroeremomycin.

EXAMPLE 21

Preparation of a [C—N] Compound of Formula I

Preparation of a Compound of Formula I

The compound of formula (43) prepared in Example 9 (6.20 mg, 3.14 μmol) was dissolved in 500 μL of DMF. The compound of formula (72) prepared in Example 14 (4.15 mg, 3.14 μmol) was added to the solution, followed by PyBOP (2.44 mg, 4.8 μmol), HOBt(0.65 mg, 4.8 μmol) and Hunig's base (6.7 μL, 38.4 μmol)). The reaction solution was added dropwise to 20 mL of acetonitrile, giving a precipitate that was collected by centrifugation. The precipitate was purified by reverse-phase HPLC on a Ranin C18 Dynamax column (2.5 cm×25 cm, 8 μm particle size), at 10 mL/min flow rate using 0.045% TFA in water as buffer A and 0.045% TFA in acetonitrile as buffer B (HPLC gradient of 2–50% B over 90 minutes), which yielded a compound of Formula I as its trifluroacetate salt. MS calculated: $MH^+$, 3533; Found, 3533.

EXAMPLE 23

Preparation of a [C—R] Compound of Formula I (1) To 50% aqueous acetonitrile (5.0 mL) was added diaminoethane (120 mg, 2.0 mmol), 37% formalin (32 uL, 0.42 mmol) and [C]-dimethylaminopropylamide vancomycin (744 mg, 0.40 mmol). After stirring for 4 h, the product was precipitated by the additon of acetonitrile (40 mL). The solid was isolated by centrifugation, then washed with ether (40 mL). The resulting solid was dried in vacuo, and purified by reverse-phase HPLC (5–30% acetonitrile in water containing 0.1% trifluoroacetic acid over 40 min at a flow rate of 50 ml/min). Fractions containing the desired product were identified by mass spectrometry, pooled, and lyophilized to give [R]-N-(aminoethyl)aminomethyl [C]-dimethylaminopropylamide vancomycin (448 mg) as a white powder. MS calculated (MH+), 1606.5; found, 1606.3.

(2) To a solution of vancomycin hydrochloride (34 mg, 0.023 mmol) and [R]-(N-aminoethyl)aminomethyl-vancomycin-[C]-dimethylaminopropylamide in dimethylformamide (1.0 mL) and dimethylsulfoxide (1.0 mL) was added sequentially N,N-diisopropylethylamine (14 uL, 0.078 mmol), and a solution of PyBOP and HOBt in DMF (0.26 mL of a solution 0.1M in each, 0.026 mmol each). After 2 hours, the product was precipitated by the addition of acetonitrile (40 mL) and isolated by centrifugation. The solid product was washed with ether (40 mL) and dried in vacuo. Reverse phase preprative HPLC (2–20% acetonitrile in water containing 0.1% trifluoroacetic acid over 90 min) gave the title product as its trifluoroacetate salt. MS calculated (M+) 3036.8; found 3035.5.

| No. | Class | Linker | V1 | C2 | N1 | V2 | R1 | R2 |
|---|---|---|---|---|---|---|---|---|
| 1 | C-N | —NH—(CH$_2$)$_2$— | —(CH$_2$)$_2$—NH$_2$ | H | H | H | — | — |
| 2 | C-N | —NH—(CH$_2$)$_2$— | —(CH$_2$)$_2$—NH—CH$_2$—Z Where Z = biphenyl | —NH—(CH$_2$)$_3$—N(CH$_3$)$_2$ | H | H | — | — |
| 3 | C-N | —NH—(CH$_2$)$_2$— | —(CH$_2$)$_2$—NH—(CH$_2$)$_9$—CH$_3$ | —NH—(CH$_2$)$_3$—N(CH$_3$)$_2$ | H | H | — | — |
| 4 | C-N | —NH—(CH$_2$)$_2$— | —(CH$_2$)$_2$—NH—(CH$_2$)$_5$—CH$_3$ Where Z = biphenyl | —NH—(CH$_2$)$_3$—N(CH$_3$)$_2$ | H | H | — | — |

| No. | Class | Linker | R1 | C2 | V1 | V2 | R1 | N2 |
|---|---|---|---|---|---|---|---|---|
| 1 | C-R | —NH—(CH$_2$)$_2$—NH—CH$_2$— | — | —NH—(CH$_2$)$_3$—N(CH$_3$)$_2$ | H | H | — | H |

| No. | Class | Linker | C1 | C2 | V1 | V2 | R1 | R2 |
|---|---|---|---|---|---|---|---|---|
| 1 | N-V | —(CH$_2$)$_2$—NH—C(O)—(CH$_2$)$_3$—C(O)—NH—(CH$_2$)$_2$— | —NH—(CH$_2$)$_3$—N(CH$_3$)$_2$ | —NH—(CH$_2$)$_3$—N(CH$_3$)$_2$ | H | H | — | — |

| No. | Class | Linker | C1 | C2 | N1 | N2 | R1 | R2 |
|---|---|---|---|---|---|---|---|---|
| 1 | O-V | —CH$_2$—C(O)—NH—(CH$_2$)$_2$— | —NH—(CH$_2$)$_3$—N(CH$_3$)$_2$ | —NH—(CH$_2$)$_3$—N(CH$_3$)$_2$ | H | H | — | — |
| 2 | O-V | —CH$_2$—C(O)—NH—(CH$_2$)$_2$—NH—C(O)—(CH$_2$)$_3$—C(O)—NH—CH$_2$— | —NH—(CH$_2$)$_3$N(CH$_3$)$_2$ | —NH—(CH$_2$)$_3$—N(CH$_3$)$_2$ | H | H | — | — |

| No. | Class | Linker | N1 | N2 | C2 | | R1 | |
|---|---|---|---|---|---|---|---|---|
| 7 | C-O | —NH—(CH$_2$)$_2$—NH—C(O)—(CH$_2$)$_3$—C(O)—NH—(CH$_2$)$_2$— | H | H | —NH—(CH$_2$)$_3$—N(CH$_3$)$_2$ | | — | |

Teicoplanin Derivatives

| No. | Class | Linker | V1 | V2 | N1 | N2 | | |
|---|---|---|---|---|---|---|---|---|
| 60 | C$_T$-C | —NH—(CH$_2$)$_2$—NH—C(O)—(CH$_2$)$_3$—C(O)—NH—(CH$_2$)$_2$—NH— | —C(O)—(CH$_2$)$_8$—CH$_3$ | H | H | H | | |
| 61 | C$_T$-C | —NH—(CH$_2$)$_2$—NH—C(O)—(CH$_2$)$_3$—C(O)—NH—(CH$_2$)$_2$—NH— | —C(O)—(CH$_2$)$_7$—CH(CH$_3$)$_2$ | H | H | H | | |

| No. | Class | Linker | V1 | C2 | R1 | R2 | | |
|---|---|---|---|---|---|---|---|---|
| 75 | C$_T$-V | —NH—(CH$_2$)$_2$— | —C(O)—(CH$_2$)$_8$—CH$_3$ | —NH—(CH$_2$)$_3$—N(CH$_3$)$_2$ | — | — | | |
| 76 | C$_T$-V | —NH—(CH$_2$)$_2$— | —C(O)—(CH$_2$)$_7$—CH(CH$_3$)$_2$ | —NH—(CH$_2$)$_3$—N(CH$_3$)$_2$ | — | — | | |

Preparation of other Compounds of Formula I

Following the procedures of Example 21–22, other [C—N], [C—R], and [N—V] compounds of Formula I are prepared, including those where the ligand is optionally substituted vancomycin, optionally substituted N-desmethylvancomycin, or optionally substituted chloroeremomycin.

EXAMPLE 24

This example illustrates the preparation of a representative pharmaceutical formulation containing a compound of Formula I, e.g., [C—C]-pentanedioic acid bis-[(2-aminoethyl)amide]-bis-(vancomycin).

An oral suspension is prepared having the following composition.

| Ingredients | |
|---|---|
| Active Compound | 1.0 g |
| Fumaric acid | 0.5 g |
| Sodium chloride | 2.0 g |
| Methyl paraben | 0.1 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

Other compounds of Formula I can be used as the active compound in the preparation of the orally administrable formulations of this example.

EXAMPLE 25

This example illustrates the preparation of a representative pharmaceutical formulation containing an active compound of Formula I, e.g. [C—C]-pentanedioic acid bis[(2-aminoethyl)amide]-bis-(vancomycin).

An injectable preparation buffered to a pH of 4 is prepared having the following composition:

| Ingredients | |
|---|---|
| Active Compound | 0.2 g |
| Sodium Acetate Buffer Solution (0.4 M) | 2.0 ml |
| HCL (1N) | q.s. to pH 4 |
| Water (distilled, sterile) | q.s. to 20 ml |

Other compounds of Formula I can be used as the active compound in the preparation of the injectable formulations of this example.

EXAMPLE 26

This example illustrates the preparation of a representative pharmaceutical formulation for injection containing an active compound of Formula I, e.g. [C—C]-pentanedioic acid bis-[(2-aminoethyl)amide]-bis-(vancomycin).

A reconstituted solution is prepared by adding 20 ml of sterile water to 1 g of the compound of Formula I. Before use, the solution is then diluted with 200 ml of an intravenous fluid that is compatible with the compound of Formula I. Such fluids are chosen from 5% dextrose solution, 0.9% sodium chloride, or a mixture of 5% dextrose and 0.9% sodium chloride. Other examples are lactated Ringer's injection, lactated Ringer's plus 5% dextrose injection, Normosol-M and 5% dextrose, Isolyte E, and acylated Ringer's injection.

Other compounds of Formula I can be used as the active compound in the preparation of the injectable formulations of this example.

EXAMPLE 27

This example illustrates the preparation of a representative pharmaceutical formulation for topical application containing a compound of Formula I, e.g., [C—C]-pentanedioic acid bis-[(2-aminoethyl)amide]-bis-(vancomycin).

| Ingredients | grams |
|---|---|
| Active compound | 0.2–10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

Other compounds of Formula I can be used as the active compound in the preparation of topical formulations of this example.

EXAMPLE 28

This example illustrates the preparation of a representative pharmaceutical formulation containing a compound of Formula I, e.g., [C—C]-pentanedioic acid bis-[(2-aminoethyl)amide]-bis-(vancomycin).

A suppository totalling 2.5 grams is prepared having the following composition:

| Ingredients | |
|---|---|
| Active Compound | 500 mg |
| Witepsol H-15* | balance |

(*triglycerides of saturated vegetable fatty acid; a product of Riches-Nelson, Inc., New York, N.Y.)

Other compounds of Formula I can be used as the active compound in the preparation of the suppository formulations of this example.

EXAMPLE 29

Determination of Antibacterial Activity

In Vitro Determination of Antibacterial Activity

Bacterial strains were obtained from either American Type Tissue Culture Collection (ATCC), Stanford University Hospital (SU), Kaiser Permanente Regional Laboratory in Berkeley (KPB), Massachusetts General Hospital (MGH), the Centers for Disease Control (CDC), the San Francisco Veterans' Administration Hospital (SFVA) or the University of California San Francisco Hospital (UCSF). Vancomycin resistant enterococci were phenotyped as Van A or Van B based on their sensitivity to teicoplanin. Some vancomycin resistant enterococci that had been genotyped as Van A, Van B, Van C1 or Van C2 were obtained from the Mayo Clinic.

Minimal inhibitory concentrations (MICs) were measured in a microdilution broth procedure under NCCLS guidelines. Routinely the compounds were serially diluted into Mueller-Hinton broth in 96-well microtiter plates. Overnight cultures of bacterial strains were diluted based on absorbance at 600 nm so that the final concentration in each well was $5 \times 10^5$ cfu/ml. Plates were returned to a 35° C. incubator. The following day (or 24 hours in the case of Enterococci strains), MICs were determined by visual inspection of the plates. Strains routinely tested in the initial screen included methicillin-sensitive *Staphylococcus aureus* (MSSA), methicillin-resistant *Staphylococcus aureus*, methicillin-sensistive *Staphylococcus epidermidis* (MSSE), methicillin-resistant *Staphylococcus epidermidis* (MRSE), vancomycin sensitive *Enterococcus faecium* (VSE Fm), vancomycin sensitive *Enterococcus faecalis* (VSE Fs), vancomycin resistant *Enterococcus faecium* also resistant to teicoplanin (VRE Fm Van A), vancomycin resistant *Enterococcus faecium* sensitive to teicoplanin (VRE Fm Van B), vancomycin resistant *Enterococcus faecalis* also resistant to teicoplanin (VRE Fs Van A), vancomycin resistant *Enterococcus faecalis* sensitive to teicoplanin (VRE Fs Van B), *Enterococcus gallinarium* of the Van A genotype (VRE Gm Van A), *Enterococcus gallinarium* of the Van C—1 genotype (VRE Gm Van C-1), *Enterococcus casseliflavus* of the Van C-2 genotype (VRE Cs Van C-2), ), *Enterococcus flavescens* of the Van C-2 genotype (VRE Fv Van C-2), and penicillin-sensitive *Streptococcus pneumoniae* (PSSP) and penicillin-resistant *Streptococcus pneumoniae* (PSRP). Because of the inability of PSSP and PSRP to grow well in Mueller-Hinton broth, MICs with those strains were determined using either TSA broth supplemented with defibrinated blood or blood agar plates. Compounds which had significant activity against the strains mentioned above were then tested for MIC values in a larger panel of clinical isolates including the species listed above as well as non-speciated coagulase negative *Staphylococcus* both sensitive and resistant to methicillin. (MS-CNS and MR-CNS). In addition, they are tested for MICs against gram negative organisms, such as *Escherichia coli* and *Pseudomonas aeruginosa*.

Determination of Kill Time

Experiments to determine the time required to kill the bacteria were conducted as described in Lorian. These experiments were conducted normally with both *Staphylococcus* and *Enterococcus* strains.

Briefly, several colonies were selected from an agar plate and grown at 35° C. under constant agitation until it achieved a turbidity of approximately 1.5 and $10^8$ CFU/ml. The sample was then diluted to about $6 \times 10^6$ CFU/ml and incubation at 35° C. under constant agitation was continued. At various times aliquots were removed and five ten-fold serial dilutions were performed. The spread plate method was used to determine the number of colony forming units (CFUs).

The compounds of Formula I were active in the above tests.

In Vivo Determination of Antibacterial Activity

1) Acute Tolerability Studies in Mice.

In these studies, the compounds of Formula I were administered either intravenously or subcutaneously and observed for 5–15 minutes. If there were no adverse effects, the dose was increased in a second group of mice. This dose incrementation continued until mortality occurred, or the dose was maximized. Generally, dosing began at 20 mg/kg and increased by 20 mg/kg each time until the maximum tolerated dose (MTD) is achieved.

2) Bioavailability Studies in Mice

Mice were administered the compound of Formula I either intravenously or subcutaneously at a therapeutic dose (in general, approximately 50 mg/kg). Groups of animals were placed in metabolic cages so that urine and feces could be collected for analysis. Groups of animals (n=3) were sacrificed at various times (10 min, 1 hour and 4 hours). Blood was collected by cardiac puncture and the following organs were harvested-lung, liver, heart, brain, kidney, and spleen. Tissues were weighed and prepared for HPLC analysis. HPLC analysis on the tissue homogenates and fluids was used to determine the concentration of the compound of Formula I present. Metabolic products resulting from changes to the compound of Formula were also determined at this juncture.

3) Mouse Septecemia Model.

In this model, an appropriately virulent strain of bacteria (most commonly *S. aureus*, or *E. Faecalis* or *E. Faecium*) was administered to mice (N=5 to 10 mice per group) intraperitoneally. The bacteria was combined with hog gastric mucin to enhance virulence. The dose of bacteria (normally $10^5$–$10^7$) was that sufficient to induce mortality in all of the mice over a three day period. One hour after the bacteria was administered, the compound of Formula I was administered in a single dose either IV or subcutaneously. Each dose was administered to groups of 5 to 10 mice, at doses that typically ranged from a maximum of about 20 mg/kg to a minimum of less than 1 mg/kg. A positive control (normally vancomycin with vancomycin sensitive strains) was administered in each experiment. The dose at which approximately 50% of the animals are saved was calculated from the results.

4) Neutropenic Thigh Model.

In this model antibacterial activity of the compound of Formula I was evaluated against an appropriately virulent strain of bacteria (most commonly *S. aureus*, or *E. Faecalis* or *E. Faecium*, sensitive or resistant to vancomycin). Mice were initially rendered neutropenic by administration of cyclophosphamide at 200 mg/kg on day 0 and day 2. On day 4 they were infected in the left anterior thigh by an IM injection of a single dose of bacteria. The mice were then administered the compound of Formula I one hour after the bacteria and at various later times (normally 1, 2.5, 4 and 24 hours) the mice were sacrificed (3 per time point) and the thigh excised, homogenized and the number of CFUs (colony forming units) were determined by plating. Blood was also plated to determine the CFUs in the blood.

5) Pharmacokinetic Studies

The rate at which the compound of Formula I was removed from the blood can be determined in either rats or mice. In rats, the test animals were cannulated in the jugular vein. The compound of Formula I was administered via tail vein injection, and at various time points (normally 5, 15, 30, 60 minutes and 2,4,6 and 24 hours) blood was withdrawn from the cannula. In mice, the compound of Formula I was also administered via tail vein injection, and at various time points. Blood was normally obtained by cardiac puncture. The concentration of the remaining compound of Formula I was determined by HPLC.

The compounds of Formula I were active in the above tests, and demonstrated a broad spectrum of activity.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of the formula:

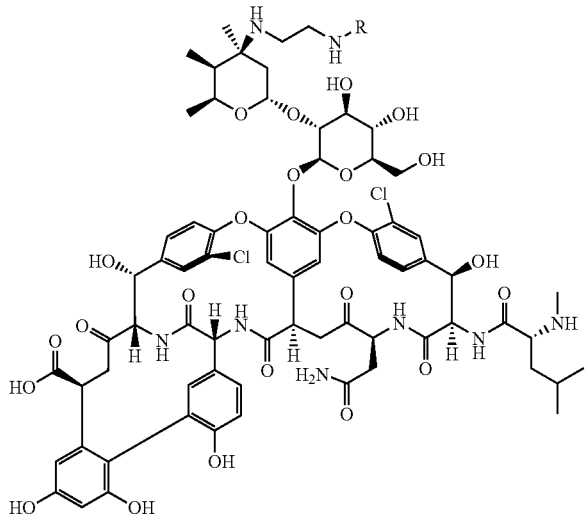

wherein

R is a hydrogen or 9-fluorenylmethoxycarbonyl;

or a pharmaceutically-acceptable salt thereof.

2. The compound according to claim 1, wherein R is hydrogen.

3. The compound according to claim 1, wherein R is 9-fluorenylmethoxycarbonyl.

* * * * *

UNITED STATES PATENT AND TRADEMARK OFFICE
CERTIFICATE OF CORRECTION

PATENT NO.        : 7,067,620 B2  
APPLICATION NO.   : 10/274557  
DATED             : June 27, 2006  
INVENTOR(S)       : Qi-Qi Chen, John H. Griffin and Martin S. Linsell It is certified that error appears in the above-identified patent and that said Letters Patent is hereby corrected as shown below:

On the Title page, and Col. 1, Line 1  
Item (54), "ANTIBACTERIAL AGENTS" should read -- DERIVATIVES OF GLYCOPEPTIDE ANTIBACTERIAL AGENTS --.

Column 150  
line 5, the formula                                       should read " 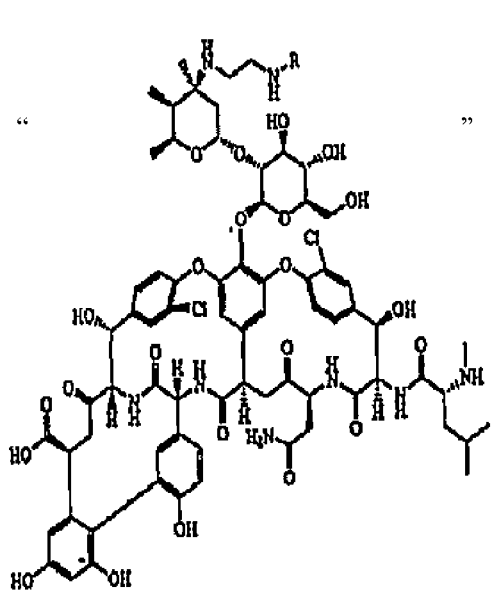 "    --  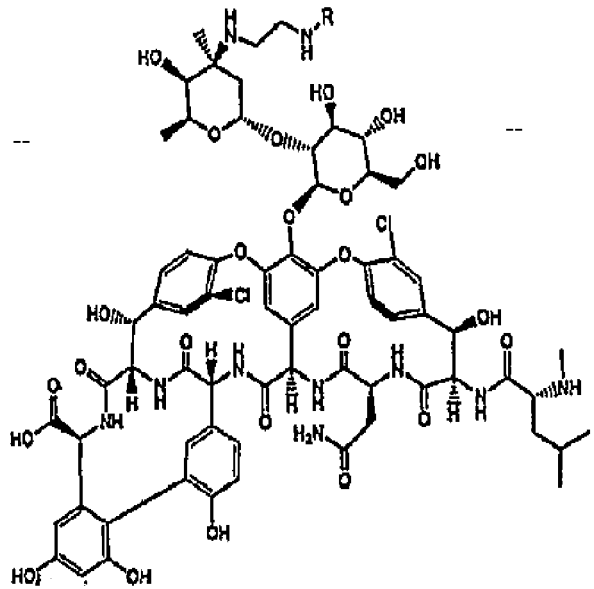  --

Signed and Sealed this

Twenty-sixth Day of December, 2006

JON W. DUDAS  
*Director of the United States Patent and Trademark Office*